United States Patent [19]

Fukui et al.

[11] Patent Number: 4,818,614
[45] Date of Patent: Apr. 4, 1989

[54] MODIFIED POWDER

[75] Inventors: Hiroshi Fukui; Ryujiro Namba; Tsutomu Saito; Yutaka Ohtsu; Asa Kimura; Motokiyo Nakano; Okitsugu Nakata; Kenichi Tomita; Kazuo Tokubo; Kazuhisa Ohno; Toshio Yoneyama; Takashi Ogawa; Hideo Morohoshi; Junichi Koyama; Taketoshi Kanda; Kunihiro Kawaguchi; Yuzo Shimizu, all of Yokohama, Japan

[73] Assignee: Shiseido Company Ltd., Tokyo, Japan

[21] Appl. No.: 891,001

[22] Filed: Jul. 25, 1986

[30] Foreign Application Priority Data

| Jul. 29, 1985 | [JP] | Japan | 60-165974 |
| Sep. 3, 1985 | [JP] | Japan | 60-194654 |
| Nov. 15, 1985 | [JP] | Japan | 60-256166 |
| Nov. 26, 1985 | [JP] | Japan | 60-265715 |
| Feb. 5, 1986 | [JP] | Japan | 61-023518 |
| Feb. 18, 1986 | [JP] | Japan | 61-033595 |
| Mar. 25, 1986 | [JP] | Japan | 61-066635 |
| Apr. 3, 1986 | [JP] | Japan | 61-077301 |
| Apr. 3, 1986 | [JP] | Japan | 61-077302 |
| Apr. 5, 1986 | [JP] | Japan | 61-078740 |
| Apr. 5, 1986 | [JP] | Japan | 61-078741 |
| May 9, 1986 | [JP] | Japan | 61-106175 |
| May 23, 1986 | [JP] | Japan | 61-118901 |
| May 28, 1986 | [JP] | Japan | 61-122821 |
| May 31, 1986 | [JP] | Japan | 61-127047 |
| Jun. 10, 1986 | [JP] | Japan | 61-134540 |
| Jun. 13, 1986 | [JP] | Japan | 61-137838 |
| Jun. 13, 1986 | [JP] | Japan | 61-137839 |
| Jun. 13, 1986 | [JP] | Japan | 61-137840 |

[51] Int. Cl.$^4$ .................... B32B 9/00; B05D 7/00; C09C 3/12; A61K 7/02
[52] U.S. Cl. .................... 428/403; 428/405; 428/407; 106/481; 427/215; 424/63
[58] Field of Search ............... 428/403, 405, 447, 215, 428/216; 427/219; 106/308 B, 308 Q

[56] References Cited

U.S. PATENT DOCUMENTS

| 2,891,923 | 6/1959 | Phreaner | 523/212 |
| 3,649,321 | 3/1972 | Durrant et al. | 523/212 |
| 3,849,152 | 11/1974 | Mimeault | 106/308 Q |
| 3,920,865 | 11/1975 | Laüfer et al. | 427/220 |
| 4,034,139 | 7/1977 | Mazarguil et al. | 428/405 |
| 4,062,693 | 12/1977 | Berger | 106/308 Q |
| 4,151,154 | 4/1979 | Berger | 260/40 R |
| 4,191,587 | 3/1980 | Kratel et al. | 106/308 Q |
| 4,394,469 | 7/1983 | Stratta | 523/213 X |
| 4,578,266 | 3/1986 | Tietjen et al. | 424/63 |

OTHER PUBLICATIONS

N. Morimoto, et al. "Kobutshu-gaku (Mineralogy)" Iwanami Pub. Co., p. 483, 1975.
Chigaku-jiten (Dictionary of Physical Geography)–Heibon-sha Pub. Co., p. 1167, 1978.

Primary Examiner—Ellis P. Robinson
Assistant Examiner—Susan S. Rucker
Attorney, Agent, or Firm—Sprung Horn Kramer & Woods

[57] ABSTRACT

A modified powder or particulate material coated on substantially the entire surface thereof with a film of a silicone polymer carrying a pendant group thereon, this powder or particulate material being produced by a process comprising the steps of (a) coating the powder or particulate material with a film of a silicone polymer having at least one Si-H moiety, and
(b) carrying out an addition reaction of a compound capable of reacting with an Si—H moiety to the Si—H moiety in the silicone polymer of step (a), whereby the pendant group derived from said compound is bonded to the silicone polymer.

32 Claims, 6 Drawing Sheets

MODIFIED POWDER

BACKGROUND OF THE INVENTION

1. Field of the Invention

The present invention relates to a modified powder or particulate material coated on substantially the entire surface thereof with a film of a silicone polymer carrying at least one pendant group thereon. More specifically, it relates to a modified powder or particulate material obtained by coating a powder or particulate material with a film of a silicone polymer, and thereafter, carrying out an addition reaction to introduce a pendant group into the silicone polymer, whereby the surface activities of the powder or particulate material are disappeared, the unpreferable generation of hydrogen from the surface due to a coexisting $H_2O$ or alcohol can be prevented, and various characteristics (e.g., dispersibility, UV absorbability) can be afforded to the powder or particulate material by appropriately selecting the pendant group.

The term "powder or particulate material" (i.e., "powder material" hereinbelow) used herein means any material generally having a particle size of 10 mm or less, but sometimes more than 10 mm. The agglomerates and the molded or shaped products of the powder material and the burned products thereof are also included in this term. According to the present invention, any powder material including an ultrafine powder having a size of 0.02 $\mu$m or less can be modified.

The term "pendant group" used herein means a residue of a compound capable of reacting with an Si—H moiety, which residue is introduced to the silicone polymer by the addition reaction of the compound. This pendant group provides various characteristics or functions to the powder material.

The modified powder material according to the present invention does not denature or decompose perfumes, oils, or resins even when coexisting therewith, and therefore, will not cause problems such as denaturation, odor change, and color change and can be utilized in the fields of, for example, cosmetics, pharmaceuticals, resin compositions, coating materials, inks, paints, decoratives, fragrants, magnetic materials, and medical materials. Further, Si—H moieties contained in the silicone polymer film coating the powder material can be substantially eliminated or considerably reduced so that the powder material can be effectively formulated into, for example, an emulsion system. Furthermore, composite materials having various functions can be provided.

2. Description of the Related Art

Silicone oils have been frequently used in the prior art for the hydrophobic modification of a powder material. For example, Japanese Examined Patent Publication (Kokoku) No. 41-9890 discloses imparting lubricity to an animal, vegetable or mineral powder by coating the surface of the powder with a silicone resin coating material, followed by drying and baking. In Japanese Examined Patent Publication (Kokoku) No. 45-2915, a mineral powder such as talc is simply attached with a silicone having hydrogen directly bonded to silicone in the molecular chain by, for example, blender mixing, followed by heat baking, thereby imparting a water repellency to the powder. According to Japanese Examined Patent Publication (Kokoku) No. 45-18999, talc is attached with dimethylpolysiloxane or methylhydrogenpolysiloxane by contact with an organic solvent solution thereof, followed by baking optionally with the addition of a substance such as zinc octoate as the crosslinking polymerization catalyst for methylhydrogenpolysiloxane, thereby imparting a free flow property to the powder. Further, in Japanese Examined Patent Publication (Kokoku) No. 49-1769, titanium dioxide is subjected to direct coating, emulsion coating or solvent solution coating of various alkylpolysiloxanes, and then dried and baked optionally by using, in combination, an ester compound having a total carbon number of 6 or more, whereby the dust property, dispersibility, etc., of the powder are modified. On the other hand, in Japanese Unexamined Patent Publications (Kokai) Nos. 56-16404, 55-136213, and 56-29512, after mixing under stirring with the addition of silicone oils and oil agents or by the application of a mechanochemical reaction such as crushing, a baking treatment is performed.

Further, Japanese Unexamined Patent Publication (Kokai) No. 57-200306 discloses a method for imparting a water repellency and flow property to a powder without the application of a baking treatment by treating the powder with (A) a silane compound having a specific structure, (B) a cyclic polyorganosiloxane, and (C) a linear polyorganosiloxane. According to this method, 1 to 10% by weight based on the powder to be treated of the above organic silicone compound is adsorbed onto the powder by spraying a solution diluted in a solvent, direct spraying, or gaseous atomization, or by directly mixing under stirring, and then a water or water vapor treatment is applied. In the (B) cyclic polyorganosiloxane, the trimer having a methyl group is excluded, because it is solid and difficult to handle.

However, according to these methods, in most organic pigments and inorganic pigments, those weakly resistant to heat, such as yellow iron oxide or prussian blue, could not be treated.

For example, among the organic pigments, C.I. 15850:1 (lithol rubine BCA) could not be treated, because it was dehydrated at 80° C. and changed crystal form from $\alpha$-type to $\beta$-type simultaneously with a change in tone. On the other hand, prussian blue is decomposed by the application of heat and gradually releases cyan gas at 150° C. or higher. Baking treatment is carried out at 350° C. for 2 hours, as a typical example of a higher temperature treatment, or at 150° C. for 15 to 40 hours, as a typical example of a lower temperature treatment. Under such conditions, prussian blue not only undergoes a color change but also releases harmful cyan gas, thus being very dangerous.

Such a baking treatment of the prior art can be applied only for a part of stable inorganic pigments, and has the vital defect that treatment of an organic pigment which has a brilliant alters color its color tone.

We have found and disclosed, in our copending application entitled "Modified Powder or Particulate Material" Ser. No. 875,140, filed on June 16, 1986, that the above-mentioned disadvantages can be eliminated by a modified powder or particulate material produced by bringing a certain silicone compound in the form of a vapor into contact with the powder or particulate material. In the method disclosed in our said copending application, the silicone compound is brought into contact with the powder material and polymerizes thereon, and Si—H moieties are crosslinked on the surface of the powder material to form the silicone polymer film thereon. However, steric hindrance interferes with the proceeding of the crosslinking. Because the crosslinking does not fully proceed, i.e., unreacted Si—H moieties remain, the powder material obtained in our said copending application may be unstable under a severe alkaline or acidic condition.

A treatment with methyl hydrogen polysiloxane has an advantage that it can be carried out under a relatively low temperature. However, the powder material treated with methyl hydrogen polysiloxane does not always exhibit a sufficient stability, because it may cause generation of $H_2$ under the coexistence of $H_2O$ or an alcohol therewith, due to the remaining Si—H moieties present in the silicone polymer film formed on the powder material.

A hydrophobic nature can be imparted to the powder material by the treatment with, for example, methyl hydrogen polysiloxane. However, if a powder material having an optimum dispersibility in a given oil or resin is obtained, the powder material should be treated with an alkyl/aryl hydrogen polysiloxane having the specific alkyl or aryl groups selected with respect to the oil or resin. In some cases, it is necessary and possible to use the polysiloxane having long hydrocarbon residues. However, a boiling or melting point of such a polysiloxane is very high, and thus, it is difficult to treat the powder material with such a polysiloxane in the preferable forms thereof, i.e., vaporized polysiloxane.

Further, it is difficult to obtain the powder material coated with a film of the silicone polymer carrying various functional groups (e.g., —$NH_2$, —COOH, —CN) thereon, because a treating agent containing Si—H moieties and such functional groups is not easily available.

A silane coupling agent is conventionally used so as to introduce the functional group to the powder material. For example, a silica can be easily treated with the silane coupling agent. However, there are some powder materials such as zinc oxide or titanium dioxide difficult to be treated with the silane coupling agent. Further, the silane coupling agent is introduced to, for example, the metal oxide, by the reaction with an OH group present on the surface of the metal oxide. Therefore, the functional groups introduced by the silane coupling agent cannot be firmly attached to the metal oxide. Furthermore, the treatment with the silane coupling agent does not result in the polymer film coating substantially the entire surface of the metal oxide. Thus, metal atoms are exposed on the surface thereof, and the surface activity of the metal oxide cannot be blocked. Therefore, the metal oxide treated with the silane coupling agent may cause problems such as denaturation and odor change when formulated in, for example, cosmetics. Further, although a hydrophobic nature can slightly be obtained, a dispersibility of the powder material cannot be controlled by such a treatment.

SUMMARY OF THE INVENTION

Accordingly, the object of the present invention is not only to eliminate the above-mentioned disadvantages of the prior art, but also provide an improvement of the invention disclosed in our copending application, i.e., a modified powder or particulate material which has improved properties including a hydrophobic nature and stability with a disappearance of the surface activities thereof (i.e., not capable of denaturing or decomposing other substances if coexisting), can be formulated into, for example, an emulsion system, carries various functions and maintains the inherent characteristics of the powder or particulate material to be modified.

Other objects and advantages of the present invention will be apparent from the following description.

In accordance with the present invention, there is provided a modified powder or particulate material coated on substantially the entire surface thereof with a film of a silicone polymer carrying a pendant group thereon, this powder or particulate material being produced by a process comprising the steps of (a) coating the powder or particulate material with a film of a silicone polymer having at least one Si—H moiety, and (b) carrying out an addition reaction of a compound capable of reacting with a Si—H moiety to the Si—H moiety in the silicone polymer of step (a), whereby the pendant group derived from the compound is bonded to the silicone polymer.

BRIEF DESCRIPTION OF THE DRAWINGS

The present invention will be better understood from the description set forth below with reference to the accompanying drawings illustrating, but not intended to be limited to, the preferred embodiments of the present invention, in which.

DESCRIPTION OF THE PREFERRED EMBODIMENTS

Figure 1:
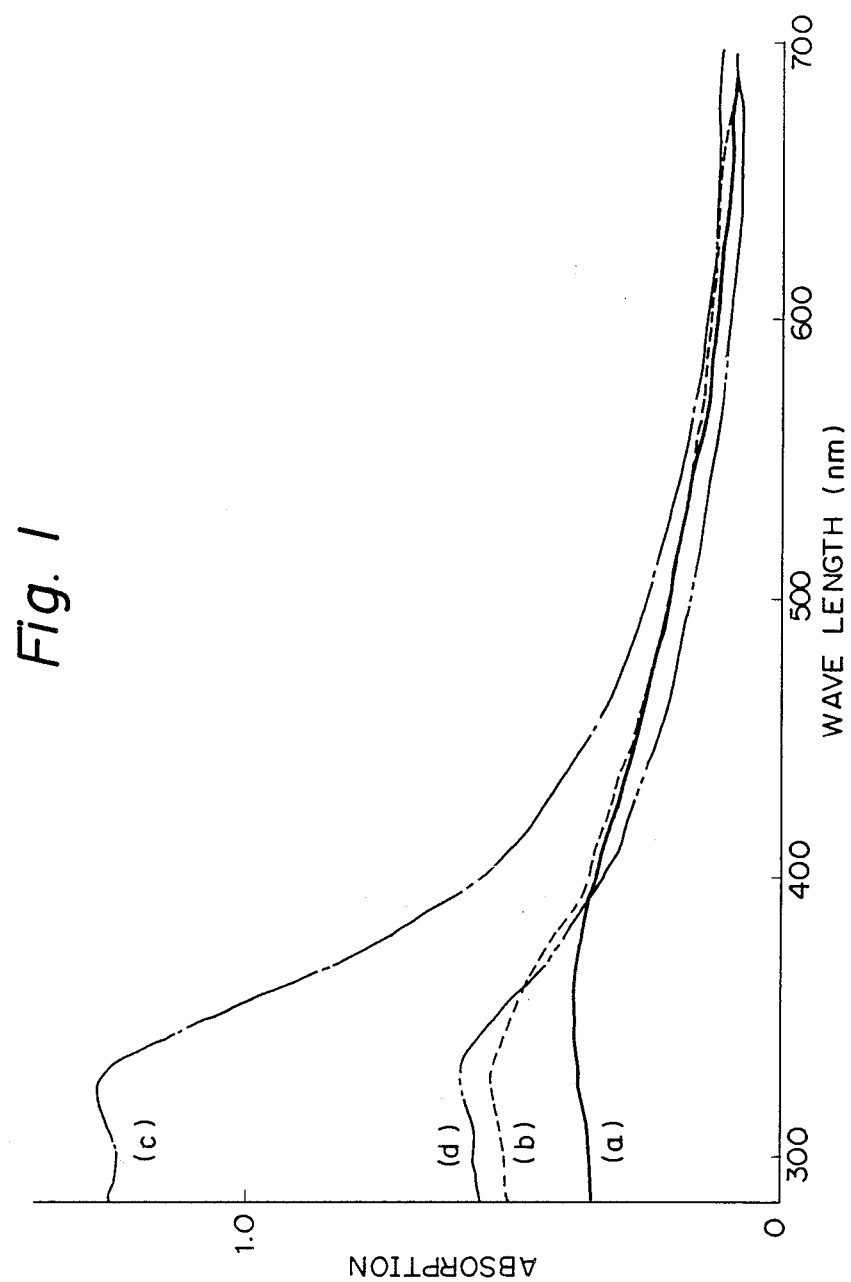
FIGS. 1 and 2 show the UV absorption spectrum of the titanium dioxide powder samples of the untreated powder [i.e., chart (a)], Example 4-2(1) [i.e., chart (b)], Example 4-2(2) [i.e., chart (c)], and Example 4-2(3) [i.e., chart (d)] dispersed in liquid paraffin and castor oil, respectively.

Although there are no critical limitations to the powder materials to be modified according to the present invention, typical examples of such powders are inorganic pigments, metallic oxides and hydroxides, mica, organic pigments, pearling materials (or nacreous pigments), mineral silicates, porous materials, carbons, metals, biopolymers, and composite powder or particulate materials. These powder materials may be used alone or in any mixture thereof. Furthermore, these powder materials to be modified may have other substances (e.g., coloring agents, UV absorbers, medicaments, various additives) deposited thereon or included therein.

In the first stage of the modification according to the present invention, the powder material is coated with the film of the silicone polymer having at least one Si—H moiety. Any silicone compound can be used in the coating step, as long as the film of the silicone polymer having at least one Si—H moiety can be formed therefrom on the surface of the powder material.

In the coating step of the present invention, there may be used a silicone compound having at least one Si—H moiety, preferably a silicone compound having the general formula (I):

$$(R^1HSiO)_a(R^2R^3SiO)_b(R^4R^5R^6SiO_{\frac{1}{2}})_c \qquad (I)$$

wherein $R^1$, $R^2$, and $R^3$ represent, independently, hydrogen or a hydrocarbon residue having 1 to 10 carbon atoms, which may be substituted with at least one halogen atom, provided that $R^1$, $R^2$, and $R^3$ are not hydrogen at the same time, $R^4$, $R^5$, and $R^6$ represent, independently, hydrogen or a hydrocarbon residue having 1 to 10 carbon atoms, which may be substituted with at least one halogen atom, a is zero or an integer of 1 or more, b is zero or an integer of 1 or more, and c is zero or 2, provided that a+b is an integer of 3 or more when c is zero, and the maximum value of a+b+c is 10,000. Each of the groups $R^1$ to $R^6$ in the formula (I) may be different in each of the recurring units.

The silicone compounds having the general formula (I) can be typically separated into two groups. That is, the first group of the silicone compounds (I) has the following structure (II):

$$(R^1HSiO)_a(R^2R^3SiO)_b \qquad (II)$$

wherein $R^1$, $R^2$, $R^3$, a and b are the same as defined above, and preferably $R^1$, $R^2$, and $R^3$ represent, independently, a lower alkyl group having 1 to 4 carbon atoms or an aryl group (e.g., a phenyl group) which may be substituted with at least one halogen atom and a+b is 3 or more.

The second group of the silicone compounds (I) has the following structure (III):

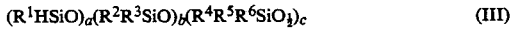
$$(R^1HSiO)_a(R^2R^3SiO)_b(R^4R^5R^6SiO_{\frac{1}{2}})_c \qquad (III)$$

wherein $R^1$, $R^2$, $R^3$, $R^4$, $R^5$, $R^6$, a and b are the same as defined above and c is 2, preferably, $R^1$ to $R^6$ independently represent a lower alkyl group having 1 to 4 carbon atoms or an aryl group (e.g., a phenyl group).

The coating in the first stage of the modification according to the present invention can be carried out in various manners including conventional manners.

For example, the powder material can be coated with the film of the silicone polymer by dissolving a high polymeric silicone compound in an organic solvent (e.g., chloroform, hexane, benzene, toluene, acetone), dispersing the powder material therein, and heating the dispersion to evaporate the solvent, thereby forming the film on the powder material. Further, the film can be formed by drying the dispersion of the powder material by means of a spray drier. Furthermore, the powder material can be coated by pouring the dispersion in a poor solvent of the high polymeric silicone compound, and vice versa, thereby depositing the insolubilized silicone compound on the surface of the powder material to form the film thereof.

The coating can be performed by mechanochemically treating the powder material with the high polymeric silicone compound in the form of a liquid, in, for example, a ball mill.

It is also possible to encapsulate the powder material with the film of the silicone polymer by polymerizing silicone compound monomers on the surface of the powder material in the presence of a catalyst as an in-situ polymerization.

Alternatively, the coating in the first stage of the modification according to the present invention can be carried out, making use of active sites entirely prevailing on the surface of the powder material to be modified. The term "active site" used herein means those capable of catalytically polymerizing a silicone compound having a siloxane bond (Si—O—Si) or a hydrosilyl moiety (Si—H) (i.e., acidic, basic, oxidative, or reductive sites).

In the coating step using the active sites, the powder material may be brought into contact with the silicone compound in the form of a vapor, as a solution in a suitable solvent, or in the form of a liquid, whereby the silicone compound is polymerized on the surface of the powder material.

The contact between the powder material and the liquid silicone compound per se (hereinafter referred to as a "liquid phase treatment") may be mechanochemically carried out by charging the powder material into a suitable mixer such as a rotary ball mill, vibration ball mill, satellite ball mill, sand mill, atomizer, pug mill, pony mixer, automated mortar or the like. It is to be noted that the above liquid phase treatment may cause a change of shape of the powder material. The powder materials which may be subjected to the liquid phase treatment are, for example, a mixture of talc, mica or spherical resin (e.g., nylon, polyethylene, cellulose) and a fine powder such as pigment. When the mixture is treated with the liquid silicone compound while mixing the talc, mica or spherical resin with the pigment, the talc, mica or spherical resin, as a core, is coated with the pigment and the silicone polymer film thereon.

Furthermore, as the liquid phase treatment, the silicone compound dissolved in a suitable solvent may be brought into contact with the powder material. As the solvent for the silicone compound, there may be used an organic solvent, for example chloroform or hexane. In the liquid phase treatment, a solution containing 1 to 50% by weight of the silicone compound is prepared. Thereafter, the powder material may be dispersed in the solution and the whole is heated to evaporate the solvent and polymerize the silicone compound on the surface thereof. Alternatively, the solution may be sprayed directly onto the powder material, and then the material may be heated to evaporate the solvent and polymerize the compound. The powder materials which can be easily filtrated (e.g., talc, mica, etc.) may be subjected to the liquid phase. The silicone compounds suitable for the liquid phase treatment are, for example, the compound of the formula (I) wherein a+b+c is 10,000 or less.

The powder material can be brought into contact with the silicone compound in the form of a vapor (hereinafter referred to as a "vapor phase treatment").

In the vapor phase treatment, the silicone compound can be brought into contact with the powder material at a temperature of 120° C. or less, preferably 100° C. or less, in a closed chamber in such a manner that vaporized silicone compound is deposited under a molecular state on the surface of the powder material, preferably under a pressure of 200 mmHg or less, more preferably 100 mmHg or less. Alternatively, the silicone compound in the form of a vapor can be brought into contact with the powder material by feeding a gas mixture of the silicone compound and a carrier gas at a temperature of 120° C. or less, preferably 100° C. or less.

The treatment amount in the vapor phase treatment is not determined, because the silicone compound evaporated will be polymerized by the active site of the powder material after adsorption on the powder material, and the time when the polymer has completely covered the active sites is the end point of the treatment.

The amount of the silicone compound is not specifically determined, but the desired amount is specific in that the silicone compound is supplied in an amount which is necessary and sufficient to cover substantially the entire surface of the powders.

Thus, in the vapor phase treatment, any kind of powder can be treated without an excess or shortage of treatment. This is because the method of adding the treating agent is different from other methods. In the vapor phase treatment, the treating agent is not added in the form of a liquid but is permitted to come into contact with the powder in molecular form and, therefore, the original treating agent may be either solid or liquid. Also, in view of the polymerization on the powder surface, a trimer or tetramer is most readily polymerizable and, therefore, most suitable as a treating agent. That is, the specific feature of the vapor phase treatment resides in the energy-saving type method in which the powder is left to stand in a low partial pressure state wherein a silicone compound is volatilized at a temperature of 120° C. or lower, thereby permitting the vaporized product of the silicone compound to be adsorbed, and deposited under the molecular state onto the powder, and polymerized from the active sites on the surface.

In the vapor phase treatment, the silicone compound is first deposited on the surface of the powder material and the polymerization thereof occurs due to the presence of active sites entirely prevailing on the surface of the powder materials. Thus, the uniform thin polymer film is formed. After forming the thin layer of the silicone polymer, no substantial polymerization occurs thereover. Accordingly, the thickness of the silicone polymer film formed in this stage is generally 3 to 30 Å. On the other hand, when the thermal polymerization occurs, it is impossible to effect the thin layer-forming-polymerization. Furthermore, when the polymerization is effected in the presence of a catalyst, the polymerization occurs mainly around the catalyst and, therefore, it is impossible or very difficult to uniformly cover or coat only the surface of the powder material.

The vapor phase treatment applies no heating treatment and, therefore, is applicable also for a pigment with a low temperature stability. Thus, it can be utilized for a very wide scope of applications.

According to the basic method of the vapor phase treatment, the powder material and the silicone compound may be placed in a closed chamber, and contained in separate vessels with their upper portions open. Due to the presence of polymerization activity, the silicone compound is polymerized on the powder material, whereby the partial pressure of the silicone compound on the powder surface is lowered and, therefore, the silicone compound in the vessel is then evaporated to be supplied to the powder material. Since the surface polymerization occurs in such an order, in this system the silicone compound is supplied only in a necessary amount without waste.

The above vapor phase treatment is based on a very simple principle, and therefore, special equipment is not necessarily required. For example, any closed or sealed chamber such as a desiccator or a constant temperature chamber may be used. The powder material may be agitated intermittently, in a chamber, so as to effect the desirable contact of the powder material with the vaporized silicone compound. It it also possible to employ a method in which only the powder is previously placed in a closed chamber of 120° C. or less, preferably 100° C. or less, the silicone compound is volatilized under a predetermined partial pressure in another closed chamber of 120° C. or lower, and the volatilized silicone compound is introduced into the room in which the above powder is placed, through, for example, a pipe. Although there are no critical limitations to the pressure of the system, the polymerization is preferably carried out under a pressure of 200 mmHg or less, more preferably 100 mmHg or less. In any of the methods of the vapor phase treatment, the treatment time is from 30 minutes to 150 hours, and thereafter, the unpolymerized silicone compound is removed by degassing to obtain the desired product.

According to another method of the vapor phase treatment, the powder material can be treated by bringing it into contact with the silicone compound in the form of a gas mixture thereof with a carrier gas. The silicone compound can be mixed with a carrier gas by, for example, heating (if necessary) the silicone compound until the vapor pressure thereof becomes 1 mmHg or more, preferably 100 mmHg or more, followed by introducing a carrier gas stream into the silicone compound or the surface thereof. The feed rate of the carrier gas stream can be appropriately determined depending upon, for example, the vapor pressure of the silicone compound, the kinds and the amounts of the powder material, and the volume of the treating vessel, so that the treatment of the powder material can be completed for the predetermined time, preferably 30 minutes to 150 hours. Examples of the carrier gases usable in the vapor phase treatment are preferably inert gases such as nitrogen, argon, and helium, but air or a gas mixture of the above-mentioned inert gas with vaporized water, methanol or ethanol also may be used in the present invention.

In the above vapor phase treatment, a gas mixture containing the silicone compound is brought into contact with the powder material to be modified. The gas mixture contains the silicone compound as a saturated vapor and, therefore, the contact temperature should be the same as or higher than the temperature of the gas mixture.

Thus, in the vapor phase treatment, an inert gas is simply introduced into a solution of the organosilicone compound and the molecules of the silicone compound are continuously adsorbed on the surface of the powder material, whereby the silicone compound is polymerized due to the presence of the active sites on the powder material. Thus, the method of the vapor phase treatment is an energy-saving type method and is completely different from the conventional spraying and thermal polymerizing methods.

Conveniently, all the powder materials to be modified according to the present invention can be subjected to the vapor phase treatment. However, it is preferable to utilize the vapor phase treatment for ultrafine powder, porous powder material, pearling pigment, organic pigment or the like. When these powder materials are subjected to the vapor phase treatment, a ultrathin film of the silicone polymer is formed thereon. Therefore, their characteristics such as an ultrafineness, porosity, or pearling effect are maintained. Further, a metal to be readily oxidized can be rendered resistant to oxidation by subjecting the metal to the vapor phase treatment immediately after formation thereof. The silicone compounds suitable for the vapor phase treatment are, for example, the compound of the formula (I) wherein a+b+c is 3 to 10, preferably 3 to 7. Typical examples of such compounds are as follows:

(A)
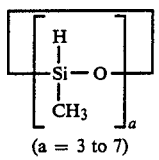
(a = 3 to 7)

(B)
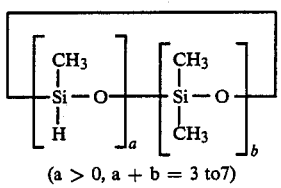
(a > 0, a + b = 3 to 7)

(C)
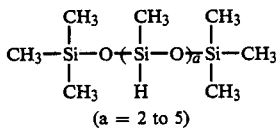
(a = 2 to 5)

These compounds (A), (B), and (C) may be used alone or in any mixture thereof.

Examples of the cyclic silicone compounds suitable for the vapor phase treatment are dihydrogen hexamethyl cyclotetrasiloxane, trihydrogen pentamethyl cyclotetrasiloxane, tetrahydrogen tetramethyl cyclotetrasiloxane, dihydrogen octamethyl cyclopentasiloxane, trihydrogen heptamethyl cyclopentasiloxane, tetrahydrogen hexamethyl cyclopentasiloxane, and pentahydrogen pentamethyl cyclopentasiloxane. These compounds may be used alone or in any combination thereof.

Examples of the linear silicone compounds suitable for the vapor phase treatment are 1,1,1,2,3,4,4,4-octamethyltetrasiloxane, 1,1,1,2,3,4,5,5,5-nonamethylpentasiloxane, and 1,1,1,2,3,4,5,6,6,6-decamethylhexasiloxane.

In general, a silicone compound having at least two Si-H moieties in a molecule is preferable. But, a silicone compound including a silicon atom with two hydrogen atom bonded thereto due to the excess hydrogen atoms is rarely available.

The silicone polymer coating the surface of the powder materials typically has two types of structures. That is, when the polymerization is caused by a siloxane linkage (—Si—O—Si—), the resultant silicone polymer has a linear structure containing a —Si—O—Si— unit and preferably having a weight-average molecular weight of more than 200,000.

On the other hand, when the polymerization is caused by the dehydrogenation reaction of hydrosilyl linkages (Si-H) in the presence of a small or trace amount of $H_2O$ or $O_2$, the resultant silicone polymer has a network structure having a

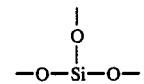

unit derived from the polymerization of Si—H moieties as follows:

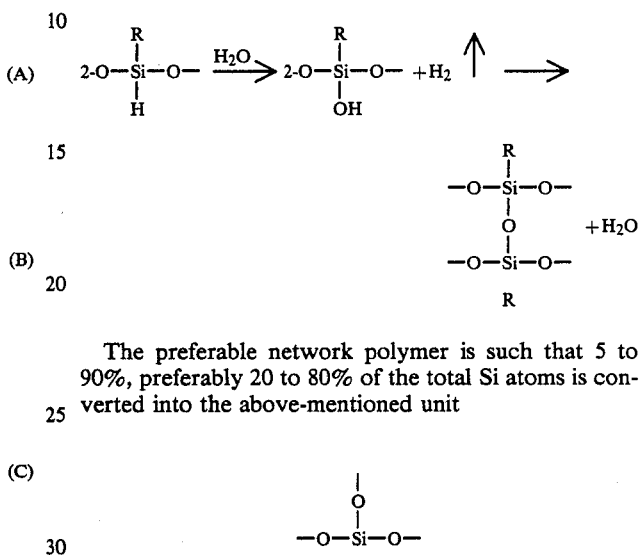

The preferable network polymer is such that 5 to 90%, preferably 20 to 80% of the total Si atoms is converted into the above-mentioned unit $$-O-\underset{|}{\overset{|}{Si}}-O-$$

in the polymer film. The content of this unit can be determined from the IR absorbance of the methyl group in the polymer film.

Although the amount of the silicone polymer film formed on the surface of the powder material in the first stage may differ depending on the powder employed, the amount of the polymer film is preferably 0.005% to 95% by weight based on the weight of the coated powder material.

Prior to the coating step of the first stage of the modification according to the present invention, the powder materials can be treated by any conventional technique (e.g., alkali or acid washing, plasma treatment). In the case of powder materials having many acidic sites thereon (e.g., kaolinite, iron oxides, manganese violet), it is preferable to subject those powder materials to alkali washing, because the subsequent contact with the silicone compound results in a formation of the silicone polymer film having the network structure.

Further, the modified powder material of the present invention having a desired color or UV absorbability can conveniently be prepared by adsorbing a colorant or UV absorber to the powder material prior to the coating step with the silicone powder film. For example, a conventional clay mineral containing UV absorbers merely inserted between layers thereof by means of intercalation may release unstable UV absorbers in a solvent, whereas such a release can be prevented by coating the powder material containing UV absorbers with the silicone polymer film.

UV absorbers adsorbed to the powder material may serve as the active sites. In this case, the silicone polymer is formed on the surfaces carrying the adsorbed UV absorbers by bringing the powder material into contact with the silicone monomer compound.

There may be mentioned, as the UV absorber, for example, 2-hydroxy-4-methoxybenzophenone, 2,2'- dihydroxy-4,4'-dimethoxybenzophenone, 2,2'-dihydroxy-4,4'-dimethoxybenzophenone sulfate, 2,2'4,4'-tetrahydroxybenzophenone, 2,2'-dihydroxy-4,4'-dimethoxybenzophenone, 2-hydroxy-4-methoxybenzophenone sulfate, 2-(2-hydroxy-5'-methylphenyl)-benzotriazole, 2-ethylhexyl p-dimethylaminobenzoate, amyl p-dimethylaminobenzoate, methyl 2,5-diisopropylcinnamate, urocanic acid, or the like.

As explained above, the silicone compound adsorbed on the surface of the powder material by means of the liquid or vapor phase treatment may be polymerized due to the active sites on the powder surface to form the silicone polymer film. When the powder surface is covered with the silicone polymer film, and the active sites thereon are blocked, the subsequent adsorption and polymerization do not proceed and thus the formation of the film ceases. After removing unreacted silicone compound, the powder material carrying only the silicone polymer can be obtained.

In a second stage of the modification according to the present invention, the addition reaction of the compound capable of reacting with an Si-H moiety (hereinafter referred to as "Si—H reactive compound") is carried out to the unreacted Si—H moieties in the silicone polymer formed in the first stage, thereby introducing a pendant group derived from the Si—H reactive compound to the silicone polymer.

In the addition reaction, a compound having an OH group or SH group, for example, an amino acid (e.g., cysteine), may be used. Further, any unsaturated hydrocarbon compound having at least one carbon-carbon double or triple bond may be used.

A suitable unsaturated hydrocarbon compound is a compound having the general formula (V):

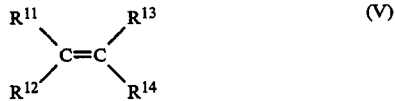

(V)

wherein $R^{11}$, $R^{12}$, $R^{13}$, and $R^{14}$ represent, independently, hydrogen, halogen, hydroxyl, mercapto, acyloxy, alkoxy, amino, nitro, carboxyl, sulfo, or an unsubstituted or substituted hydrocarbon residue having 1 to 30 carbon atoms, for example, an aliphatic residue (e.g., alkyl, alkenyl or alkynyl), an aromatic residue (e.g., phenyl or naphthyl), a heterocyclic residue (e.g., those containing one or more nitrogen, oxygen or sulfur as a heteroatom), an alicyclic residue (e.g., cycloalkyl, cycloalkenyl or cycloalkynyl), residue of a spiro-compound or a terpene compound, or $R^{11}$ and $R^{13}$ may represent a single bond to thereby form —C≡C—, or $R^{12}$ and $R^{14}$ may form, together with —C=C—, an alicyclic ring.

The hydrocarbon residue for the groups $R^{11}$ to $R^{14}$ may be substituted with one or more hydrocarbon residues as mentioned above and/or one or more functional groups, as long as the addition reaction of the double or triple bond of the compounds of the formula (V) is not adversely affected. Typical examples of such functional groups are halogen atom, or amino, carboxyl, sulfo, mercapto, epoxy, cyano, nitro, hydroxy, alkoxy, alkoxy carbonyl, acyl, acyloxy, quaternary ammonium or polyalkylene ether group. The hydrocarbon residue for the groups $R^{11}$ to $R^{14}$ may contain a residue of, for example, a UV absorber or colorant.

The unsaturated hydrocarbon compound preferably used in the addition reaction is an alkene or alkyne having at least one unsaturated bond (double or triple bond) at the terminal or any position, for example, acetylene, ethylene, propylene, butene, octene, decene, or octadecene. The above alkene or alkyne may carry thereon a cyclic structure such as cyclohexane, benzene, naphthalene and the like. Further, the compound having plural double bonds such as butadiene, isoprene may be used.

The addition reaction can be carried out by bringing the powder material after the first stage treatment into contact with the Si—H reactive compound in a vapor, liquid or solid phase in the presence of a catalyst for 1 hour or more at 300° C. or less, preferably 0°–250° C.

A suitable catalyst is a platinum group catalyst such as a ruthenium, rhodium, palladium, osmium, iridium, or platinum compound. Preferably, a palladium or platinum compound is used. As the palladium catalyst, there may be mentioned palladium (II) chloride, palladium (II) oxide, palladium (II) hydroxide, etc. As the platinum catalyst, there may be mentioned platinum (II) chloride, tetrachloroplatinic acid, platinum (IV) chloride, hexachloroplatinic acid, hexachloroplatinic acid ammonium salt, platinum (II) oxide, platinum (II) hydroxide, platinum (IV) dioxide, platinum (IV) oxide, platinum (IV) disulfide, platinum (IV) sulfide, potassium hexachloroplatinate (IV), etc. Further, an organic solvent layer prepared by adding tri-$C_{1-8}$-alkylmethylammonium chloride and tri-$C_{1-8}$-alkylamine to the palladium or platinum compound and then extracting ion pairs in an aqueous/organic phase may be used. Furthermore, an amine catalyst such as tributylamine or a polymerization initiator may be used. The addition reaction can be carried out by employing UV rays, gamma-rays, plasma or the like.

Although the amount of the silicone polymer with the pendant group may be widely varied depending upon the purpose of the modification, the amount of the polymer with the pendant group is preferably 0.005% to 95% by weight based on the weight of the modified powder material.

The addition reaction performed in the second stage of the modification of the present invention brings about various advantages.

For example, the Si—H moieties present in the polymer film coating the powder material can be eliminated by carrying out the addition reaction of the Si—H reactive compound to the Si—H moieties. Thus, the unpreferable generation of hydrogen due to a coexisting $H_2O$ or alcohol can be prevented. Therefore, the resultant powder material can be formulated into an emulsion system without causing, for example, a color separation, because the surface property of the material is uniform.

Further, the modified powder material having various functions can be obtained by appropriately selecting the Si—H reactive compound and introducing the desired pendant group.

For example, the dispersibility of the modified powder material in a given oil can be controlled by adjusting the number of the carbon atoms contained in the pendant group. For example, the modified powder material coated with the film of the silicone polymer carrying $C_{18}$-pendant groups is dispersed excellently in a nonpolar oil such as a liquid paraffin, but poorly in a polar oil such as a castor oil. If the pendant group is a relatively short hydrocarbon chain such as a $C_5$-chain, the dispersibility in a polar oil is good. In the present invention, therefore, the powder material having an optimum dispersibility in a given oil can be obtained.

For example, the dispersibility of the powder material having a property to cut off UV rays (e.g., titanium dioxide) can be improved in a given system to enhance the efficiency of cutting off UV rays in the system. Further, magnetic characteristics of a magnetic recording element can be enhanced by improving the dispersibility of the magnetic powder material in a film of the element.

A hydrophilic property can be imparted to the powder material by introducing the pendant group having an alkylene oxide, amino or carboxyl terminal group. Further, an enzyme or the like can be bonded by a peptide bond to said amino or carboxyl group. Therefore, such a powder material can be used as a carrier for an immobilized enzyme. If a magnetic powder material is used as the core powder, a powder material having a magnetic property and an enzymic activity can be obtained.

By introducing a pendant group having a quaternary ammonium group, a powder material having an antibacterial property can be obtained. Further, a powder material having a desired color or UV absorbability can be produced by introducing a pendant group having a residue of a colorant or UV absorber at the end thereof.

As mentioned above, according to the present invention, various kinds of powder (or particulate) materials can be modified by coating the surfaces thereof with a silicone polymer film, followed by addition reaction with the Si—H reactive compound. Typical examples of such powder materials will now be explained below.

INORGANIC PIGMENT

Examples of the inorganic pigments capable of being modified according to the present invention are ultramarine blue, prussian blue, manganese violet, titanium-coated mice, bismuth oxychloride, iron oxides, iron hydroxide, titanium dioxide, titanium lower oxides, and chromium hydroxide. Of these pigments, ultramarine blue and prussian blue are typically modified according to the present invention.

As well-known in the art, ultramarine blue (e.g., sodium aluminum silicate containing sulfur) is generally represented by $Na_{6-9}Al_6Si_6O_{24}S_{2-4}$, and conventionally and widely used as a blue inorganic pigment in various fields (e.g., coating compositions, paints, inks, cosmetics, and detergents). Ultramarine blue has hydrophilicity and is stable up to a temperature of about 250° C. in an air atmosphere. However, ultramarine blue is not stable against an acid, although it is generally stable against an alkali. For example, ultramarine blue is gradually decomposed to generate hydrogen sulfide under an acidic condition (e.g., in the presence of a radical sulfate). As a result, the resultant ultramarine blue is discolored and becomes white. Obviously, the generation of hydrogen sulfide is especially not preferable in the fields of, for example, cosmetics. Furthermore, ultramarine blue is likely to generate hydrogen sulfide from a mechanical shearing force (e.g., grinding) or heating. Although various attempts have been made to obviate these disadvantages, as shown in Japanese Unexamined Patent Publication (Kokai) No. 54-95632 and Japanese Examined Patent Publication (Kokoku) No. 50-27483, the effects thereof are not sufficient from a practical point of view.

However, when ultramarine blue is modified according to the present invention, the generation of hydrogen sulfide under an acidic condition or at an elevated temperature or by a mechanical shearing force can be effectively prevented, and the decomposing action thereof against, for example, perfumes, can be suppressed. Thus, when the ultramarine blue modified according to the present invention is used under an acidic condition, no substantial deterioration occurs in aluminum or silver containers or in cosmetics. Furthermore, since the modified ultramarine blue is coated with the silicone polymer film with the pendant group, hydrophobicity is exhibited and the wettability is suppressed. Thus, the modified ultramarine blue can be formulated into an oil phase in an emulsion system. The modified ultramarine blue can prevent the unpreferable generation of hydrogen when incorporated in, for example, an aqueous or emulsion system.

The above-mentioned inherent disadvantages of ultramarine blue are believed to be caused by the presence of sulfur on the surfaces of ultramarine blue particles (i.e., surface sulfur). This surface sulfur is an active radical-type sulfur present on the surface of the crystalline lattice of ultramarine blue, which is likely to be susceptible to, for example, an acid, thermal, or mechanical shearing force action. However, according to the present invention, the surfaces of ultramarine blue particles are covered by the silicone polymer film carrying the pendant group to stabilize the ultramarine blue particles. Furthermore, since the silicone polymer film has a high transparency, there is no substantial difference between the unmodified and modified ultramarine blue particles. It should be noted, that, due to the presence of the above-mentioned active sites on the surfaces of the ultramarine blue particles, the silicone compound (I) deposited on the surfaces thereof (by the vapor phase treatment in the first stage of the present modification) can be polymerized at a temperature of, for example, 120° C. or less, to form a silicone polymer film having a crosslinked network structure. Note, the temperature may be raised to 200° C. After coating the active surface with the silicone polymer film, further adsorption and polymerization do not occur.

Ultramarine blue to be modified according to the present invention can be any conventional ultramarine blue particles having a size of, for example, 0.1 to 200 μm. The amount of the silicone polymer present in the modified ultramarine blue powder particle is typically about 0.1% to 20% by weight based on the weight of the modified particle, depending upon the surface area and activity of the particle. The ultramarine blue particles may be dried prior to the treatment, if desired. Furthermore, conventional composite powder particles of, for example, plastics or metal oxides coated with ultramarine blue, also can be treated according to the present invention.

As well-known in the art, prussian blue (i.e., ferri ferocyanide) is generally represented by $MFe(Fe(CN)_6)$, wherein M represents K, $NH_4$, or Na, and is conventionally and widely used as a blue inorganic pigment having a large coloring power in various fields (e.g., coating compositions, paints, cosmetics). However, prussian blue has a poor alkaline resistance, although the acid resistance is strong. Furthermore, prussian blue is not strong against heating, which causes decomposition or a discoloration to dark brown. Further, upon heating, prussian blue is susceptible to reduction and tends to cause a deterioration of co-existing substances (e.g., perfumes).

However, when prussian blue is modified according to the present invention, the above-mentioned disadvantages of conventional prussian blue can be effectively eliminated. Thus, the modified prussian blue is formulated into compositions such as cosmetics, pharmaceutical compositions, and the stability thereof is remarkably improved because an undesirable interaction thereof with other ingredients (e.g., perfumes) can be eliminated. Furthermore, since the silicone polymer film is highly transparent, no substantial difference is observed in color between the unmodified and the modified prussian blue particles. The modified prussian blue can prevent the unpreferable generation of hydrogen when incorporated in, for example, an aqueous or emulsion system.

The prussian blue powder particles to be modified according to the present invention can be any conventional prussian blue powder particles, preferably having a size of 0.01 to 200 μm. The amount of silicone polymer coated on the surface of the modified prussian blue particles is typically 0.5% to 50% by weight, depending upon the surface area of the particle.

METAL OXIDE AND HYDROXIDE

Examples of the metal oxides and hydroxides capable of being modified according to the present invention are magnesium oxide, magnesium hydroxide, calcium oxide, calcium hydroxides, aluminum oxide, aluminum hydroxide, silica, iron oxides ($\alpha$-$Fe_2O_3$, $\gamma$-$Fe_2O_3$, $Fe_3O_4$, FeO), iron hydroxides, titanium dioxide, titanium lower oxides, zirconium oxides, chromium oxides, chromium hydroxides, manganese oxides, cobalt oxides, nickel oxides, and zinc oxides. These oxides and hydroxides may be used alone or in any mixture thereof. Furthermore, composite oxides and composite hydroxides such as iron titanate, cobalt titanate, cobalt aluminate also can be used in the present invention. Composite materials comprising metal oxides or hydroxides coated on the core materials (e.g., titanium oxides coated mica, iron oxides coated nylon) also can be used in the present invention.

Although there are no critical limitations to the sizes of the metal oxide or hydroxide powder particles, metal oxides or hydroxides having a size of 0.001 μm to 10 mm can be preferably coated witn the silicone polymer film without causing agglomeration of the powder particles particularly in the first stage treatment. The preferable coating amount of the silicone polymer is 0.1% to 40% by weight, depending upon the kinds and surface area of the metal oxides or hydoroxides.

As well-known in the art, metal oxides and hydroxides are conventionally and widely used as, for example, a colorant in various application fields (e.g., coating compositions, paints, cosmetics, inks) or as a magnetic material. However, conventional metal oxides and hydroxides generally have hydrophilicity and, therefore, have a poor dispersibility thereof in oils or organic solvents. Furthermore, metal oxides and hydroxides have catalyst activities and, therefore, deteriorate co-existing substances such as fats and oils and perfumes or cause discoloration due to their surface activities.

On the other hand, when metal oxides and hydroxides are modified according to the present invention, the resultant metal oxides and hydroxides are uniformly covered with the silicone polymer film over the entire surfaces thereof and, therefore, the metal oxides and hydroxides are stabilized so that they do not interact with other agents and do not deteriorate perfumes and the like. Thus, when the modified metal oxides and hydroxides are formulated into various compositions (e.g., coating compositions, paints, cosmetics, pharmaceutical compositions), the stability thereof with the lapse of time is remarkably improved. Furthermore, since the silicone polymer film is very thin (e.g., 3 to 20 Å) and is transparent, a color difference between the untreated and treated metal oxides and hydroxides is not observed and the magnetic properties of the metal oxides and hydroxides, if any, are not adversely affected. Thus, the modified $\gamma$-$Fe_2O_3$ or Co-$\gamma$-$Fe_2O_3$ may be advantageously used in the production of magnetic recording materials. Further, the modified metal oxide or hydroxide can prevent the unpreferable generation of hydrogen when incorporated in, for example, an aqueous or emulsion system.

MICA

Examples of mica capable of being modified according to the present invention are muscovite, phlogopite, biotite, sericite, lepidolite, paragonite and artificial or synthetic mica having a fluorine atom substituted for the hydroxyl group of natural mica as well as baked or calcined products thereof. These mica may be used alone or in any mixture thereof.

Although raw mica ores may be modified according to the present invention, mica having a size of 0.5 to 200 μm may be preferably modified according to the present invention. However, mica can be modified according to the present invention after the cleaving thereof to a thin form (e.g., flakes). Although there are no critical limitations to the size of the mica, the preferable coating amount of the silicone polymer is 0.1% to 20% by weight, in the case of the inherent mica. However, when the excess amount of the silicone compound is introduced in the vapor or liquid phase treatment of the first stage, the mica is expanded due to the occurrence of the cleavage of the mica and, therefore, up to 20% to 95% by weight to the silicone polymer may be coated.

As well-known in the art, mica is conventionally and widely used as a filler or additive in, for example, coating compositions, inks, and cosmetics, as well as plastics and rubbers. However, mica generally has hydrophilicity and, therefore, has a poor dispersibility in oils and organic solvents. Furthermore, when mica is kneaded to plastics and rubbers, mica is likely to cause aggregation and uniform kneading is difficult.

On the other hand, when mica is modified according to the present invention, the modified mica is uniformly covered with the thin silicone polymer film over the entire surfaces thereof and, therefore, the mica is stabilized. Accordingly, when the modified mica is incorporated into compositions, the mica does not decompose or deteriorate co-existing substances (e.g., perfumes) and, therefore, the stability of the cosmetics and pharmaceutical compositions with the lapse of time is remarkably improved. Furthermore, since the silicone polymer film is thin and transparent, there are no substantial differences in color between the untreated and the modified mica. In addition, the modified mica exhibits hydrophobicity and can be formulated into an oil phase in the case of emulsions. Further, the modified mica can prevent the unpreferable generation of hydrogen when incorporated in, for example, an aqueous or emulsion system.

ORGANIC PIGMENT

Examples of the organic pigments capable of being modified according to the present invention are C.I. 15850, C.I. 15850: 1, C.I. 15585: 1, C.I. 15630, C.I. 15880: 1, C.I. 73360, C.I. 12085, C.I. 15865: 2, C.I. 12075, C.I. 21110, C.I. 21095, and C.I. 11680, C.I. 74160 and zirconium, barium, or aluminum lakes of C.I. 45430, C.I. 45410, C.I. 45100, C.I. 17200, C.I. 45380, C.I. 45190, C.I. 14700, C.I. 15510, C.I. 19140, C.I. 15985, C.I. 45350, C.I. 47005, C.I. 42053, C.I. 42090.

The surfaces of these organic pigments may be treated with, for example, resins. These organic pigments may be used alone or in any mixture thereof.

Although these are no critical limitations to the sizes of the organic pigments, the organic pigments having a size of 0.05 to 200 $\mu$m may be preferably coated or covered with the silicone polymer film. The preferable coating amount of the silicone polymer is 0.1% to 40% by weight, depending upon the kinds and surface area of the organic pigments.

As well-known in the art, organic pigments are conventionally and widely used as a colorant in, for example, coating compositions, inks, and cosmetics, as well as plastics and rubbers. However, conventional organic pigments or the surface-treated products thereof cause the decomposition or deterioration of coexisting substances when formulated into compositions due to the interaction thereof, based on the presence of the active sites on the surface thereof, with the coexisting substances. Furthermore, certain organic pigments cause discoloration due to, for example, the adsorption or desorption of the water of crystallization.

On the other hand, when organic pigments are modified according to the present invention, the modified organic pigments have a uniform silicone polymer film covering the entire surface thereof. Thus, the modified organic pigments become stable and have no interaction acitivities against the coexisting substances. Accordingly, when the modified organic pigments are formulated into compositions, the stability of the compositions with the lapse of time is remarkably improved. Furthermore, since the silicone polymer film is thin and highly transparent, there is no difference in the color of the organic pigments before and after the treatment. In addition, the dispersibility thereof in vehicles is also improved. Further, the modified organic pigment can prevent the unpreferable generation of hydrogen when incorporated in, for example, an aqueous or emulsion system.

PEARLING PIGMENT

Examples of pearling pigments (or nacreous pigments) are mica-titanium composite materials containing, as a titanium component, titanium dioxide, titanium lower oxides, titanium oxynitride, mica-iron oxide composite materials, bismuth oxychloride, and guanine. The mica-titanium composite materials may be mixed with colored pigments such as iron oxides, prussian blue, chromium oxide, carbon black, and carmine. These pearling pigments may be used alone or in any mixture thereof.

Although there are no critical limitations to the sizes of the pearling pigments, the pearling pigments having a size of 0.1 to 200 $\mu$m can be preferably coated or covered with the uniform silicone polymer film over the entire surface thereof. Note, in the case of the pearling pigments, the powder particles are preferably in the form of a flat shape (e.g., flakes). The preferable coating amount of the silicone powder is approximately 0.01% to 40% by weight.

As well-known in the art, pearling pigment are widely used in, for example, coating compositions, inks, cosmetics, plastics, ceramics, decorating, daily necessities, and fiber or textile products. Mica is generally formulated into these compositions, together with colored pigments, to exhibit a various by colored appearance. However, when mica composite materials are used together with other substances, the composite materials themselves are deteriorated or cause discoloration or deterioration of coexisting substances.

On the other hand, according to the present invention, when to pearling pigments are uniformly coated or covered with the silicone polymer film, the resultant pearling pigments are stabilized and do not cause deterioration or decomposition of the coexisting substances. Further, the modified pearling pigment can prevent the unpreferable generation of hydrogen when incorporated in, for example, an aqueous or emulsion system.

MINERAL SILICATE

Examples of the mineral silicates capable of being modified according to the present invention are phyllosilicates and tectosilicates such as pyrophyllite, talc, chlorite, chrysotile, antigorite, lizardite, kaolinite, dickite, nacrite, halloysite, montmorillonite, nontronite saponite, sauconite, and bentonite; natrolites such as natrolite, mesolite, scolecite, and thomsonite; heulandites such as heulandite, stilbite, epistibite; and zeolites such as analcite, harmotone, phillipsite, chabazite, and gmelinite. These silicate minerals may be used alone or in combination thereof. The phyllosilicates may have organic cations at the interface of the layers thereof or may be substituted with alkali metal or alkaline earth metal ions. The tectosilicates may include metallic ions in the fine pores thereof.

Although there are no critical limitations to the sizes of the silicate mineral particles, preferably silicate mineral particles having a size of 0.01 $\mu$m to 10 mm are modified according to the present invention. The preferable coating amount of the silicone polymer is 0.1% to 40% by weight, depending upon the kinds and surface area of the silicate mineral particles.

As well-known in the art, conventional silicate minerals optionally coated with certain silicone resins are widely used as an electric insulating material, filler, and additives in various fields (e.g., pharmaceutical compositions, ceramics, paper, rubbers, inks, cosmetics, and coating compositions). However, conventional silicate minerals unpreferably cause a deterioration of coexisting substances (e.g., perfumes, oils and fats, resins) when formulated into, for example, cosmetics and coating compositions.

On the other hand, according to the present invention, the silicate minerals can be stabilized because the surfaces of the silicate mineral particles can be uniformly coated or covered with a thin silicone polymer film. As a result, the modified silicate minerals do not deteriorate the coexisting substances when formulated therewith into compositions. Further, the modified silicate minerals can prevent the unpreferable generation of hydrogen when incorporated in, for example, an aqueous or emulsion system.

POROUS MATERIAL

Examples of the porous materials capable of being modified according to the present invention are the above-mentioned silicate minerals; the above-mentioned mica; the above-mentioned metal oxides; $KAl_2(Al, Si_3)O_{10}F_2$, $KMg(Al, Si_3)O_{10}F_2$, and $K(Mg, Fe_3)(Al, Si_3)O_{10}F_2$; carbonate minerals such as $CaCo_3$, $MgCO_3$, $FeCO_3$, $MnCO_3$, $ZnCO_3$, $CaMg(CO_3)_2$, $Cu(OH)_2CO_3$, and $Cu_3(OH)_2(CO_3)_2$; sulfate minerals such as $BaSO_4$, $SrSO_4$, $PbSO_4$, $CaSO_4$, $CaSO_4.2H_2O$, $CaSO_4 \cdot 5H_2O$, $Cu_4SO_4(OH)_6$, $KAl_3(OH)_6(SO_4)_2$, and $KFe_3(OH)_6(SO_4)_2$; phosphate minerals such as $YPO_4$, $(Ce, La)PO_4$, $Fe_3(PO_4)_2.8H_2O$, $Ca_5(PO_4)_3OH$, and $Ca_5(PO_4, CO_3OH)_3(F, OH)$; and metal nitrides such as titanium nitride, boron nitride, and chromium nitride. These materials may be used alone or in any mixture thereof. Furthermore these porous materials may be modified after granulation or molding, followed by banking or calcining. Furthermore, celluloses, fibers, and synthetic resins may be modified with the silicone compounds according to the present invention.

Although there are no critical limitations to the sizes of the porous materials, the porous materials having a size of 10 mm or less, more preferably 3 $\mu$m to 10 mm, may be preferably coated with the silicone polymer film. The preferable coating amount of the silicone polymer is approximately 0.01 to 60% by weight, depending upon the kinds and surface areas of the porous materials.

The porous material should be brought into contact with the silicone compound in the form of a vapor in the first stage of the modification according to the present invention. According to the present invention, the silicone compound deposited on the surface of the porous material is polymerized due to the presence of the active sites on the surface of the porous material and on the surface of the micropores of the porous material, whereby the entire surfaces of the porous material are coated with the silicone polymer in which the surface activity has disappeared. Thus, the modified porous materials do not cause a deterioration of substances such as pharmaceutical agents and perfumes. Accordingly, the modified porous materials may be advantageously used in, for example, perfumes, pharmaceutical compositions, toys, artificial organs, artificial bones, and ceramics. Further, the modified porous material can prevent the unpreferable generation of hydrogen when incorporated in, for example, an aqueous or emulsion system.

CARBONS

Examples of the carbons capable of being modified according to the present invention are the activated carbon and carbon black conventionally used in, for example, coating compositions, inks, tires, and cosmetics.

Although there are not critical limitations to the sizes of the carbon powder particles, preferably carbon powder particles having a size of 0.001 $\mu$m to 10 mm are modified according to the present invention. The preferable coating amount of the silicone polymer is approximately 0.1 to 80% by weight, depending upon the kinds of surface areas of the carbon powder particles.

As well-known in the art, carbon powder particles are widely used as a colorant in, for example, coating compositions, inksm and cosmetics. However, since carbon is generally hydrophilic, the dispersibility thereof in oils and organic solvents is not good. Furthermore, carbon tends to deteriorate coexisting substances such as oil and fats and perfumes and to adsorb valuable agents thereon.

On the other hand, according to the present invention, the surface of the carbon powder particles is covered with a uniform silicone polymer film. As a result, the surface activity of the carbon disappears, and the modified carbon becomes hydrophobic or lipophilic. Accordingly, the modified carbon may be advantageously formulated into, for example, coating compositions, inks, and cosmetics, without causing any deterioration of coexisting substances such as oil and fats and perfumes. Further, the modified carbon can prevent the unpreferable generation of hydrogen when incorporated in, for example, an aqueous or emulsion system.

METALS

Examples of the metals capable of being modified according to the present invention are iron, cobalt, nickel, copper, zinc, aluminum, chromium, titanium, zirconium, molybdenum, silver, indium, tin, antimony, tungsten, platinum, and gold, and the alloys thereof. When metals are coated with the silicone polymer film with the pendant group according to the present invention, the metals become stable (i.e., do not cause autooxidation upon contact with oxygen) and the dispersibility thereof is remarkably improved. Further, the modified metals can prevent the unpreferable generation of hydrogen when incorporated in, for example, an aqueous or emulsion system.

Accordingly, the modified metals can be advantageously used in, for example, magnetic recording materials.

Although there are no critical limitations to the sizes of the metals, the metals typically having a size of 0.01 $\mu$m to 10 mm may be preferably modified. The preferable coating amount of the silicone polymer is approximately 0.01 to 20% by weight.

BIOPOLYMER

Powdery biopolymer materials are widely utilized in the fields of pharmaceuticals, cosmetics or the like, by virtue of their high safety factor. However, hydrophilic groups such as hydroxyl, amino or carboxyl groups are exposed on the surfaces thereof, and thus the dispersibility is low in an oil system. The powdery biopolymer materials have relatively high dispersibility in an aqueous or emulsion system. But, if the materials are incorporated in compositions for a long term, conformations thereof are transformed by the action of coexisting water, or such compositions become moldy. Therefore, such materials cause safety problems such as denaturation, color change, or odor change of the composition.

Hitherto, biopolyer materials have been incorporated in pharmaceutical or cosmetic compositions only after being finely divided, as disclosed in Japanese Unexamined Patent Publication (Kokai) Nos. 55-27120 and 54-70435. Therefore, such disadvantages have not been substantially eliminated.

The biopolymer powder material modified according to the present invention has a good dispersibility in an oil or emulsion system. Further, the stability is remarkably improved, because the silicone polymer film and hydrophobic pendant groups thereon can prevent water from permeating and coming into contact with the core material. Therefore, the biopolymer material modified according to the present invention exhibits a remarkably improved stability in a pharmaceutical or cosmetic composition.

Examples of biopolymer materials which may be modified according to the present invention are keratin (hair, fur, feather, down, horn, hoof, etc.), fibroin (silk), collagen (skin, hide, leather, tendon, bone, etc.), cellulose, hemicellulose, pectin, chitin, chondroitin, peptideglucan, nucleic acid (DNA, RNA), and the like.

Although there are no critical limitations to the sizes of the biopolymer powder particles, biopolymer materials having a size of 0.01 $\mu$m to 10 mm can be preferably coated with the silicone polymer film having the pendant group. The preferable coating amount of the silicone polymer is 0.01% to 40% by weight, depending upon the kinds and surface areas of the biopolymer materials.

The powdery biopolymer material modified according to the present invention may be utilized in pharmaceuticals, cosmetics, coatings, and inks.

The modified powder or particulate materials according to the present invention can be advantageously formulated as, for example, pigments, into any coating compositions including, for example, solvent-type powder-type, emulsion-type, and aqueous-type coating compositions. Coating compositions generally contain resins, pigments, solvents, plasticizers, and other conventional additives as complicated multiple component mixtures. For example, pigments are formulated into coating composition (i) to provide, to the coating film, color; a hiding powder; physical characteristics (e.g., hardness, strength, adhesiveness); and improved weather resistance; fluorescence, phosphorescence, magnetic properties, electric conductivity, and similar inherent characteristics of the pigments, (ii) to improve the flowability of the coating composition and the workability during coating, and (iii) to prevent the generation of rust, fungal growth, and injurious organisms. For these reasons, the compatibility of pigments with resins or dispersants has been studied. Pigments have various properties, for example, from hydrophilic properties to hydrophobic properties and cause color separation and other undesirable phenomena in the resultant coating compositions. When the modified pigments according to the present invention are formulated into coating compositions, the unpreferable color separation does not occur because the surfaces of the modified pigments are uniformly and entirely covered with the silicone polymer film. In addition, since the surface activities of the pigments are seal-coated with the silicone polymer film, the deterioration of the coated film with the lapse of time can be effectively prevented. Furthermore, since the silicone polymer film coated on the surface of the modified pigment is very thin and transparent, the color of the modified pigment is not substantially changed when compared to the untreated pigment. Accordingly, color correction is not required after the modification. Typical examples of resin vehicles usable in the coating compositions according to the present invention are those conventionally used, such as, nitrocelluloses, oil modified alkyd resins, melamine resins, polyamide resins, epoxy resins, and unsaturated polyester resins.

The modified powder or particulate materials according to the present invention can be advantageously formulated as additives in cosmetic compositions. Typical examples of such additives are the above-mentioned inorganic pigments, metallic oxides and hydroxides, mica, organic pigments, pearling pigments, mineral silicates, carbons, metals, biopolymers and composite materials. When the unmodified powder materials are formulated into cosmetic compositions, perfumes contained in the cosmetic compositions are sometimes deteriorated or denatured due to the surface activities of these materials. As a result, the odor beomes worse. Contrary to this, when the modified powder materials according to the present invention are formulated into cosmetic compositions, these problems can be effectively solved since the surface activities are made to disappear by coating the entire surface of the powder materials with the silicone polymer film.

According to the present invention, the modified powder material coated with the silicone polymer having the pendant group can prevent the unpreferably generation of hydrogen from Si—H moieties, even if incorporated in an aqueous or emulsion system.

Further, according to the present invention, the modified powder material having a high liopophilicity (or hydrophobicity) can be advantageously prepared by providing a water repellency to the powder material through the introduction of a pendant group, for example, of a long-chain alkyl group. Furthermore, the modified powder material having a high hydrophilicity can be advantageously prepared by introducing a pendant group, for example, or an alkylene oxide or carboxyl group. Therefore, the modified powder material according to the present invention has an extremely improved dispersibility in a medium and, therefore, when the modified ultrafine titanium dioxide is formulated into, for example, sunscreen preparations, the UV rays cut-off efficiency is increased 3 to 4 times, when compared to conventional ultrafine titanium dioxide, due to the high dispersibility thereof.

The modified powder materials according to the present invention can be formulated into any conventional cosmetic compositions including, for example, creams, liquid creams, packs, cosmetic powders, foundations, lipsticks, rouges, manicure preparation (e.g., nail polishes, nail enamels, enamel removers, nail treatments), eye cosmetics (e.g., eye liners, eye shadows), sunscreen preparations, deodorant preparations, shampoos, rinses, and hair treatments.

Any conventional cosmetic ingredients can be used, together with the modified powder materials. Typical examples of such ingredients are various hydrocarbons such as squalane, liquid paraffin, vaseline, microcrystalline wax, selecine, myristic acid, palmitic acid, stearic acid, oleic acid, isostearic acid, cetyl alcohol, hexadecyl alcohol, oleyl alcohol, cetyl-2-ethylhexanote, 2-ethylhexyl palmitate, 2-octyldodecyl myristate, 2-octyldodecyl gum ester, neopentyl glycol-2-ethylhexanate, isooctyl triglyceride, 2-octyldodecyl oleate, isopropyl myristate, isostearic acid triglycerides, coconut oil fatty acid triglyceride, olive oil, avocado oil, beeswax, myristyl myristate, mink oil, lanolin, and dimehtyl polysiloxane; oils such as higher fatty acids, oils and fats, esters, higher alcohols, waxes, and silicone oils; organic solvents such as acetone, toluene, butyl acetate, and etyl acetate; resins such as alkyd resins and urea resins; plasticizers such as camphor and acetyl tributyl citrate; UV absorbers; anti-oxidants; preservatives; surfactants; humectants; perfumes; water; alcohols; and thickening

EXAMPLE

The present invention will now be further illustrated by, but is by no means limited to, the following Examples and Comparative Examples, wherein all parts and percentages are on a weight basis unless otherwise specified.

EXAMPLE 1-1

In a desiccator, 10 g of yellow iron oxide contained in a 200 ml beaker and 5 g of tetramethyl tetrahydrogen cyclotetrasiloxane contained in a 20 ml sample tube were placed and allowed to stand at 50° C. After one day, the treated powder was taken out of the desiccator and allowed to stand at 50° C. for 3 hours to give 10.185 g of the product modified by the first stage treatment in the modification according to the present invention.

Into a 100 ml eggplant-shape flask, 5 g of the resultant yellow iron oxide was taken. Thereafter, 5 mg of chloroplatinic acid, 5 ml of 1-tetradecene and 30 ml of isopropanol were added thereto and the whole was heated under reflux in a water bath for 5 hours. Then, the filtration with a filter (G-4) and the washing with 50 ml of chloroform were carried out, and the powder was dried in a thermostatic chamber at 90° C. for 1 hours to yield the modified powder material.

COMPARATIVE EXAMPLE 1-1

To 10 g of yellow iron oxide was added 25 g of a hexane solution containing 0.185 g of tetramethyl tetrahydrogen cyclotetrasiloxane, and after stirring well, the mixture was evaporated to dryness. Then, baking was carried out at 250° C., whereby the product became discolored to red.

COMPARATIVE EXAMPLE 1-2

A 10 g amount of yellow iron oxide and 0.019 g of calcium hydroxide were charged in a ball mill and mixed and ground for 30 minutes. Then, 0.185 g of hydrogen methyl polysiloxane (molecular weight=2600) was added, followed by mixing and grinding for 30 minutes. Next, 0.076 g of myristic acid was added and the mixture was ground for 30 minutes to give a treated product.

Each of the yellow iron oxides of Example 1-1, Comparative Example 1-1, Comparative Example 1-2, and the untreated sample was subjected to colorimetry, and measurements of water repellency, specific volume, and test of hydrogen generation, and the behaviors of the decomposition of linalool were made by a microreactor.

COLORIMETRY

A sample was filled in a cell for measurement of the powder, and the measurement was conducted within the range of from 380 mn to 780 nm by a Hitachi Color Analyzer Model 607. The colorimetric results are represented in L, a and b, and the color difference $\Delta E$ calculated as shown in Table 1-1. It can be appreciated that the color difference $\Delta E$ of Example 1-1 is remarkably smaller than those of the Comparative Examples.

WATER REPELLENCY

A sample tube of 10 ml is charged with 5 ml of deionized water and with 0.1 g of powder and then subjected to shaking. The judgement was conducted as follows.
x: dispersed in water.
Δ: water repellent but partially dispersed in water.
O: water repellent, and floated on the surface of the water.

The results are shown in Table 1-1. The untreated yellow iron oxide was well dispersed in water, Example 1-1 and Comparative Example 1-2 were water repellent and floated on the water, but Comparative Example 1-1 was partially dispersed in water due to incomplete treatment.

SPECIFIC VOLUME

A test tube for tapping specific volume was charged with 5 g of powder, and the specific volume was determined by repeating the tapping 200 times. The results are shown in Table 1-1.

It can be seen that Comparative Example 1-2 is agglomerated to a smaller specific volume by use of a ball mill. Also in Comparative Example 1-1, slight agglomeration occurred, and this may be considered to be due to evaporation of the solvent. In contrast, no agglomeration occurred in Example 1-1 due to vapor phase treatment, and the specific volume did not change from that before treatment.

DECOMPOSITION OF LINALOOL BY MICROREACTOR

In a Pyrex glass tube of 4 mm inner diameter, 20 mg of powder was fixed with quartz wool, and a decomposition measurement of linalool, which is a fragrant component, was carried out at a reaction temperature of 180° C. The amount of linalool injected was 0.3 μl, and nitrogen was used as the carrier gas at a flow rate of 50 ml/min.

Analysis was conducted by Shimazu GC-7A with the use of a column of 5% FFAP/chromosorb w 80/100, 3 mm×3 m at a column temperature of 80° C. (4 min-)–220° C. at a temperature elevation speed of 5° C./min.

In the linalool decomposition activity shown in Table 1-1, untreated powder is shown by Δ, stronger activity than that of untreated powder by x, and weaker activity by o.

When the results in Table 1-1 are judged comprehensively, it can be seen that Example 1-1 has become water repellent with substantially the same color and specific volume as the untreated powder. Further, the perfume stability is improved, and it may be considered to be an excellent modified powder when formulated in cosmetics, etc.

HYDROGEN GENERATION

A 50 ml dropping funnel and a hydrogen detector tube (Gastec Suiso: Kitazawa Sangyo) were attached to a 100 ml three-necked round flask equipped with a magnetic stirrer. The hydrogen detector tube was connected to a water jet pump and the generating hydrogen gas was continuously sucked under a constant reduced pressure.

The test of hydrogen generation was conducted using the above apparatus.

Into the above three-necked round flask, 1.0 g of a sample was charged and homogeneously dispersed in 5 ml of methanol. Then, 3 ml of 2N NaOH was pured through the funnel and stirred with the magnetic stirrer. The hydrogen detector tube is rendered black with the hydrogen gas generated by the alkali. The amount of the hydrogen generation was evaluated in accordance with the blackening degree of the hydrogen detector tube as follows:
o : not blackened
Δ: slightly blackened
x: blackened

TABLE 1-1

|  | Color | | | Color difference ΔE | Water repellency | Specific volume (ml/g) | Linalool decomposition activity | Hydrogen generation |
| --- | --- | --- | --- | --- | --- | --- | --- | --- |
|  | L | a | b |  |  |  |  |  |
| Yellow iron oxide (untreated) | 62.32 | 7.43 | 31.45 | — | X | 2.4 | Δ | O |
| Example 1-1 | 60.98 | 7.87 | 33.21 | 2.25 | O | 2.3 | O | O |
| Comparative Example 1-1 | 36.54 | 25.95 | 17.57 | 34.6 | Δ | 2.2 | X | Δ |
| Comparative Example 1-2 | 41.44 | 5.09 | 16.36 | 25.8 | O | 0.6 | X | X |

EXAMPLE 1-2

In a gas sterilizer kapokalizer CL-30B (Fuji Electric Co. Ltd.), 100 g of aluminum lake of C.I. 15985 and 50 g of trimethyl trihydrogen cyclotrisiloxane contained in separate vessels were placed and the inner pressure in the gas sterilizer was reduced to 100 mmHg by an aspirator, and the temperature was maintained at 30° C.

Six hours later, the inner pressure was returned to atmospheric by introducing air, followed by repeating the evacuation several times, to obtain 128 g of the treated powder.

Into a 500 ml eggplant-shape flask, 50 g of the resultant aluminum lake of C.I. 15985 was taken. Thereafter, 50 mg of chloroplatinic acid, 50 ml of 1-tetradecene and 200 ml of isopropanol were added thereto and the whole was heated under reflux in a water bath for 5 hours. Then, the filtration with a glass filter (G-4) and the washing with 500 ml of chloroform were carried out, and the powder was dried in a thermostatic chamber at 90° C. for 1 hour to yield the modified powder material. The resulting powder exhibited a remarkable hydrophobicity and the linalool decomposing ability disappeared. In the test of hydrogen generation, no hydrogen was detected.

EXAMPLE 1-3

In a desiccator, 10 g of prussian blue and 10 g tetramethyl tetrahydrogen cyclotetrasiloxane contained in separate vessels were left to stand at 100° C. for 6 hours. Then, after drying at 100° C. for 2 hours, 13.3 g of powder modified by the first stage treatment was obtained.

Into a 100 eggplant-shape flask, 5 g of the resultant prussian blue was taken. Thereafter, 5 mg of chloroplatinic acid, 5 ml of 1-tetradecane and 30 ml of isopropanol were added thereto and the whole was heated under reflux in a water bath for 5 hours. Then, the filtration with a glass filter (G-4) and the washing with 50 ml of chloroform were carried out, and the powder was dried in a thermostatic chamber at 90° C. for 1 hours to yield the modified powder material. The resulting powder exhibited a remarkable hydrophobicity and the linalool decomposing ability disappeared. In the test of hydrogen generation, no hydrogen was detected.

EXAMPLE 1-4

Into a rotary double cone type reactor of 100 liter volume (made of stainless steel, equipped with a lagging jacket), 20 kg of titanium dioxide was charged, and 400 g of tetramethyl tetrahydrogen cyclotetrasiloxane was charged into a stock liquor feeding tank (made of stainless steel, equipped with a lagging jacket) directly connected by a stainless steel pipe to the reactor, and the system was reduced by a vacuum pump to 100 mmHg. The temperature of the system was maintained at 90° C. by feeding a heating medium heated at 90° C. from the heating medium heating tank by a circulation pump to the lagging jackets of the reactor and the stock liquor feeding tank. The reactor was rotated three times after being left to stand for 10 minutes by means of a timer, to thereby mix and stir the titanium dioxide within the reactor, which operation was repeated for 10 hours. Then, the inner pressure was returned to atmospheric by the introduction of $N_2$ gas and 20.3 kg of the treated powder was taken out. This was found to be entirely free from the agglomeration generally observed in untreated titanium dioxide, exhibited a good flow property and further, a marked hydrophobicity, with the linalool decomposing ability having disappeared.

10 g of the treated titanium dioxide and 1.0 g of 1-octene were homogeneously mixed, an argon gas was passed therethrough at the rate of 200 ml/min, and then a plasma radiation was carried out for 10 minutes at 30 W under a low frequency (5 KHz) by means of a plasma generator (Sankyo Dengyo K.K.). The resulting powder exhibited a remarkable hydrophobicity and the linalool decomposing ability disappeared. The absorption at 2170 $cm^{-1}$ due to the presence of the Si—H moiety disappeared. In the test of hydrogen generation, no hydrogen was detected.

EXAMPLE 2-1

(1) In a 100 ml two-necked flask, 10.0 g of yellow iron oxide was charged as a powder material. One inlet on the flask was connected to a 30 ml bubbler and the other inlet was connected to a trap cooled with a dry ice in acetone. The flask and the bubbler were allowed to stand at 90° C. for 3 hours on a constant-temperature bath. Then, 5 g of tetramethyl tetrahydrogen cyclotetrasiloxane was charged as a treating agent into the bubbler. Nitrogen was fed to the bubbler at a flow rate of 2.0 ml/min for 15 hours. Thereafter, the connections between the flask and the bubbler and between the flask and the trap were separated and the flask was allowed to stand at 50° C. for 3 hours. Thus, 10.2 g of the product modified by the first stage treatment was obtained.

(2) Into a 50 ml eggplant-shape flask, 5 g of the resultant yellow iron oxide was taken. Thereafter, 10 mg of chloroplatinic acid, 0.5 ml of 1-hexene and 30 ml of isopropanol were added thereto and the whole was heated under reflux in a water bath for 5 hours. Then, the filtration with a glass filter (G-4) and the washing with 100 ml of chloroform were carried out, and the powder was dried in a thermostatic chamber at 90° C. for 1 hours to yield the modified powder material.

The resultant powder of Example 2-1 was analyzed with respect to colorimetry, water repellency, specific volume and decomposition of linalool by microreactor and hydrogen generation, as in Example 1-1. The result is shown in Table 2-1.

TABLE 2-1

| | Color | | | Color difference ΔE | Water repellency | Specific volume (ml/g) | Linalool decomposition activity | Hydrogen generation |
|---|---|---|---|---|---|---|---|---|
| | L | a | b | | | | | |
| Yellow iron oxide (untreated) | 62.32 | 7.43 | 31.45 | — | X | 2.4 | Δ | — |
| Example 2-1 | 60.81 | 7.90 | 32.91 | 2.15 | O | 2.2 | O | O |

EXAMPLE 2-2

A 14.1 g amount of the powder material modified by the first stage treatment was obtained in the same manner as in Example 2-1(1), except that the flask and the bubbler were connected with a three-way cock and that nitrogen was fed at a flow rate of 4.0 ml/min.

Into a 100 ml eggplant-shape flask, 5 g of the resultant yellow iron oxide was taken. Thereafter, 5 mg of chloroplatinic acid, 5 ml of 1-octadecene and 30 ml of isopropanol were added thereto and the whole was heated under reflux in a water bath for 5 hours. Then, the filtration with a glass filter (G-4) and the washing with 50 ml of chloroform were carried out, and the powder was dried in a thermostatic chamber at 90° C. for 1 hour to yield the modified powder material. The resulting powder exhibited a remarkable hydrophobicity and the linalool decomposing ability disappeared. In the test of hydrogen generation, no hydrogen was detected.

EXAMPLE 2-3

Into a 100 liter rotary double cone type reactor (made of stainless steel, equipped with a lagging jacket), 20 kg of titanium dioxide was charged. The reactor was directly connected with a 10 liter treating agent feed vessel (made of stainless steel, equipped with a lagging jacket). A heating medium having a temperature of 90° C. was fed by a circulating pump to the jackets. A 1 liter amount of 1,3,5,7-tetramethyl cyclotetrasiloxane was added to the treating agent feed vessel and was then bubbled by introducing a nitrogen gas at a flow rate of 2 liters/min to the treating agent feed vessel. The reactor was provided with a condenser, where the unreacted treating agent was recovered while the nitrogen gas was discharged.

The reactor was rotated repeatedly for 1 minute at 10 minutes intervals, whereby the titanium dioxide was mixed within the reactor. The operation was repeated for 10 hours. Thus, 20.3 kg of the powder material modified by the first stage treatment was obtained.

Into a 500 ml eggplant-shape flask, 100 g of the resultant titanium dioxide was taken. Thereafter, 10 mg of chloroplatinic acid, 10 ml of 2-vinyl-naphthalene and 300 ml of chloroform were added thereto and the whole was heated under reflux in a water bath for 72 hours. Then, the filtration with a glass filter (G-4) and the washing with 500 ml of methanol were carried out, and the powder was dried in a thermostatic chamber at 90° C. for 1 hour to yield the modified powder material. The resulting powder exhibited a remarkable hydrophobicity and the linalool decomposing ability disappeared. In the test of hydrogen generation, no hydrogen was detected.

EXAMPLE 3-1

A 100 g amount of ultramarine blue powder and 20 g of tetrahydrogen tetramethyl cyclotetrasiloxane were separately charged into separate vessels, which were connected to each other in a closed relationship. The system was allowed to stand at room temperature for 96 hours. After 96 hours, 100.78 g of the treated ultramarine blue powder was obtained and was further allowed to stand at 50° C. for 24 hours in a dryer. Thus, 100.32 g of the treated ultramarine blue was obtained.

Into a 500 ml eggplant-shape flask, 50 g of the resultant ultramarine blue was taken. Thereafter, 50 mg of chloroplatinic acid, 5 ml of 1-tetradecene and 200 ml of isopropanol were added thereto and the whole was heated under reflux in a water bath for 5 hours. Then, the filtration with a glass filter (G-4) and the washing with 500 ml of chloroform were carried out, and the powder was dried in a thermostatic chamber at 90° C. for 1 hour to yield the modified powder material.

EXAMPLE 3-2

2 g of heptahydrogen heptamethyl cycloheptasiloxane was dissolved in 50 ml of chloroform, and 10 g of ultramarine blue powder was added thereto. After stirring well, the powder was dried at 80° C. to obtain 11.8 g of the ultramarine blue powder modified by the first stage treatment.

Into a 100 ml eggplant-shape flask, 5 g of the resultant ultramarine blue was taken. Thereafter, 0.5 mg of chloroplatinic acid, 0.5 ml of n-perfluorooctylethylene and 30 ml of chloroform were added thereto and the whole was heated under reflux in a water bath for 72 hours. Then, the filtration with a glass filter (G-4) and the washing with 50 ml of methanol were carried out, and the powder was dried in a thermostatic chamber at 90° C. for 1 hour to yield the modified powder material.

EXAMPLE 3-3

Into a centrifugal rotary ball mill, 100 g of nylon-12 fine powder (spherical, diameter of about 5 μm), and then 20 g of ultramarine blue and 500 g of alumina ball (diameter of 2 mm) were charged. The whole was stirred at 230 rpm for 5 hours. Further, 2 g of pentahydrogen pentamethyl cyclopentasiloxane was added and stirred for 3 hours to obtain of the ultramarine blue powder modified by the first stage treatment.

5 g of the resultant powder and 0.5 g of 1-tetradecene were homogeneously mixed. Then, a plasma radiation was carried out for 10 minutes at 20 W under a high frequency (13.56 MHz) by means of a plasma ashing apparatus LTA-4SN (Yanagimoto Seisakusho), while a nitrogen gas was passed therethrough so that the degree of vacuum was maintained at 1.0 mmHg. The resultant powder exhibited an excellent usability.

EXAMPLE 3-4

A 10 g amount of ultramarine blue powder and a mixed liquid of 1 g of tetrahydrogen tetramethyl cyclotetrasiloxane and 1 g of pentahydrogen pentamethyl cyclopentasiloxane were separately charged into separate vessels, which were connected to each other in a closed relationship. The system was allowed to stand at 90° C. for 24 hours. Then, the treated ultramarine blue was recovered and was allowed to stand at 90° C. for further 24 hours in a dryer. Thus, 10.13 g of the ultramarine blue powder modified by the first stage treatment was obtained.

Into a 100 ml eggplant-shape flask, 5 g of the resultant ultramarine blue was taken. Thereafter, 0.5 mg of chloroplatinic acid, 0.5 ml of 1-tetradecene and 30 ml of isopropanol were added thereto and the whole was heated under reflux in a water bath for 5 hours. Then, the filtration with a glass filter (G-4) and the washing with 50 ml of chloroform were carried out, and the powder was dried in a thermostatic chamber at 90° C. for 1 hour to yield the modified powder material.

The ultramarine blue powder obtained above was evaluated with respect to (i) the polymer structure, (ii) the chloroform-dissolution matter of the silicone polymer, (iii) the generation of hydrogen sulfide determined by a hydrogen sulfide detection method, (iv) the generation of hydrogen sulfide determined by silver plate blackening, (v) the linalool decomposition activity, and (vi) water repellency and (vii) hydrogen generation as follows.

(i) Silicone Polymer Structure

The value $100\ x/(x+y)$ in the silicone polymer $$(RSiO_{3/2})_x(RHSiO)_y$$

after the first stage treatment represents the crosslinking ratio(%) of the Si—H moiety.

A 100 mg amount of a sample and 900 mg of KBr powder were uniformly mixed and the mixture was placed in a cell for measuring diffusion reflection spectrum. Thus, the spectrum was determined by means of a Fourier transformation infrared spectrophotometer under the following conditions:

Resolving power: 1 cm$^{-1}$.
Integrating number: 100 (times).
Wavenumber range: 1300-1200 cm$^{-1}$.

The resultant spectrum was subjected to Kubelka-Munk function transformation by the attached computer software, followed by peak division according to a deconvolution method.

After the peak dividing, the spectrum showed peaks at 1261 cm$^{-1}$ and 1271 cm$^{-1}$. The peak at 1261 cm$^{-1}$ belonging to the methyl group of the unit $(RHSiO)_y$ and the peak at 1272 cm$^{-1}$ belonged to the unit $(RSiO_{3/2})_x$. Thus, the crosslinking ratio of the silicone polymer was determined from the following calculating equation:

$$\text{Crosslinking ratio} = \frac{ⓧ}{ⓧ + ⓨ} \times 100$$

wherein
ⓧ : peak height at 1272 cm$^{-1}$.
ⓨ : peak height at 1261 cm$^{-1}$.

When unsaturated hydrocarbon compounds such as alkene or alkyne are added to Si—H groups, the absorption at 2160 cm$^{-1}$ based on the presence of Si—H groups drops, whereas the absorption based on the presence of alkyl groups emerges freshly at 2800-3000 cm$^{-1}$. Therefore, the degree of the addition of alkene or alkyne to Si—H groups in the silicone polymer film can be obtained from the following equation:

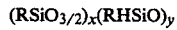

$$\text{ratio of addition} = 100 - \frac{\text{Si—H absorption intensity after reaction}}{\text{Si—H absorption intensity prior to reaction}} \times 100$$

(ii) Chloroform Soluble Matter

A 1-100 g amount of a sample was dispersed in 100-1000 ml of chloroform and, after filtration, the filtrate was concentrated in an evaporator. Then, the molecular weight was determined by means of gel permeation chromatography. The apparatus used was a Japan Analytical Industry Co., Ltd. LC-08 provided with three columns of B4H, B3H, and B3H.

The solvent used was chloroform (1.07 ml/min) and RI was used as a detector. The molecular weight was estimated from a calculation curve of standard polystyrene.

The ultramarine blue after the filtration was dried at 80° C. for 24 hours and used in the determination of the water repellency.

(iii) Determination of H$_2$S by H$_2$S Determination Method

A 200 ml three-necked round bottom flask with a magnetic stirrer was equipped with a 50 ml dropping funnel and a simple type gas detector, which was then connected to a tap aspirator so that the generated hydrogen sulfide gas was evacuated at a constant pressure. The hydrogen sulfide could be directly read from the graduation of 0.1% to 2.0%.

The determination was carried out by using this apparatus as follows. That is, 0.5 g of the ultramarine blue was charged into the three-necked round bottom flask and was uniformly dispered in 5 ml of deionized water. Then, 5 ml of 1N HCl was added through the funnel at one time, followed by stirring with the magnetic stirrer. The ultramarine blue was decomposed by the acid and the amount of the generated hydrogen sulfide(%) was read directly from the graduation.

(iv) Determination of H$_2$S by Silver Plate Blackening Test Method

The ultramarine blue sample and a silver plate were placed in a closed vessel at 80° C. for 2 days. The blackening degree of the silver plate was visually observed.

(v) Decomposition of Linalool by Microreactor In the same manner as in the Example 1-1.

(iv) Water Repellency

In the same manner as in the Example 1-1.
The results are as follows.

| Ex. No. | 100 X/(x + y) | Addition ratio (%) | Chloroform soluble | H$_2$S detection | Ag plate blackening | Linalool stability | Water repellency | Hydrogen generation |
|---|---|---|---|---|---|---|---|---|
| Example 3-1 | 44% | 100% | No*[1] | No*[2] | No change | Excellent*[3] | Good | O |
| Example 3-2 | 48% | 80% | No | No | No change | Excellent | Good | O |

-continued

| Ex. No. | 100 ×/(x + y) | Addition ratio (%) | Chloroform soluble | H2S detection | Ag plate blackening | Linalool stability | Water repellency | Hydrogen generation |
|---|---|---|---|---|---|---|---|---|
| Example 3-3 | 30% | 60% | No | No | Almost unchange | Good | Good | O |
| Example 3-4 | 73% | 100% | No | No | No change | Excellent | Good | O |

*[1] M.W. > 200,000
*[2] 1.0% for 10 minutes in the case of untreated ultramarine blue.
*[3] Decomposition occurred in the case of untreated ultramarine blue.

EXAMPLE 3-5

A 5 kg amount of ultramarine blue powder was charged into a 100 liter rotary double cone type reactor (made of stainless steel, equipped with a lagging jacket) and 500 g of a silicone compound having the following structure:

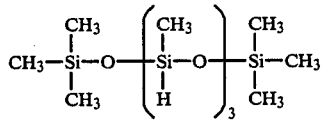

was charged into a stock liquor feeding tank (made of stainless steel, equipped with a lagging jacket) directly connected to the reactor by a stainless steel pipe. The system was evacuated to 20 mmHg by a vacuum pump. The temperature of the system was maintained at 90° C. by feeding a heating medium heated at 90° C. from the heating medium heating tank by a circulation pump to the lagging jackets of the reactor and the stock liquor feeding tank. The reactor was rotated three times after being allowed to stand for 10 minutes, by means of a timer, thereby to mix and stir the ultramarine blue within the reactor, which operation was repeated for 5 hours. Then, the inner pressure was returned to atmospheric by introducing N2 gas and 5.3 kg of the ultramarine blue modified by the first stage treatment was obtained.

100 g of the treated ultramarine blue was taken into a 1000 ml eggplant-shape flask, 5 ml of 1-octene and 400 ml of isopropyl alcohol containing 30 mg of chloroplatinic acid as a catalyst were added thereto, and the whole was heated under reflux in a water bath for 2 hours. Therefore, filtration was carried out using a milliporefilter (filter type VC, 0.1 nm). The powder was dried at 100° C. for 5 hours to yield 100.3 g of ultramarine blue powder covered with an alkyl-modified silicone polymer.

The treated powder material of Example 3-6 and untreated powder material were analyzed with respect to (i) the silicone polymer structure, (ii) dissolution with chloroform, (iii) water repllency, (iv) the linalool decomposition, and the like.

(i) Silicone Polymer Structure
In the same manner as in Examples 3-1 to 3-4.
(ii) Chloroform soluble Matter
In the same manner as in Examples 3-1 to 3-4.
(iii) Water Repellency
In the same manner as in Example 1-1.
(iv) Decomposition of Linalool by Microreactor
In the same manner as in Example 1-1.
(v) Determination of H2S by H2S Determination Method
In the same manner as in Examples 3-1 to 3-4.
(vi) Determination of H2S by Silver Plate Blackening Test Method
In the same manner as in Examples 3-1 to 3-4. The results are as follows.

| Ex. No. | 100×/(x + y) | Addition ratio (%) | Structure | Chloroform soluble | H2S detection | Ag plate blackening | Linalool stability | Water repellency |
|---|---|---|---|---|---|---|---|---|
| Example 3-5 | 80 | 100 | *1 | No*2 | No | No change | O | O |
| Untreated ultramarine blue | — | — | — | — | 1.0% (10 min) | All surface was brackened. | Δ | X |

*[1] [CH3SiO3/2]x[CH3(C8H17)SiO]y[(CH3)3SiO1/2]z (x:y:z = 42:18:40)
*[2] M.W. > 200,000

EXAMPLE 3-6

A 100 g amount of ultramarine blue powder was dispersed in 400 g of dichloromethane, and 3 g of methyl hydrogen polysiloxane (M.W.=ca. 3000) was added thereto. The whole was heated under reflux at 50° C. for 2 hours. After evaporating dichloromethane at 100° C., 1.0 g of styrene and 400 g of isopropyl alcohol containing 10 mg of chloroplatinic acid as a catalyst were added, and the whole was heated under reflux in a water bath for 2 hours. Thereafter, filtration was carried out using a glass filter, washing was performed with isopropyl alcohol, and the powder was dried at 80° C. The resultant modified powder, having a crosslinking ratio of 54% and an addition ratio of nearly 100%, exhibited a remarkable water repellency with the linalool decomposition ability having disappeared. Further, it showed excellent resistance to an acid and heat.

EXAMPLE 3-7

A 100 g amount of nylon-12 fine powder (spherical, diameter of about 5 nm) and 20 g of ultramarine blue powder were charged in a satellite ball mill, and mixed and ground for 5 hours. Then, 1 g of hydrogen methyl polysiloxane (molecular weight=6,000) was added, followed by mixing and grinding for 3 hours. Thereafter, 0.5 g of decosene and 10 mg of tri-n-octylmethylammonium chloroplatinate were added, followed by mixing and grinding for 2 hours.

The resultant modified powder, having a crosslinking ratio of 40% and an addition ratio of nearly 100%, exhibited a remarkable water repellency with the linalool decomposition ability having disappeared. Further, it showed excellent resistance to an acid and heat.

EXAMPLE 3-8

In a desiccator, 10 g of ultramarine blue powder and 5 g of tetrahydrogen tetramethyl cyclotetrasiloxane separately charged into separate vessels were allowed to stand at 80° C. After 48 hours, 10.18 g of the treated ultramarine blue powder was obtained and was further allowed to stand at 120° C. for 24 hours in a dryer. Thus, 10.12 g of the treated ultramarine blue was obtained. Then, 8 g of the resultant ultramarine blue powder was taken into a 100 eggplant-shape flask. 10 mg of tri-n-octylmethylammonium chloroplatinate as a catalyst, 10 ml of styrene and 50 ml of carbon tetrachloride were added thereto, and the whole was heated under reflux in a water bath for 2 hours. Then, filtration was carried out using a glass filter (G-4). Further, washing was performed with 300 ml of carbon tetrachloride. Thereafter, the powder was dried in a thermostatic chamber at 105° C. for 1 hour.

The resultant modified powder, having a crosslinking ratio of 52% and an addition ratio of nearly 100%, exhibited a remarkable water repellency with the linalool decomposition ability having disappeared. Further, it showed excellent resistance to an acid and heat.

EXAMPLE 3-9

A 100 g amount of potassium prussian blue and 50 g of tetrahydrogen tetramethyl cyclotetrasiloxane were separately charged into separate vessels, which were connected to each other in a closed system. The system was allowed to stand at 80° C. for 72 hours in a desiccator. Then, the prussian blue was taken out from the desiccator to obtain 132.3 g of the treated prussian blue. The resultant prussian blue was allowed to stand at 80° C. for further 24 hours in a dryer. Thus, 130.1 g of the prussian blue modified by the first stage treatment was obtained.

Into a 200 ml eggplant-shape flask, 20 g of the resultant powder material was taken. 10 mg of tri-n-octylmethylammonium chloroplatinate as a catalyst, 2 ml of octadecene and 100 ml of chloroform were added thereto, and the whole was heated under reflux in a water bath for 5 hours. Thereafter, filtration was carried out using a glass filter (G-4). Further, filtration and washing were performed with 100 ml of chloroform and then 150 ml of methyl alcohol. The powder was dried in a thermostatic chamber at 105° C. for 1 hour.

EXAMPLE 3-10

A 100 g amount of ammonium prussian blue and 50 g of trihydrogen pentamethyl cyclotetrasiloxane were separately changed into separate vessels, which were connected to each other in a closed system. The system was allowed to stand at 50° C. for 72 hours to obtain 125.3 g of the treated prussian blue. The treated prussian blue was allowed to stand at 80° C. for further 24 hours in a dryer. Thus, 124.3 g of the prussian blue modified by the first stage treatment was obtained.

Into a 500 ml eggplant-shape flask, 50 g of the resultant powder material was taken. 5 ml of 1-pentene and 300 ml of isopropyl alcohol containing 10 mg of chloroplatinic acid as a catalyst were added thereto, and the whole was heated under reflux in a water bath for 5 hours Thereafter, filtration was carried out using a glass filter (G-4). Further, filtration and washing was performed with 500 ml of isopropyl alcohol. The powder was dried in a thermostatic chamber at 105° C. for 1 hour.

EXAMPLE 3-11

A 5 kg amount of potassium prussian blue was charged into a 100 liter rotary double cone type reactor (made of stainless steel, equipped with a lagging jacket) and 500 g of a silicone compound having the following structure:

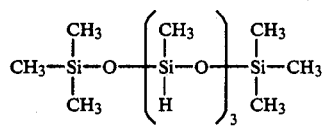

was charged into a stock liquor feeding tank (made of stainless steel, equipped with a lagging jacket) directly connected to the reactor by a stainless steel pipe. The system was evacuated to 20 mmHg by a vacuum pump. The temperature of the system was maintained at 90° C. by feeding a heating medium heated at 90° C. from the heating medium heating tank by a circulation pump to the lagging jackets of the reactor and the stock liquor feeding tank. The reactor was rotated three times after being allowed to stand for 10 minutes, by means of a timer, thereby to mix and stir the prussian blue within the reactor, which operation was repeated for 5 hours. Then, the inner pressure was returned to atmospheric by introduction of $N_2$ gas and 6.4 kg of the prussian blue modified by the first stage treatment was obtained.

Into a 1000 ml eggplant-shape flask, 100 g of the resultant powder material was taken. 5 ml of 1-octene and 400 ml of isopropyl alcohol containing 30 mg of chloroplatinic acid as a catalyst were added thereto, and the whole was heated under reflux in a water bath for 2 hours. Thereafter, filtration was carried out using a millipore filter (filter type VC, 0.1 μm). The powder was dried in a dryer at 100° C. for 5 hours to obtain prussian blue powder carrying an alkyl modified silicone polymer film.

The evaluation results are as follows.

| Ex. No. | $100 \times /(x+y)$ | Addition ratio (%) | Structure | Chloroform soluble | Linalool stability | Water repellency |
|---|---|---|---|---|---|---|
| Example 3-9 | 61 | 100 | *1 | No*4 | O*5 | O |
| Example 3-10 | 57 | 100 | *2 | No | O | O |
| Example | 64 | 100 | *3 | No | O*5 | O |

| Ex. No. | 100×/(x + y) | Addition ratio (%) | Structure | Chloroform soluble | Linalool stability | Water repellency |
|---|---|---|---|---|---|---|
| 3-11 | | | | | | |

*1 $[CH_3SiO_{3/2}]_x[(CH_3)(C_{18}H_{37})SiO]_y$ (x:y = 61:39)
*2 $[CH_3SiO_{3/2}]_x[(CH_3)C_5H_{11}SiO]_y[(CH_3)_3SiO_{1/2}]_z$ (x:y:z = 42.75:32.25:25)
*3 $[CH_3SiO_{3/2}]_x[(CH_3)(C_{18}H_{37})SiO]_y[(CH_3)_3SiO_{1/2}]_z$ (x:y:z = 51.2:28.8:20)
*4 M.W. > 200,000
*5 Untreated prussian blue powder decomposed linalool to myrcene, limonene, ocimene, alloocimene, α-terpinene, para-cymene and the like, whereas the treated powders of Examples 3-10 and 3-11 slightly decomposed linalool to form dehydrate such as myrcene and ocimene, not to form cyclized or isomefized products.

EXAMPLE 3-12

A 100 g amount of potassium prussian blue powder was dispersed in 400 g of dichloromethane, and 3 g of methyl hydrogen polysiloxane (M.W.=ca. 3000) was added thereto. The whole was heated under reflux at 50° C. for 2 hours. After evaporating dichloromethane at 100° C., 1.0 g of styrene and 400 g of isopropyl alcohol containing 10 mg of chloroplatinic acid as a catalyst were added, and the whole was heated under reflux in a water bath for 2 hours. Thereafter, filtration was carried out using a glass filter, washing was performed with isopropyl alcohol, and the powder was dried at 80° C. The resultant modified powder, having a crosslinking ratio of 63% and an addition ratio of nearly 100%, exhibited a water repellency with the linalool decomposition ability having disappeared.

EXAMPLE 3-13

A 20 g amount of ammonium prussian blue powder was charged in a satellite ball mill, and mixed and ground for 5 minutes. Then, 1 g of hydrogen methyl polysiloxane (molecular weight=6,000) was added, followed by mixing and grinding for 3 hours. Thereafter, 0.5 g of docosene and 10 mg of tri-n-octylmethylammonium chloroplatinate were used, followed by mixing and grinding for 2 hours.

The resultant modified powder, having a crosslinking ratio of 57% and an addition ratio of nearly 100%, exhibited a water repellency with the linalool decomposition ability having disappeared.

EXAMPLE 3-14

A 10 kg amount of ammonium prussian blue powder was charged into a 100 liter rotary double cone type reactor (made of stainless steel, equipped with a lagging jacket) and 3 kg of a silicone compound having the following structure:

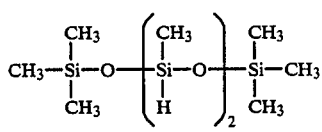

was charged into a stock liquor feeding tank (made of stainless steel, equipped with a lagging jacket) directly connected to the reactor by a stainless steel pipe. A nitrogen gas was introduced to the reactor, bubbling from the lower portion in the stock liquor feeding tank. The temperature of the system was maintained at 70° C. by feeding a heating medium heated at 70° C. from the heating medium heating tank by a circulation pump to the lagging jackets of the reactor and the stock liquor feeding tank. The reactor was rotated three times after being allowed to stand for 10 minutes, by means of a timer, thereby to mix and stir the prussian blue within the reactor, which operation was repeated for 7 hours. Then, the silicone compound was removed, rotation was carried out for 2 hours with introducing $N_2$ gas to the reactor. After the temperature was returned to a room temperature, 12.3 kg of the powder modified by the first stage treatment was obtained. Then, 1 kg of the resultant prussian blue powder was taken into a 5 l flask. 50 mg of tri-n-octylmethylammonium chloroplatinate as a catalyst, and 2 kg of 1-octadecene were added thereto, and the whole was heated under reflux by a mantle heater at 150° C. for 5 hours. Then, filtration was carried out using a glass filter (G-4). Further, washing was performed with 3 kg of chloroform and then 1.5 kg of methyl alcohol. Thereafter, the powder was dried in a thermostatic chamber at 105° C. for 1 hour. The resultant modified powder exhibited a remarkable water repellency.

EXAMPLE 4-1

A 10 g amount of yellow iron oxide powder and 5 g of tetrahydrogen tetramethyl cyclotetrasiloxane were separately charged into separate vessels, which were placed in a desiccator. The system was allowed to stand at 80° C. for 72 hours. After 72 hours, 10.50 g of the treated powder was obtained and was further allowed to stand at 50° C. for 24 hours in a dryer. thus, 10.20 g of the treated yellow iron oxide was obtained.

Into a 100 ml eggplant-shape flask, 5 g of the resultant yellow iron oxide powder material was taken. 10 mg of tri-n-octylmethylammonium chloroplatinate as a catalyst and 10 ml of 1-decene were added thereto, and the whole was heated under reflux in a water bath for 2 hours. Thereafter, filtration was carried out using a glass filter (G-4). Further, filtration and washing were performed with 100 ml of chloroform and then the powder was dried in a thermostatic chamber at 105° C. for 1 hour.

EXAMPLE 4-2

(1) A 100 g amount of finely divided titanium dioxide powder (0.025 μm) and 20 g of tetrahydrogen tetramethyl cyclotetrasiloxane were separately charged into separate vessels, which were connected to each other in a sealed system, followed by allowing to stand at room temperature for 96 hours. Thus, 107.85 g of the treated finely divided titanium dioxide powder was obtained. The resultant powder was then allowed to stand at 50° C. for a further 24 hours in a dryer. As a result, 104.80 g of the finely divided titanium dioxide powder modified by the first stage treatment was obtained.

(2) Into a 1000 ml eggplant-shape flask, 50 g of the resultant powder material was taken. 50 mg of tri-n-octylmethylammonium chloroplatinate as a catalyst, 50 ml of octadecene and 300 ml of chloroform were added thereto, and the whole was heated under reflux in a water bath for 5 hours. Thereafter, filtration was carried out using a glass filter (G-4). Further, filtration and washing were performed with 500 ml of chloroform and then 150 ml of methyl alcohol. The powder was dried in a thermostatic chamber at 105° C. for 1 hour.

(3) A modified titanium dioxide was obtained in the same manner as in Example 4-2(2), except that 1-pentene was used in place of octadecene as an unsaturated hydrocarbon compound.

(4) Each of the titanium dioxide powder materials obtained in Example 4-2(1) [sample (b)], Example 4-2(2) [sample (c)], and Example 4-2(3) [sample (d)], and the untreated titanium dioxide [sample (a)] was evaluated with respect to dispersibility. As a pendant group, sample (c) has $C_{18}$-alkyl groups and sample (d) has $C_5$-alkyl groups, respectively.

Each of the samples (a) to (d) was added in an amount of 5% by weight into each of liquid paraffin and castor oil, kneaded by passing several times through a three-roll mill, and coated on a silica glass in a thickness of 5 μm by means of an applicator. An absorption spectrum was measured at 280 to 700 nm by a spectrophotometer 340 (Hitachi).

Figure 2:
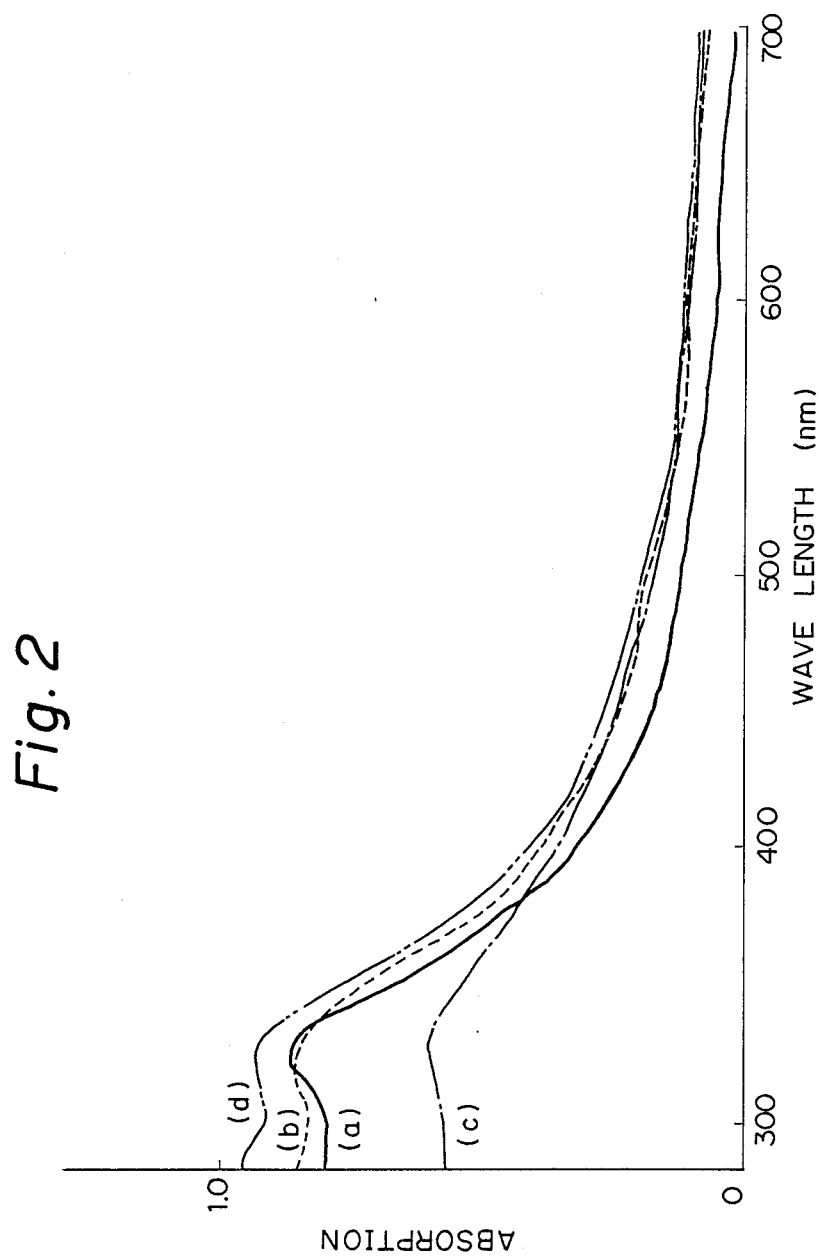

FIGS. 1 and 2 show UV absorption curves of the samples (a) to (d) dispersed in liquid paraffin and castor oil, respectively. Referring to FIG. 1, a UV absorption intensity around 320 nm of the sample (c) [having $C_{18}$-pendant groups] is three to four times higher than that of the sample (a) [untreated]. Those of the sample (b) [having no pendant group] and the sample (d) [having $C_5$-pendant groups] are higher than that of the sample (a), but lower than that of the sample (c). In a non-polar oil, a modified powder material having long pendant groups (e.g., $C_{18}$-alkyl) can be properly dispersed.

Referring to FIG. 2, a UV absorption intensity of the sample (c) is lower than that of the sample (a), whereas such an intensity of the sample (d) is higher than that of the sample (a). Therefore, it is apparent that, in a polar oil, a modified powder material having relatively short pendant groups (e.g., $C_5$-alkyl) can be more dispersed than that having long pendant groups.

As shown above, a most suitable pendant alkyl group may vary with the nature of the oil, and thus an appropriate selection thereof is important.

EXAMPLE 4-3

A 100 g amount of red iron oxide powder and 20 g of dihydrogen hexamethyl cyclotetrasiloxane were separately charged into separate vessels, which were connected to each other in a sealed system, followed by allowing to stand at 80° C. for 72 hours. Thus, 101.50 g of the treated red iron oxide was obtained. The resultant powder was then allowed to stand at 50° C. for further 24 hours in a dryer. As a result, 100.60 g of the red iron oxide powder modified by the first stage treatment was obtained.

Into a 1000 ml eggplant-shape flask, 50 g of the resultant powder material was taken. 10 mg of tri-n-octylmethylammonium chloroplatinate as a catalyst, 10 ml of 1-pentene and 300 ml of carbon tetrachloride were added thereto, and the whole was heated under reflux in a water bath for 5 hours. Thereafter, filtration was carried out using a glass filter (G-4). Further, filtration and washing were performed with 500 ml of chloroform and then the product was dried in a thermostatic chamber at 105° C. for 1 hour.

EXAMPLE 4-4

A 10 g amount of zinc oxide (or zinc white) powder and a liquid mixture of 2 g of dihydrogen hexamethyl cyclotetrasiloxane and 2 g of pentahydrogen pentamethyl cyclopentasiloxane were separately charged into separate vessels, which were connected to each other in a sealed system, followed by allowing to stand at 90° C. for 12 hours. Thus, 10.90 g of the treated zinc oxide powder was obtained. The resultant powder was then allowed to stand at 90° C. for a further 24 hours in a dryer. As a result, 10.60 g of the zinc oxide powder modified by the first stage treatment was obtained.

Into a 100 ml eggplant-shape flask, 5 g of the resultant zinc oxide was taken. Thereafter, 0.5 mg of chloroplatinic acid, 0.5 ml of 1-tetradecene and 30 ml of isopropanol were added thereto and the whole was heated under reflux in a water bath for 5 hours. Then, the filtration with a glass filter (G-4) and the washing with 50 ml of chloroform were carried out, and the powder was dried in a thermostatic chamber at 90° C. for 1 hour to yield the modified powder material. The resulting powder exhibited a remarkable hydrophobicity and the linalool decomposing ability disappeared. In the test of hydrogen generation, no hydrogen was detected.

EXAMPLE 4-5

A 10 g amount of silica powder and 5 g of tetrahydrogen tetramethyl cyclotetrasiloxane were separately charged into separate vessels, which were placed in a desiccator. The system was allowed to stand at 80° C. for 48 hours. After 48 hours, 14.50 g of the treated silica powder was obtained and was further allowed to stand at 120° C. for 24 hours in a dryer. Thus, 13.20 g of the treated silica powder was obtained. Then, 5 g of the resulting silica powder was taken into a 100 ml eggplant-shape flask. 10 mg of tri-n-octylmethylammonium chloroplatinate as a catalyst and 10 ml of styrene and 50 ml of carbon tetrachloride were added thereto, and the whole was heated under reflux in a water bath for 2 hours. Then, filtration was carried out using a glass filter (G-4). Further, filtration and washing were performed with 300 ml of carbon tetrachloride, and then the powder was dried in a thermostatic chamber at 105° C. for 1 hour. The resulting powder exhibited a remarkable hydrophobicity and the linalool decomposing ability disappeared. In the test of hydrogen generation, no hydrogen was detected.

EXAMPLE 4-6

(1) A 5 kg amount of finely divided titanium dioxide was charged into a 100 liter rotary double cone type reactor (made of stainless steel, equipped with a lagging jacket) and 500 g of a silicone compound having the following structure:

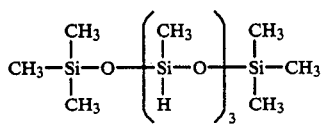

was charged into a stock liquor feeding tank (made of stainless steel, equipped with a lagging jacket) directly connected to the reactor by a stainless steel pipe. The system was evacuated to 20 mmHg by a vacuum pump. The temperature of the system was maintained at 90° C.

by feeding a heating medium heated at 90° C. from the heating medium heating tank by a circulation pump to the lagging jackets of the reactor and the stock liquor feeding tank. The reactor was rotated three times after being allowed to stand for 10 minutes, by means of a timer, thereby to mix and stir the titanium dioxide within the reactor, which operation was repeated for 5 hours. Then, the inner pressure was returned to atmospheric by introducing $N_2$ gas and 5.3 kg of the treated powder was obtained.

(2) A 100 g amount of the titanium dioxide powder covered by the silicone polymer film obtained in Example 4-6(1) was taken into a 1000 ml eggplant-shape flask, 5 ml of 1-octene and 400 ml of isopropyl alcohol containing 30 mg of chloroplatinic acid as a catalyst were added thereto, and the whole was heated under reflux in a water bath for 2 hours. Thereafter, filtration was carried out using a milliporefilter (filter type VC, 0.1 μm). The powder was dried at 100° C. for 5 hours to yield titanium dioxide powder covered with an alkyl-modified silicone polymer.

The modified powders obtained above were evaluated with respect to various tests as follows. The result is shown in Table 4-1 and 4-2 below.

(i) Coating Condition

The uniform coating conditions of the silicone polymer film coated on the surface of powder according to the present invention can be determined by means of an X-ray photoelectron spectroscopic analyzer (i.e., Shimazu ESCA 750). The determination was carried out under the conditions of 12 kW and 30 mA in the analyzer provided with an Mg conical anode, a semicircular filament, and a 2μ aluminum filter.

The sample was adhered to a both-surface adhesive type tape and the measurement was carried out within the range of 0 to 760 eV.

The coverage of the silicon polymer film can be confirmed because the coated silicone polymer exhibits bonding energies of $Si_{2S}$ and $Si_{2P}$ tracks different from the untreated powder.

(ii) Crosslinking Ratio
See Above
(iii) Chloroform soluble Matter
See Above
(iv) Water Repellency
See above
(v) Linalool Stability
See above
(vi) Colorimetry
See above
(vii) Specific Volume
See above
(viii) Chemical Agent Stability The color deterioration to dark brown of vitamin E, resorcinol, or γ-oryzanol was tested by directly bringing the sample powder into contact with the chemical agent. The results are evaluated as follows:
x: Changed to dark brown
Δ: Slightly changed to yellow
o : No change

TABLE 4-1

Figure 3:
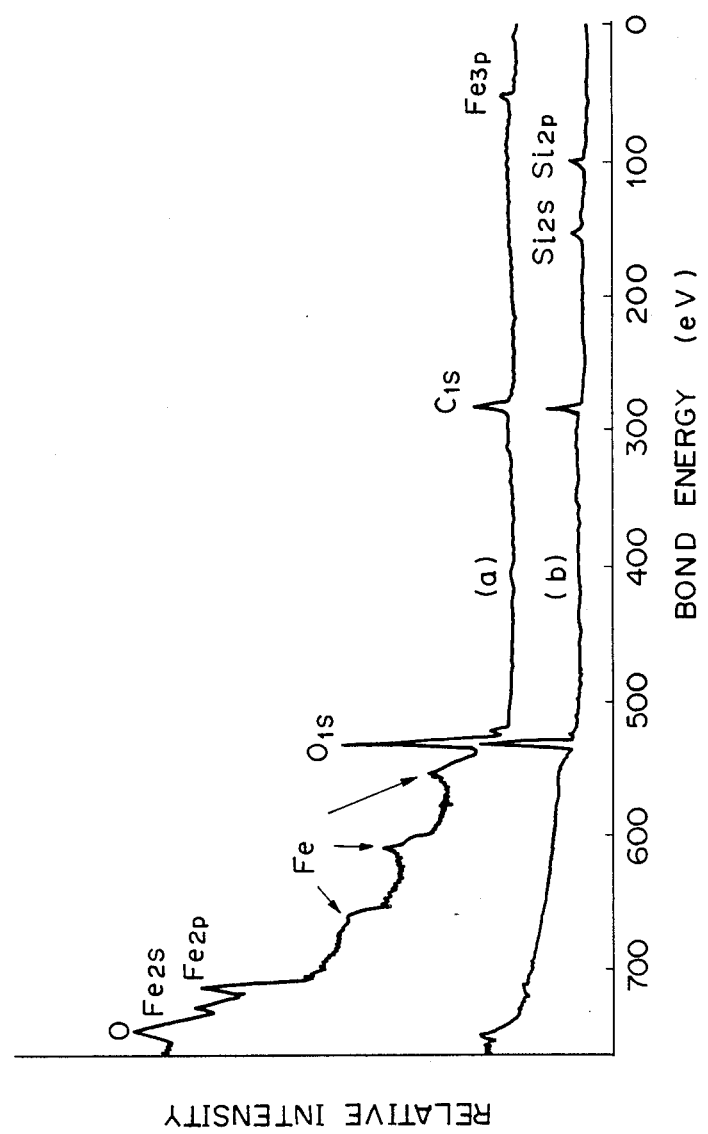
FIG. 3 shows the X-ray photoelectron spectrum of the yellow iron oxide powder samples of the untreated powder [i.e., chart (a)] and Example 4-1 [(i.e., chart (b)]

| | Color | | | Color difference ΔE | Water repellency | Specific volume (ml/g) | Linalool decomposition activity | Coating condition |
| --- | --- | --- | --- | --- | --- | --- | --- | --- |
| | L | a | b | | | | | |
| Yellow iron oxide (untreated) | 62.32 | 7.43 | 31.45 | — | X | 2.4 | Δ | See FIG. 3(a) |
| Example 4-1 | 61.20 | 7.63 | 32.64 | 1.65 | O | 2.4 | O | See FIG. 3(b) |

TABLE 4-2

Figure 4:
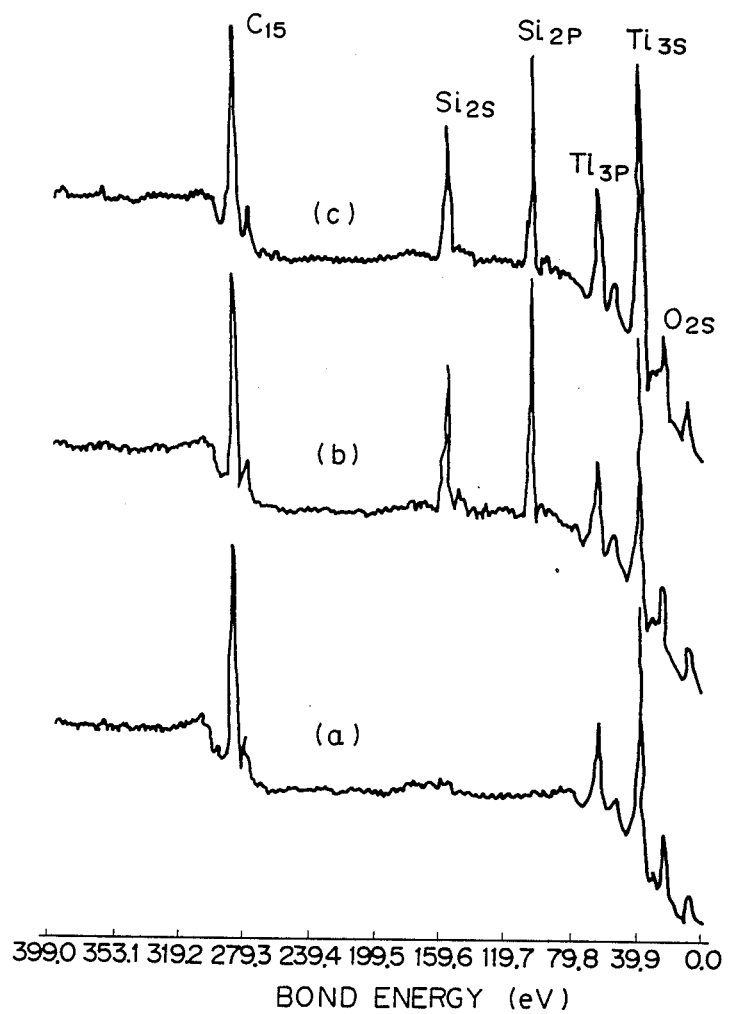
FIG. 4 shows the X-ray photoelectron spectrum of the titanium dioxide powder samples of the untreated powder [i.e., chart (a)], Example 4-6(1) [i.e., chart (b)], and Example 4-6(2) [i.e., chart (c)]

| No. | Coating Condition | Cross linking Ratio | Addition ratio | Chloroform Soluble-matter | Water Repellency | Linalool Stability | Chemical Agent*[1] Stability | | |
| --- | --- | --- | --- | --- | --- | --- | --- | --- | --- |
| | | | | | | | (1) | (2) | (3) |
| Untreated | — | — | — | — | X | Δ | X | X | O |
| Example 4-2(2) | — | 62 | 90 | No | O | O | O | O | O |
| Example 4-2(3) | — | 62 | 100 | No | O | O | O | O | O |
| Untreated | — | — | — | — | X | Δ | — | — | — |
| Example 4-3 | — | 81 | 100 | No | O | O | — | — | — |
| Untreated | — | — | — | — | X | Δ | O | O | O |
| Example 4-4 | — | 40 | 100 | No | O | O | O | O | O |
| Example 4-5 | — | 56 | 100 | No | O | O | O | O | O |
| Untreated | See FIG. 4(a). | — | — | — | X | Δ | X | X | — |
| Example 4-6(1) | See FIG. 4(b). | 66*[2] | — | No | O | O | O | O | — |
| Example 4-6(2) | See FIG. 4(c). | 66*[2] | 76*[2] | No | O | O | O | O | — |

Figure 5:
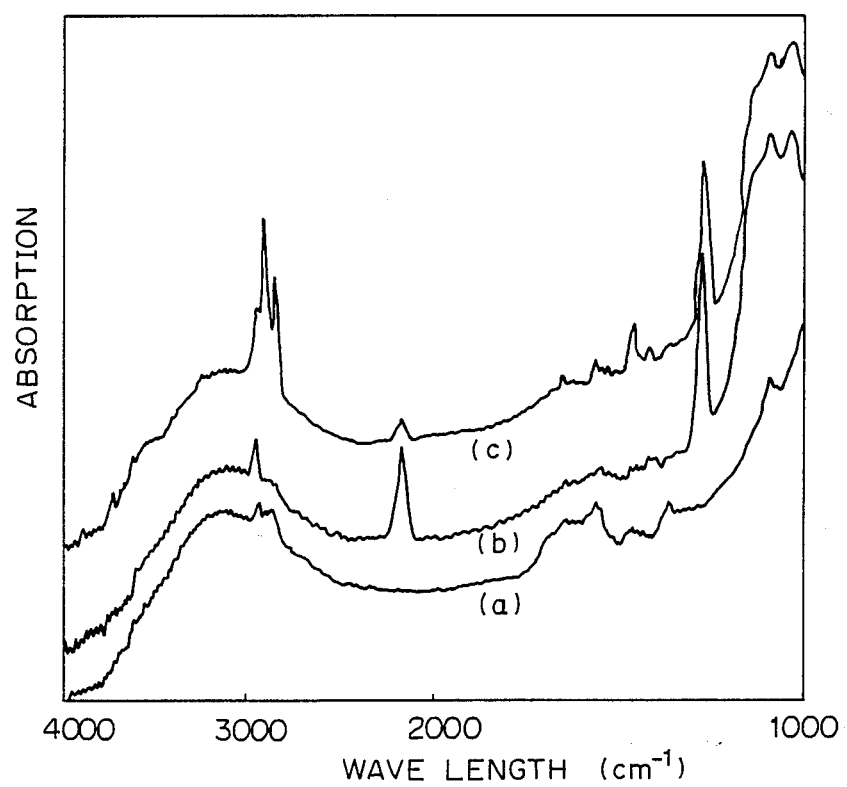
FIG. 5 shows the IR-absorption spectrum of the titanium dioxide powder samples of the untreated powder [i.e., chart (a)], Example 4-6(1) [i.e., chart (b)], and Example 4-6(2) [i.e., chart (c)]

*[1](1) ... Vitamin E, (2) ... γ-oryzanol, (3) ... resorcinol
*[2]See FIG. 5.

EXAMPLE 4-7

A 100 g amount of zinc oxide (zinc white) powder was dispersed in 400 g of dichloromethane, and 3 g of methyl hydrogen polysiloxane (M.W.=ca. 3000) was added thereto. The whole was heated under reflux at 50° C. for 2 hours. After evaporating dichloromethane at 100° C., 1.0 g of styrene and 400 g of isopropyl alcohol containing 10 mg of chloroplatinic acid as a catalyst were added, and the whole was heated under reflux in a water bath for 2 hours. Thereafter, filtration was carried out using a glass filter, washing was performed with isopropyl alcohol, and the product was dried at 80° C. The resultant modified powder, having a crosslinking ratio of 61% and an addition ratio of nearly 100%, does not cause a brown discoloration (whereas an untreated zinc oxide renders the same brown) with the linalool decomposition ability having disappeared.

EXAMPLE 4-8

A 20 g amount of black iron oxide was charged in a satellite ball mill, and mixed and ground for 5 minutes. Then, 1 g of methyl hydrogen polysiloxane (molecular weight=6,000) was added, followed by mixing and grinding for 3 hours. Thereafter, 0.5 g of docosene and 10 mg of tri-n-octylmethylammonium chloroplatinate were added, followed by mixing and grinding for 2 hours.

It was difficult to determine the infrared absorption spectrum of the treated black iron oxides, and thus the crosslinking and addition ratios were not determined. Moreover, the linalool decomposition ability disappeared. This means that the surface of the modified black iron oxide was covered with the silicone polymer film.

EXAMPLE 4-9

A 10 kg amount of spherical composite powder comprising 65 parts of nylon powder (5 μm) coated with 35 parts of titanium dioxide (0.2 μm) was charged into a 100 liter rotary double cone type reactor (made of stainless steel, equipped with a lagging jacket) and 1 kg of a silicone compound having the following structure:

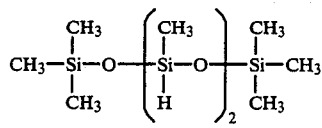

was charged into a stock liquor feed tank (made of stainless steel, equipped with a lagging jacket) directly connected to the reactor by a stainless steel pipe. $N_2$ was charged into the reactor by bubbling it from the bottom of the feed tank. The temperature of the system was maintained at 70° C. by feeding a heating medium heated at 70° C. from the heating medium heating tank by a circulation pump to the lagging jackets of the reactor and the stock liquor feeding tank. The reactor was rotated three times after being allowed to stand for 10 minutes by means of a timer thereby to mix and stir the composite powder within the reactor, which operation was repeated for 7 hours. Then, the silicone compound was removed and only $N_2$ was introduced to the reactor while rotating for further 2 hours. After the temperature was cooled to room temperature, 10.4 kg of the treated powder was recovered.

10 g of the treated composite powder and 1 g of styrene were homogeneously mixed. Then, a plasma radiation was carried out for 20 minutes at 30 W under a low frequency (5 KHz) by means of a plasma generator (Sankyo Dengyo K.K.), while a nitrogen gas was passed at a rate of 200 ml/min.

The modified powder exhibited remarkable water repellency, without losing the good flow property specific to the starting composite powder, and did not cause the unpreferably brown discoloration of vitamin E and γ-oryzanol caused by the starting composite powder. No hydrogen was detected in the test of hydrogen generation.

EXAMPLE 4-10

A 12.4 kg amount of the treated spherical silica was obtained in the same manner as in Example 4-8, except 10 kg of spherical silica (particle size of 5 μm, specific surface area of 350 m²/g) and 3 kg of a silicone compound having the following structure:

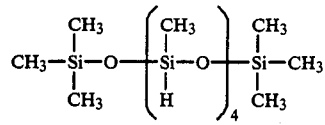

were used as a powder material and a treating agent, respectively, and the temperature of the system was at 100° C. Then, 1 kg of the resulting silica was taken into a 5 l flask.

50 mg of tri-n-octylmethylammonium chloroplatinate as a catalyst and 2 kg of 1-octadecene were added thereto, and the whole was heated under reflux by a mantle heater at 150° C. for 5 hours. Then, filtration was carried out using a glass filter (G-4). Further, washing were performed with 3 kg of chloroform and then 1.5 kg of methyl alcohol. The resultant silica covered with the alkyl-modified silicone polymer film exhibited a remarkable water repellency.

EXAMPLE 5-1

(1) A 1000 g amount of β-type C.I. 15850:1 (lithol rubine BCA) powder and 100 g of tetrahydrogen tetramethyl cyclotetrasiloxane were separately charged into separate vessels, which were then placed in a desiccator at 80° C. for 16 hours. The treated powder was then allowed to stand at 90° C. for a further 24 hours in a dryer. As a result, 1043 g of the C.I. 15850:1 (lithol rubine BCA) powder was obtained.

(2) A 200 g amount of the resulting C.I. 15850:1 (lithol rubine BCA) was taken into a 1 l Erhenmeyer flask, 20 g of 1-octene and 800 ml of isopropyl alcohol containing 50 mg of chloroplatinic acid as a catalyst were added thereto, and the whole was allowed to stand at room temperature for 16 hours. Thereafter, filtration was carried out, and further filtration and washing were performed with 500 ml of isopropanol. The product was dried at 90° C. for 5 hours in a dryer to yield 200.6 g of C.I. 15850:1 (lithol rubine BCA) covered with an alkyl-modified silicone polymer.

EXAMPLE 5-2

(1) A 300 g amount of C.I. 15850:1 (lithol rubine BCA) (β-type crystalline) powder and 100 g of the silicon compound having the following structure:

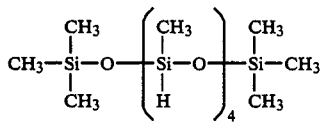

were separately charged into separate vessels and were then allowed to stand at 80° C. for 16 hours in a desiccator. After recovering from the vessel, the treated powder was dried at 90° C. for 24 hours in a dryer. Thus, 311 g of the treated powder was obtained.

(2) A 200.0 g amount of the resultant C.I. 15850:1 (lithol rubine BCA) was obtained in the same manner as in Example 5-1(2), except that treated C.I. 15850:1 (lithol rubine BCA) obtained in Example 5-2(1) was used.

The resultant powders and the untreated powder were evaluated in the same manner as mentioned above. The results are as follows:

(i) Chloroform Soluble Matter

A 82 mg amount (i.e., 1.9% of the total silicone compound) of the silicone polymer of Example 5-1(1) was dissolved in chloroform from 100 g of modified C.I. 15850:1 (lithol rubine BCA). The average molecular weight of the dissolved polymer was about 8000.

A 230 mg amount (i.e., about 6.3% of the silicone polymer) of the silicone polymer having an average molecular weight of about 4500 of Example 5-2(1) was dissolved in chloroform. No silicone polymer was dissolved in each of Examples 5-1(2) and 5-2(2).

(ii) α- and β-Transformation

The β-type C.I. 15850:1 (lithol rubine BCA) was transformed to the α-type in the presence of water. The percentage of the α-type of the modified powder was determined according to the X-ray peak thereof according to the following equation:

$$\alpha\text{-type transformation}(\%) = \frac{h\alpha}{h\alpha + h\beta} \times 100$$

wherein
$h\alpha$: height at $2\theta = 20.75°$
$h\beta$: height at $2\theta = 21.60°$ The results are as follows:

| Sample | α-transformation % | | | | |
|---|---|---|---|---|---|
| | 1 day | 3 days | 6 days | 10 days | 20 days |
| Untreated powder | 20 | 94 | 100 | 100 | 100 |
| Example 5-1(1) | 0 | 0 | 6 | 14 | 53 |
| Example 5-1(2) | 0 | 0 | 0 | 3 | 18 |
| Example 5-2(1) | 0 | 0 | 14 | 31 | 65 |
| Example 5-2(2) | 0 | 0 | 0 | 7 | 22 |

As clear from the above results, the delay of the α-transformation in the modified powders exhibits the difficulty of the transmission of water due to the formation of the silicone polymer film entirely covering the powder particles.

(iii) Bleeding Property

Since the C.I. 15850:1 (lithol rubine BCA) is a calcium lake pigment, it is dissolved to some extent in water when dispersing therein. Accordingly, the bleeding property of the powder was evaluated.

A 0.5 g amount of C.I. 15850:1 (lithol rubine BCA) was dispersed in 100 ml of deionized water and was allowed to stand at room temperature for one day. The amount of the dissolved C.I. 15850:1 (lithol rubine BCA) was determined, after filtration, by the absorbance at a maximum absorption wavelength of 490 nm by using a 1 cm cell.

The results are as follows:

| Sample No. | Absorbance |
|---|---|
| Untreated powder | 0.15 |
| Example 5-1(1) | 0.02 |
| Example 5-1(2) | 0 |
| Example 5-2(1) | 0.04 |
| Example 5-2(2) | 0 |

As is clear from the results shown above, according to the present invention, the bleeding property of each of the powders of Examples 5-1(1) and 5-2(1) was sustained and, particularly, that of each of the powders of Examples 5-1(2) and 5-2(2) disappeared due to the formation of a uniform silicone polymer film entirely covering the powder.

EXAMPLE 5-3

(1) A 1000 g amount of C.I. 74160 (phthalocyanine blue) and a liquid mixture of 100 g of tetrahydrogen hexamethyl cyclopentasiloxane and 50 g of pentahydrogen pentamethyl cyclopentasiloxane were separately charged into separate beakers, which were placed in a vacuum type low-temperature dryer DPF 31 (manufactured by Yamato Kagaku K.K.). The system was reduced to 20 mmHg and allowed to stand at 50° C. for 48 hours. Then, C.I. 74160 was removed and dried at 90° C. for 4 hours in a dryer to obtain 1048 g of the treated C.I. 74160.

(2) To a 1 l Erylenmeyer flask, 100 g of the resultant C.I. 74160 was taken. 50 mg of tri-n-octylmethylammonium chloroplatinate as a catalyst and 500 ml of 1-octadecene were added thereto and the whole was heated under reflux by a mantle heater at 170° C. for 5 hours. Then, filtration was carried out using a glass filter (G-4). Further, filtration and washing were performed with 300 ml of chloroform and then 300 ml of methyl alcohol. Thereafter, the powder was dried in a thermostatic chamber at 105° C. for 1 hour.

The resultant powders of Examples 5-3(1) and 5-3(2) were evaluated with respect to chloroform soluble matter in the same manner as in Examples 5-1 to 5-2.

A 57 mg amount (i.e., about 1.2% of the silicone polymer) of silicone polymer of Example 5-3(1) was dissolved in chloroform and an average molecular weight thereof was 23,000. No silicone polymer was dissolved from the modified powder of Example 5-3(2).

EXAMPLE 5-4

A 100 g amount of C.I. 74160 powder was dispersed in 400 g of dichloromethane, and 3 g of methyl hydrogen polysiloxane (M.W.=ca. 3000) was added thereto. The whole was heated under reflux at 50° C. for 2 hours. After evaporating dichloromethane at 100° C., 2.0 g of 1-octadecene and 400 g of isopropyl alcohol containing 10 mg of chloroplatinic acid as a catalyst were added, and the whole was heated under reflux in a water bath for 2 hours. Thereafter, filtration was carried out using a glass filter, washing was performed with isopropyl alcohol, and the product was dried at 80° C. to obtain 103.1 g of the modified powder.

EXAMPLE 5-5

A 20 g of C.I. 74160 powder was charged in a satellite ball mill, and mixed and ground for 5 minutes. Then, 1 g of hydrogen methyl polysiloxane (molecular weight=8,000) was added, followed by mixing and grinding for 3 hours. Thereafter, 0.2 g of docosene and 10 mg of tri-n-octylmethylammonium chloroplatinate were added, followed by mixing and grinding for 2 hours.

The powders of Examples 5-3 to 5-5 were evaluated with respect to dispersibility.

| Test for Dispersibility | Parts by weight |
|---|---|
| Pigment powder | 10 |
| Alkyd resin (133-60 NV 60: Hitachi Kasei Co.) | 54 |
| Melamine resin (Melan-20 NV 50: Hitachi Kasei Co.) | 26 |

| Test for Dispersibility | Parts by weight |
|---|---|
| Xylol | 10 |

A mixture of the above components was charged together with beads into a classifier and the dispersibility was observed by means of a fineness gage at 10 minute intervals. The result is shown in Table 5-3. It is apparent that a dispersing period to prepare a coating composition from the modified pigments of Examples 5-3 to 5-5 is a half of that needed to prepare a coating composition from an untreated pigment.

TABLE 5-3

(particle size in μm)

| Dispersing period (min) | 10 | 20 | 30 | 40 | 50 |
|---|---|---|---|---|---|
| Untreated | 30 | 24 | 18 | 24 | 10 |
| Example 5-3(1) | 22 | 14 | less than 10 | — | — |
| Example 5-3(2) | 20 | 12 | less than 10 | — | — |
| Example 5-4 | 20 | 13 | less than 10 | — | — |
| Example 5-5 | 21 | 12 | less than 10 | — | — |

EXAMPLE 6-1

(1) A 20 g amount of mica-titanium pearling material having an average particle size of 25 μm and 2 g of the silicone compound having the following structure:

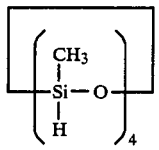

were separately charged into separate vessels, followed by allowing to stand at 80° C. for 12 hours in a desiccator. Then, the resultant mica-titanium pearling material was taken out of the vessel and was further allowed to stand at 100° C. for 24 hours.

As a result, 21.2 g of the pearling agent modified by the first stage treatment was obtained.

(2) To an Erlenmeyer flask, 10 g of the treated pearling material obtained in Example 6-1(1) was taken. 100 ml of isopropyl alcohol containing 10 mg of chloroplatinic acid as a catalyst and 1 ml of 1-octene were added thereto and the whole was heated under reflux in a water bath for 2 hours. Then, filtration was carried out using a glass filter (G-4), and the product was dried in a dryer at 100° C. for 5 hours to obtain the modified pearling material covered with an alkyl-modified silicone polymer film.

EXAMPLE 6-2

(1) A 20 kg amount of mica-iron oxide type pearling agent was charged into a 100 liter rotary double cone type reactor (made of stainless steel, equipped with a lagging jacket) and 400 g of tetrahydrogen tetramethyl cyclotetrasiloxane was charged into a stock liquor feeding tank (made of stainless steel, equipped with a lagging jacket) directly connected to the reactor by a stainless steel pipe. The inner pressure was evacuated to 100 mmHg by a vacuum pump. The temperature of the system was maintained at 90° C. by feeding a heating medium heated at 90° C. from the heating medium heating tank by a circulation pump to the lagging jackets of the reactor and the stock liquor feeding tank. The reactor was rotated three times after being allowed to stand for 10 minutes by means of a timer, to thereby mix and stir the mica-iron oxide within the reactor, which operation was repeated for 10 hours. Then, the inner pressure was returned to atmospheric by introducing N$_2$ gas and 20.3 kg of the powder modified by the first stage treatment was obtained.

(2) Into a 1000 ml eggplant-shape flask, 100 g of the resultant powder material of Example 6-2(1) was taken. 10 mg of tri-n-octylmethylammonium chloroplatinate as a catalyst, 10 ml of 1-pentene and 500 ml of carbon tetrachloride were added thereto, and the whole was heated under reflux in a water bath for 5 hours. Thereafter, filtration was carried out using a glass filter (G-4). Further, filtration and washing were performed with 500 ml of chloroform and then the product was dried in a thermostatic chamber at 90° C. for 1 hour to obtain the modified pearling material.

EXAMPLE 6-3

(1) In a gas sterilizer Kapokalizer CL-30B (Fuji Electric Co. Ltd.), 100 g of bismuth oxychloride and 20 g of pentamethyl pentahydrogen cyclopentasiloxane contained in separate vessels were placed and the inner pressure in the gas sterilizer was reduced to 300 mmHg by an aspirator, and the temperature was maintained at 90° C. After one night, the inner pressure was returned to atmospheric by introducing air, followed by repeating the evacuation several time, to obtain 103.6 g of the modified powder.

(2) A 50 g amount of the treated bismuth oxychloride covered by the silicone polymer film obtained in Example 6-3(1) was taken into a 500 ml eggplant-shape flask, 5 ml of 1-octadecene and 300 ml of t-butyl alcohol containing 2 mg of chloroplatinic acid as a catalyst were added thereto, and the whole was heated under reflux in a water bath for 2 hours. Thereafter, filtration by a glass filter and washing were carried out and then the product was dried at 100° C. for 5 hours in a dryer to yield bismuth oxychloride powder covered with an alkyl-modified silicone polymer.

EXAMPLE 6-4

(1) A 200 g amount of prussian blue coating mica-titanium pearling material and 30 g of trihydrogen pentamethyl cyclotetrasiloxane were separately charged into separate vessels, which were placed in a vaccum type low-temperature dryer DPF 31 (manufactured by Yamato Kagaku K.K.). The system was allowed to stand at 50° C. for 48 hours. Then, the pearling material was removed and dried at 80° C. for 6 hours to obtain 218.3 g of the treated pearling material.

(2) A 50 g amount of the pearling material covered by the silicone polymer film obtained in Example 6-4(1) was taken into a three-neck flask. After 400 ml of isopropyl alcohol containing 5 mg of chloroplatinic acid as a catalyst was added thereto, ethylene was blown. After 16 hours, filtration by a glass filter (G-4) and washing were carried out, and the product was dried at 100° C. for 5 hours in a dryer to yield pearling material covered with an alkyl-modified silicone polymer.

EXAMPLE 6-5

(1) A 50 g amount of green pearling material [titanium nitride oxide coating mica: prepared by coating with 10% of reducing Flamenco Blue commercially available from Mearl Co. in the United States of America with NH₃ gas and coating the resultant powder with 10% by weight of titanium dioxide] and 10 g of tetrahydrogen tetramethyl cyclotetrasiloxane were separately charged into separate vessels, which were allowed to stand in a desiccator at 30° C. for 4 days. After 4 days, the powder was removed and allowed to stand in a dryer at 100° C. for 3 hours to yield 52.3 g of the treated powder.

(2) A 10 g amount of the pearling material obtained in Example 6-5(1) was taken into a three-neck flask, 1 ml of a styrene and 100 ml of isopropyl alcohol containing 10 mg of chloroplatinic acid as a catalyst were added thereto, and the whole was heated under reflux in a water bath for 2 hours. After filtration was carried out using a glass filter (G-4), the product was dried at 100° C. for 5 hours in a dryer to yield pearling material covered with an alkyl-modified silicone polymer.

EXAMPLE 6-6

(1) A 21.2 g amount of treated mica-titanium pearling material was obtained in the same manner as in Example 6-1(1), except the silicone compound having the formula

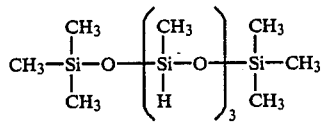

was used.

(2) The modified mica-titanium pearling material was obtained in the same manner as in Example 6-1(2), except the treated material obtained in Example 6-6(1) was used.

EXAMPLE 6-7

(1) A 20.36 g amount of treated mica-iron oxide pearling material was obtained in the same manner as in Example 6-2(1), except the silicone compound having the formula

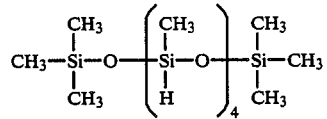

was used.

(2) The modified mica-iron oxide pearling material was obtained in the same manner as in Example 6-2(2), except the treated material obtained in Example 6-7(1) was used.

EXAMPLE 6-8

A 100 g amount of prussian blue coating mica-titanium pearling material was dispersed in 800 ml of dichloromethane, and 3 g of methyl hydrogen polysiloxane (M.W.=ca. 3000) was added thereto. The whole was heated under reflux at 50° C. for 2 hours. After evaporating dichloromethane at 80° C., 1.0 g of styrene and 400 g of isopropyl alcohol containing 10 mg of chloroplatinic acid as a catalyst were added, and the whole was heated under reflux in a water bath for 2 hours. Thereafter, filtration was carried out using a glass filter, washing was performed with isopropyl alcohol, and the product was dried at 80° C. to yield the modified pearling material.

EXAMPLE 6-9

A 100 g amount of the green pearling material used in Example 6-5(1) was dispersed in 400 g of dichloromethane containing 1 g of methyl hydrogen polysiloxane (M.W.=ca. 12000). The whole was heated under reflux for 3 hours. After evaporating dichloromethane at 100° C., the powder was dried at 130° C. for 2 hours. To the resulting powder, 2 g of 1-octadecene and 400 g of isopropyl alcohol containing 10 mg of chloroplatinic acid as a catalyst were added, and the whole was heated under reflux for 3 hours. Thereafter, filtration was carried out using a glass filter, washing was performed with isopropyl alcohol, and the product was dried at 100° C. to yield the modified pearling material.

The powders obtained in Examples 6-1, and 6-6 were evaluated with respect to glossiness. The gloss angle of the pearling material was measured by means of a glossmeter (Hitachi Manufacturing Co.) at an incidence angle of 15° and a receiving angle of 30°. The values shown in Table 6-1 are an average of the two measurements.

TABLE 6-1

|  | Glossiness | | |
| --- | --- | --- | --- |
|  | L | a | b |
| Untreated | 87.8 | 0.34 | −8.9 |
| Example 6-1(1) | 96.0 | 0.38 | −8.4 |
| Example 6-1(2) | 96.3 | 0.38 | −8.3 |
| Example 6-6(1) | 95.7 | 0.37 | −8.4 |
| Example 6-6(2) | 96.1 | 0.37 | −8.3 |

The powders obtained in Examples 6-1 to 6-9 were evaluated in the same manner as mentioned above. The results are shown in Table 6-2.

TABLE 6-2

| Ex. No. | 100×/(x + y) | Addition ratio (%) | Chloroform soluble | Linalool stability | Water repellency |
| --- | --- | --- | --- | --- | --- |
| Untreated | — | — | — | Δ | x |
| Example 6-5(1) | 43 | — | — | o | o |
| Example 6-5(2) | 43 | 100 | — | o | o |
| Untreated | — | — | — | Δ | x |
| Example 6-6(1) | 74 | — | No | o | o |
| Example 6-6(2) | 74 | 100 | No | o | o |
| Untreated | — | — | — | Δ | x |
| Example 6-7(1) | 62 | — | — | o | o |
| Example 6-7(2) | 62 | 100 | — | o | o |
| Untreated | — | — | — | Δ | x |
| Example 6-8 | 45 | 100 | — | o | o |
| Untreated | — | — | — | Δ | x |
| Example 6-9 | 32 | 100 | — | o | o |
| Untreated | — | — | — | Δ | x |
| Example 6-5(1) | 43 | — | — | o | o |
| Example 6-5(2) | 43 | 100 | — | o | o |
| Untreated | — | — | — | Δ | x |
| Example 6-6(1) | 74 | — | No | o | o |
| Example 6-6(2) | 74 | 100 | No | o | o |
| Untreated | — | — | — | Δ | x |
| Example 6-7(1) | 62 | — | — | o | o |
| Example 6-7(2) | 62 | 100 | — | o | o |
| Untreated | — | — | — | Δ | x |
| Example 6-8 | 45 | 100 | — | o | o |
| Untreated | — | — | — | Δ | x |
| Example 6-9 | 32 | 100 | — | o | o |

EXAMPLE 7-1

(1) A 100 g amount of kaolinite having an average particle size of 5 μm and 20 g of tetrahydrogen tetramethyl cyclotetrasiloxane were separately charged into separate vessels and were then allowed to stand at 80° C. for 12 hours in a desiccator. The treated kaolinite was recovered and was further allowed to stand at 100° C. for 24 hours in a dryer. As a result, 102.6 g of the modified kaolinite was obtained.

(2) A 50 g amount of the treated kaolinite obtained in Example 7-1(1) was taken into an Erlenmeyer flask, 5 ml of 1-decene and 500 ml of isopropyl alcohol containing 50 mg of chloroplatinic acid as a catalyst were added thereto, and the whole was heated under reflux in a water bath for 2 hours. After filtration with a glass filter (G-4) was carried out, the product was dried at 100° C. for 5 hours in a dryer to yield kaolinite covered with an alkyl-modified silicone polymer.

EXAMPLE 7-2

(1) A 20 kg amount of talc was charged into a 100 liter rotary double cone type reactor (made of stainless steel, equipped with a lagging jacket) and 400 g of tetrahydrogen tetramethyl cyclotetrasiloxane was charged into a stock liquor feeding tank (made of stainless steel, equipped with a lagging jacket) directly connected to the reactor by a stainless steel pipe. The pressure of the system was reduced by a vacuum pump to 20 mmHg. The temperature of the system was maintained at 90° C. by feeding a heating medium heated at 90° C. from the heating medium heating tank by a circulation pump to the lagging jackets of the reactor and the stock liquor feeding tank. The reactor was rotated three times after being allowed to stand for 10 minutes, by means of a timer, thereby to mix and stir the treated talc within the reactor, which operation was repeated for 10 hours. Then, the inner pressure was returned to atmospheric by introduction of $N_2$ gas and 20.3 kg of the treated talc was obtained.

(2) Into a 1000 ml eggplant-shape flask, 100 g of the resultant talc of Example 7-2(1) was taken. 10 mg of tri-n-octylmethylammonium chloroplatinate as a catalyst, 10 ml of 1-pentene and 500 ml of carbon tetrachloride were added thereto, and the whole was heated under reflux in a water bath for 5 hours. Thereafter, filtration was carried out using a glass filter (G-4). Further, washing were performed with 500 ml of chloroform and then the powder was dried in a thermostatic chamber at 90° C. for 1 hour.

EXAMPLE 7-3

(1) In a gas sterilizer Kapokalizer CL-30B (Fuji Electric co. Ltd.), 100 g of Y type zeolite and 20 g of pentamethyl pentahydrogen cyclopentasiloxane contained in separate vessels were placed and the inner pressure in the gas sterilizer was reduced to 300 mmHg by an aspirator, and the temperature was maintained at 90° C. The whole was allowed to stand overnight, and then the inner pressure was returned to atmospheric by introducing air, followed by repeating the evacuation several times, to obtain 101.2 g of the treated powder.

(2) A 50 g amount of the treated y type zeolite obtained in Example 7-3(1) was taken into a 500 ml eggplant-shape flask, 5 ml of 1-octadecene and 300 ml of t-butyl alcohol containing 2 mg of chloroplatinic acid as a catalyst were added thereto, and the whole was heated under reflux in a water bath for 2 hours. Thereafter, filtration by a glass filter (G-4) and washing were carried out, and then the powder was dried at 100° C. for 5 hours in a dryer to yield Y type zeolite powder covered with an alkyl-modified silicone polymer.

EXAMPLE 7-4

(1) A 5 kg amount of montmorillonite powder was charged into a 100 liter rotary double cone type reactor (made of stainless steel, equipped with a lagging jacket) and 500 g of trihydrogen pentamethyl cyclotetrasiloxane was charged into a stock liquor feeding tank (made of stainless steel, equipped with a lagging jacket) directly connected to the reactor by a stainless steel pipe. $N_2$ was fed to the reactor by bubbling it through the liquor feeding tank. The temperature of the system was maintained at 70° C. by feeding a heating medium heated at 70° C. from the heating medium heating tank by a circulation pump to the lagging jackets of the reactor and the stock liquor feeding tank. The reactor was rotated three times after being allowed to stand for 10 minutes by means of a timer, which operation was repeated for 7 hours. Then, the silicone compound was removed and, while $N_2$ was fed to the reactor, the system was heated to 100° C. The rotation was continued for further 2 hours to remove the silicone monomer from the system. The temperature was cooled to room temperature and the treated montmorillonite powder was obtained.

(2) Into a 1000 ml eggplant-shape flask, 100 g of the resultant montmorillonite was taken. Thereafter, 10 mg of chloroplatinic acid, 10 ml of 1-tetradecene and 400 ml of isopropanol were added thereto and the whole was heated under reflux in a water bath for 5 hours. Then, the filtration withe a glass filter (G-4) and the washing with 600 ml of chloroform were carried out, and the powder was dried in a thermostatic chamber at 90° C. for 1 hour to yield the modified powder material. No hydrogen was detected from the resulting powder in the test of hydrogen generation.

EXAMPLE 7-5

(1) A 50 g amount of organically modified montmorillonite powder (i.e., Benton 38 available from N.L. Co.) and 50 g of tetrahydrogen tetramethyl cyclotetrasiloxane were separately charged into separate vessels and were then allowed to stand at 50° C. for 48 hours in a vaccum type low-temperature dryer DPF-31 (manufactured by Yamato Kagaku K.K.). Thereafter, the powder was further allowed to stand at 80° C. Thus, 85 g of the treated powder was obtained, which was expanded when compared with the state before the treatment.

(2) To the three-neck flask, 50 g of the treated powder material of Example 7-5(1) was charged. 400 ml of isopropyl alcohol containing 5 mg of chloroplatinic acid and then 2 g of styrene were added thereto, and the reaction was performed at room temperature for 16 hours. Thereafter, filtration by a glass filter (G-4) and washing with isopropyl alcohol were carried out, and then the powder was dried in a dryer at 100° C. for 5 hours to obtain the modified powder.

EXAMPLE 7-6

(1) A 100 g amount of kaolinite having an average particle size of 5 μm and 20 g of 1,1,1,2,3,4,4,4-octamethyl tetrasiloxane were separately charged into separate vessels, followed by allowed them to stand at 80° C. for 12 hours in a desiccator. The resultant kaolinite was then allowed to stand at 100° C. for 24 hours in a dryer. Thus, 103.4 g of the treated kaolinite was obtained.

(2) To an Erlenmeyer flask, 50 g of the treated powder material of Example 7-6(1) was charged. 500 ml of isopropyl alcohol containing 50 mg of chloroplatinic acid as a catalyst and 5 ml of 1-decene were added thereto, and the whole was heated under reflux in a water bath for 2 hours. Thereafter, filtration by a glass filter (G-4) was carried out, and then the powder was dried in a dryer at 100° C. for 5 hours to obtain the modified powder.

EXAMPLE 7-7

(1) A 20.3 kg of the modified talc was obtained in the same manner as in Example 7-2(1), except that 1,1,1,2,3,4,4,4-octamethyl tetrasiloxane was used as a treating agent.

(2) A modified talc covered with an alkyl-modified silicone polymer was obtained in the same manner as in Example 7-2(2), except that the treated talc of Example 7-7(1) was used as a powder material.

EXAMPLE 7-8

A 102.1 g of the modified Y type zeolite was obtained in the same manner as in Example 7-3(1), except that 1,1,1,2,3,4,5,5,5-nonamethyl pentasiloxane was used as a treating agent.

(2) A modified Y type zeolite covered with an alkyl-modified silicone polymer was obtained in the same manner as in Example 7-3(2), except that the treated talc of Example 7-8(1) was used as a powder material.

EXAMPLE 7-9

A 100 g amount of montmorillonite was dispersed in 400 g of dichloromethane, and 3 g of methyl hydrogen polysiloxane (M.W.=ca. 3000) was added thereto. The whole was heated under reflux at 50° C. for 2 hours. After evaporating dichlomethane at 100° C., 1.0 g of styrene and 400 g of isopropyl alcohol containing 10 mg of chloroplatinic acid as a catalyst were added, and the whole was heated under reflux in a water bath for 2 hours. Thereafter, filtration by a glass filter and washing with isopropyl alcohol were carried out, and the product was dried at 80° C.

EXAMPLE 7-10

A 20 g amount of organically modified montmorillonite powder was charged in a satellite ball mill, and mixed and ground for 5 minutes. Then, 1 g of hydrogen methyl polysiloxane (molecular weight: ca. 6,000) was added, followed by mixing and grinding for 3 hours. Thereafter, 0.5 g of docosene and 10 mg of chloroplatinic acid were added, followed by mixing and grinding for 2 hours.

The powders of Examples 7-1 to 7-10 were evaluated in the same manner as mentioned above. The results are shown in the following Table 7-1.

TABLE 7-1

| | Crosslinking ratio (%) | Addition ratio (%) | Water repellency | Linalool stability |
|---|---|---|---|---|
| Untreated | — | — | Δ | Δ |
| Example 7-1(1) | 35 | — | o | o |
| Example 7-1(2) | 35 | 100 | o | o |
| Untreated | — | — | Δ | Δ |
| Example 7-2(1) | 42 | — | o | o |
| Example 7-2(2) | 42 | 100 | o | o |
| Untreated | — | — | x | Δ |
| Example 7-3(1) | 58 | — | o | o |
| Example 7-3(2) | 58 | 80 | o | o |
| Untreated | — | — | x | Δ |
| Example 7-4(1) | 32 | — | o | o |
| Example 7-4(2) | 32 | 100 | o | o |
| Untreated | — | — | Δ | Δ |
| Example 7-5(1) | 62 | — | o | o |
| Example 7-5(2) | 62 | 100 | o | o |
| Untreated | — | — | x | Δ |
| Example 7-6(1) | 39 | — | o | o |
| Example 7-6(2) | 39 | 100 | o | o |
| Untreated | — | — | Δ | Δ |
| Example 7-7(1) | 43 | — | o | o |
| Example 7-7(2) | 43 | 100 | o | o |
| Untreated | — | — | x | Δ |
| Example 7-8(1) | 55 | — | o | o |
| Example 7-8(2) | 55 | 80 | o | o |
| Untreated | — | — | x | Δ |
| Example 7-9 | 33 | 100 | o | o |
| Untreated | — | — | Δ | Δ |
| Example 7-10 | 69 | 100 | o | o |

EXAMPLE 8-1

(1) A 100 g amount of spherical porous silica having a specific surface area of 350 m²/g, a micropore size of 116 Å, and a particle size of 10 μm and 100 g of tetramethyl tetrahydrogen cyclotetrasiloxane were separately charged into separate vessels, followed by allowing to stand at 80° C. for 24 hours in a desiccator. The resultant silica was then allowed to stand at 100° C. for 2 hours in a dryer. Thus, 123.3 g of the silica modified by the first stage treatment was obtained.

(2) Into a 500 ml eggplant-shape flask, 50 g of the resultant porous silica was taken. Thereafter, 10 mg of chloroplatinic acid, 10 ml of 1-octadecene and 150 ml of isopropanol were added thereto and the whole was heated under reflux in a water bath for 5 hours. Then, the filtration with a glass filter (G-4) and the washing with 500 ml of chloroform were carried out, and the powder material. In the test of hydrogen generation, no hydrogen was detected from the resulting powder.

COMPARATIVE EXAMPLE 8-1

A 10 g amount of tetramethyl tetrahydrogen cyclotetrasiloxane was added to 10 g of the porous silica used in Example 8-1(1), followed by allowing them to react at 80° C. for 24 hours in a closed system.

COMPARATIVE EXAMPLE 8-2

A 10 g amount of the porous silica used in Example 8-1(1) and 20 g of alumina ball were charged into a ball mill. After agitating for 30 minutes, 10 g of tetramethyl tetrahydrogen cyclotetrasiloxane was added and the mixture was then agitated for one hour.

The modified or treated porous silica obtained above was evaluated as follows:

(i) Change of Shape

The modified silica powders obtained in Examples 8-1(1) and 8-1(2), maintained the original spherical shape and a good flowability. No agglomeration was observed. Contrary to this, the treated silica in Comparative Example 8-1 caused agglomeration to become solid or to mass, although the original spherical shape was maintained. Furthermore, in Comparative Example 8-2, the original shape was not maintained at all and the mixture became a slurry in which the silica and the resin were solidified as a mixture.

(ii) Change of Micropore Size

The micropore size was determined by means of an Autosorb-1 manufactured by Quantachrome Co., Ltd.

In Example 8-1(1), the diameter of the micropore of the porous silica was changed from 116 Å to 102 Å. Thus, the size of the micropore was reduced by 7 Å in radius. This means that a thin silicone polymer film having a thickness of about 7 Å was uniformly coated in the inside surface of the micropore.

In Example 8-1(2), the diameter of the micropore was changed to 90 Å. This means that a layer having a thickness of about 6 Å of stearyl pendant groups was attached to the silicone polymer film.

Contrary to this, in Comparative Examples 8-1 and 8-2, the micropores substantially disappeared because the liquid silicone compounds entered the micropores and, therefore, the coating only on the surface of the micropore was impossible.

(iii) Surface Activity

The surface activity of the silica was evaluated from the decomposition of linalool, a compound of perfumes or fragrants, in a microreactor as mentioned above.

The untreated silica decomposed linalool to form myrcene, limonene, cis-ocimene, trans-ocimene, and the like. This illustrates that solid acids are present on the surface of the untreated silica and cause the dehydration of the tertiary alcohol of linalool.

Contrary to this, the modified silica obtained in Example 8-1 did not decompose the linalool at all. This clearly illustrates that the surface activity on the surface of the silica had disappeared due to the coverage of the thin silicone polymer film. Although no evaluations were carried out of the products of Comparative Examples 8-1 and 8-2, it is believed that the active sites on the surface were sufficiently covered by the silicone oligomer.

EXAMPLE 8-2

(1) A 100 g amount of alumina (a particle size of 3 mm$\phi$, a specific surface area of 2 m$^2$/g, baked at 1100° C. after granulation) and 100 g of tetramethyl tetrahydrogen cyclotetrasiloxane were separated charged into separate vessels, followed by allowing to stand at 25° C. in a desiccator for 72 hours. The alumina was taken out from the desiccator and was further allowed to stand at 50° C. for 3 hours.

As a result, 100.6 g of the alumina modified by a first stage treatment was obtained.

(2) Into a 500 ml eggplant-shape flask, 50 g of the resultant alumina was taken. Thereafter, 0.1 g of benzoyl peroxide, 1 g of 9-hendecenoic acid and 200 ml of hexane were added thereto and the whole was heated at 75° C. under reflux in a nitrogen stream for 14 hours. Then, the filtration with a glass filter (G-4) and the washing with 500 ml of chloroform were carried out, and the powder was dried in a thermostatic chamber at 90° C. for 1 hour to yield the modified powder material. The resulting powder exhibited a remarkable hydrophobicity and the linalool decomposing ability disappeared. In the test of hydrogen generation, no hydrogen was detected.

EXAMPLE 8-3

A doll having a weight of 53.5 g and obtained by molding clay (mainly containing kaolin) and baking it at 1000° C., and 10 g of tetramethyl tetrahydrogen cyclotetrasiloxane were separately charged into separate vessels, followed by allowing to stand at 50° C. for 24 hours. After taking out from the desiccator, the doll was further allowed to stand at 50° C. for 3 hours. The weight of the treated doll was 56.2 g.

Into a desiccator, 56.2 g of the resultant doll, 10 ml of t-butyl amine contained in a petri dish and 20 g of calcium carbide contained in a beaker were placed. The temperature in the desiccator was maintained at 30° C.

Into the beaker, water was added at a rate of 5 ml/h to generate acetylene, while the air tight condition was maintained in the desiccator. After 24 hours, the doll was taken out and dried at 80° C.

The resultant doll exhibited a remarkable hydrophobicity, and was crushed into powder and subjected to the hydrogen generation test. No hydrogen was detected.

EXAMPLE 9-1

A 10 g amount of activated carbon powder and 10 g of tetrahydrogen tetramethyl cyclotetrasiloxane were separately charged into separate vessels, which were placed at 80° C. After 72 hours, 15.50 g of the treated powder was obtained and was further allowed to stand at 50° C. for 24 hours in a dryer. Thus, 13.60 g of the treated powder was obtained.

Then, 6 g of the resulting powder was taken into a 200 ml eggplant-shape flask. 10 mg of tri-n-octylmethylammonium chloroplatinate as a catalyst, 10 ml of 1-decene and 50 ml of chloroform were added thereto, and the whole was heated under reflux in a water bath for 2 hours. Then, filtration by a glass filter (G-4) and washing with 100 ml of chloroform were performed and then the powder was dried in a thermostatic chamber at 105° C. for 1 hour.

EXAMPLE 9-2

A 100 g amount of carbon black powder and 50 g of tetrahydrogen tetramethyl cyclotetrasiloxane were separately charged into separate vessels and were allowed to stand at room temperature for 96 hours in a closed container. Thus, 126.50 g of the treated carbon black powder was obtained. The treated carbon black was further allowed to stand at 50° C. for 24 hours in a dryer. As a result, 120.3 g of the treated carbon black was obtained.

Into a 500 ml eggplant-shape flask, 50 g of the resultant carbon black was taken. Thereafter, 5 mg of chloroplatinic acid, 5 ml of 1-tetradecene and 300 ml of isopropanol were added thereto and the whole was heated under reflux in a water bath for 5 hours. Then, the filtration with a glass filter (G-4) and the washing with 500 ml of chloroform were carried out, and the powder was dried in a thermostatic chamber at 90° C. for 1 hour to yield the modified powder material. The resulting powder exhibited a remarkable hydrophobicity and the linalool decomposing ability disappeared. In the test of hydrogen generation, no hydrogen was detected.

The resultant powders were evaluated in the same manner as mentioned above.

The results are as follows:

| Sample | Cross-linking Ratio | Addition Ratio (%) | Water Repellency | Linalool Stability |
|---|---|---|---|---|
| Untreated (Activated carbon) | — | — | x | Δ |
| Example 9-1 | 59 | 100 | o | o |
| Untreated (Carbon black) | — | — | x | Δ |

-continued

| Sample | Cross-linking Ratio | Addition Ratio (%) | Water Repellency | Linalool Stability |
|---|---|---|---|---|
| Example 9-2 | 70 | 100 | o | o |

EXAMPLE 10-1

(1) A 20 g amount of muscovite having an average particle size of 2 μm and 2 g of tetrahydrogen tetramethyl cyclotetrasiloxane were separately charged into separate vessels, which were connected to each other in a sealed system, followed by allowing to stand at 80° C. for 16 hours. Thus, 21.8 g of the treated muscovite was obtained. The resultant powder was then allowed to stand at 100° C. for further 24 hours in a dryer. As a result, 21.4 g of the treated muscovite was obtained.

(2) A 10 g amount of the treated muscovite powder obtained in Example 10-1 (1) was taken into a 100 ml Erlenmeyer flask, 1 ml of 1-octene and 20 ml of isopropyl alcohol containing 10 mg of chloroplatinic acid as a catalyst were added thereto, and the whole was heated under reflux in a water bath for 2 hours. Thereafter, filtration by a glass filter (G-4) and washing with 50 ml of isopropyl alcohol were carried out, and the powder was dried at 100° C. for 5 hours in a dryer.

COMPARATIVE EXAMPLE 10-1

A 2 g amount of octamethyl cyclotetrasiloxane was added to 20 g of muscovite having an average particle size of 2 μm, followed by stirring with a small sized stirrer. Then, the mixture was baked in an electric oven for 2 hours at 250° C.

COMPARATIVE EXAMPLE 10-2

A 20 g amount of muscovite having an average particle size of 2 μm and 1.4 g of hydrogen methyl polysiloxane having an average molecular weight of 3000 were charged into a ball mill, followed by milling for 30 minutes.

EXAMPLE 10-2

(1) A 1 g amount of muscovite having an average particle size of 2 μm and 20 g of tetrahydrogen tetramethyl cyclotetrasiloxane were separately charged into separate vessels, which were placed in a desiccator and allowed to stand at 50° C. The weight changes were determined every day, and after seven days, the weight increased to 8.2 g.

(2) Into a 100 ml eggplant-shape flask, 5 g of the resultant muscovite was taken. Thereafter, 0.2 ml of a solution of 1% chloroplatinic acid in isopropanol, 1 ml of allyl glycidyl ether and 60 ml of toluene were added thereto and the whole was heated at 140° C. under reflux for 5 hours. Then, the filtration with a glass filter (G-4) and the washing with 500 ml of chloroform were carried out, and the powder was dried in a thermostatic chamber at 90° C. for 1 hour to yield the modified powder material. In the test of hydrogen generation, no hydrogen was detected from the resulting powder.

EXAMPLE 10-3

A 1 g amount of muscovite having an average diameter of 2 μm and 9 g of tetrahydrogen tetramethyl cyclotetrasiloxane were charged into a sample tube, followed by allowing to stand at room temperature for 24 hours. The muscovite was expanded to a surface of the siloxane liquid.

COMPARATIVE EXAMPLE 10-3

A 1 g amount of muscovite having an average diameter of 2 μm and 9 g of octamethyl cyclotetrasiloxane were charged into a sample tube, followed by allowing to stand at room temperature for 24 hours.

COMPARATIVE EXAMPLE 10-4

A 1 g amount of muscovite having an average particle size of 2 μm and 9 g of hydrogen methyl polysiloxane having an average molecular weight of 3000 were charged into a sample tube, followed by allowing to stand at room temperature for 24 hours.

EXAMPLE 10-4

(1) A 100 g amount of biotite having an average particle size of 5 μm and 1 g of dihydrogen hexamethyl cyclotetrasiloxane were separately charged into separate vessels and were then placed in a closed container, followed by allowing to stand at 80° C. for 72 hours. The resultant powder was dried at 100° C. in a dryer. As a result, 100.6 g of the treated biotite was obtained.

(2) Into a 500 ml eggplant-shape flask, 50 g of the resultant biotite was taken. Thereafter, 50 mg of triethyl amine as a catalyst, 5 ml of acrylonitrile and 200 ml of acetonitrile were added thereto and the whole was heated at 160° C. under reflux for 5 hours. Then, the filtration with a glass filter (G-4) and the washing with 500 ml chloroform were carried out, and the powder was dried in a thermostatic chamber at 90° C. for 1 hour to yield the modified powder material. In the test of hydrogen generation, no hydrogen was detected from the resultant powder.

EXAMPLE 10-5

(1) A 100 g amount of synthetic mica having an average particle size of 8 μm and 5 g of a mixed solution of tetrahydrogen tetramethyl cyclotetrasiloxane and pentahydrogen pentamethyl cyclopentasiloxane (1:1) were separately charged into a gas sterilizer. The inner pressure was then evacuated to 100 mmHg by an aspirator and the temperature was maintained at 30° C. After 6 hours, air was fed in to return the inner pressure to a normal pressure. The inner pressure was evacuated several times. Thus, 103.2 g of the treated synthetic mica was obtained.

(2) Into a 500 ml eggplant-shape flask, 50 g of the resultant synthetic mica was taken. Thereafter, 5 mg of chloroplatinic acid, 5 ml of 1-tetradecene and 300 ml of isopropanol were added thereto and the whole was heated under reflux in a water bath for 5 hours. Then, the filtration with a glass filter (G-4) and the washing with 500 ml of chloroform were carried out, and the powder was dried in a thermostatic chamber at 90° C. for 1 hour to yield the modified powder material. The resulting powder exhibited a remarkable hydrophobicity and the linalool decomposing ability disappeared. In the test of hydrogen generation, no hydrogen was detected.

The powders obtained above were evaluated with respect to various tests in the same manner as mentioned above. The results are shown in Table 10 below.

TABLE 10

| No. | Cross-linking ratio (%) | Addition ratio (%) | Water repellency | Linalool stability |
|---|---|---|---|---|
| Example 10-1(1) | 45 | — | o | o |
| Example 10-1(2) | 45 | 100 | o | o |
| Comparative Example | | | | |
| 10-1 | — | — | x | x |
| 10-2 | — | — | Δ | Δ |
| Untreated mica | — | — | x | Δ |

EXAMPLE 10-6

(1) A 5 kg amount of muscovite having an average diameter of 2 μm was charged into a 100 liter rotary double cone type reactor (made of stainless steel, equipped with a lagging jacket) and 500 g of a silicone compound having the following structure:

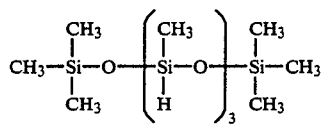

was charged into a stock liquor feeding tank (made of stainless steel, equipped with a lagging jacket) directly connected to the reactor by a stainless steel pipe. The system was evacuated to 20 mmHg by a vacuum pump. The temperature of the system was maintained at 90° C. by feeding a heating medium heated at 90° C. from the heating medium heating tank by a circulation pump to the lagging jackets of the reactor and the stock liquor feeding tank. The reactor was rotated three times after being allowed to stand for 10 minutes by means of a timer, thereby to mix and stir the muscovite within the reactor, which operation was repeated for 5 hours. Then, the inner pressure was returned to atmospheric by introducing $N_2$ gas and 5.3 kg of the treated muscovite was obtained.

(2) A 100 g amount of the muscovite powder obtained in Example 10-6(1) was taken into a 100 ml eggplant-shape flask, 5 ml of 1-octene and 400 ml of isopropyl alcohol containing 30 mg of chloroplatinic acid as a catalyst were added thereto, and the whole was heated under reflux in a water bath for 2 hours. Thereafter, filtration was carried out using a milliporefilter (filter type VC, 0.1 μm). The powder was dried at 100° C. for 5 hours to yield 100.3 g of muscovite powder covered with an alkyl-modified silicone polymer.

The muscovite powders obtained above were evaluated with respect to various tests as mentioned above. The results are as follows.

(i) Crosslinking Ratio $100x/(x+y)$ in Example 10-6(1): 70%

(ii) Structure of Silicone Polymer of Example 10-6(1)

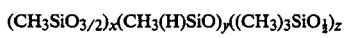

$x:y:z = 42:18:40$ (iii) Addition Ratio of Example 10-6(2): 100%

(iv) Structure of Silicone Polymer of Example 10-6(2)

$x':y':z' = 42:18:40$ (v) Chloroform Soluble Matter

No soluble matter was found (i.e., M.W. > 200,000) in Examples 10-6(1) and 10-6(2)

(vi) Water Repellency and Linalool Stability

| Sample | Water Repellency | Linalool Stability |
|---|---|---|
| Untreated Muscovite | x | Δ |
| Example 10-6(1) | o | o |
| Example 10-6(2) | o | o |

EXAMPLE 10-7

A 100 g amount of biotite powder was dispersed in 400 g of dichloromethane, and 3 g of methyl hydrogen polysiloxane (M.W.=ca. 3000) was added thereto. The whole was heated under reflux at 50° C. for 2 hours. After evaporating dichloromethane at 100° C., 1.0 g of styrene and 400 g of isopropyl alcohol containing 10 mg of chloroplatinic acid as a catalyst were added, and the whole was heated under reflux in a water bath for 2 hours. Thereafter, filtration by a glass filter and washing with isopropyl alcohol were performed, and the powder was dried at 80° C. The resultant modified powder, having a crosslinking ratio of 51% and an addition ratio of nearly 100% exhibited a remarkable water repellency with the linalool decomposition ability having disappeared.

EXAMPLE 10-8

A 20 g amount of phologopite having an average particle size of 5 μm was charged in a satellite ball mill, and mixed and ground for 5 minutes. Then, 1 g of hydrogen methyl polysiloxane (molecular weight=6,000) was added, followed by mixing and grinding for 3 hours. Thereafter, 0.5 g of docosene and 10 mg of tri-n-octylmethylammonium chloroplatinate were added, followed by mixing and grinding for 2 hours.

The resultant modified powder, having a crosslinking ratio of 30% and an addition ratio of nearly 100%, exhibited a remarkable water repellency with the linalool decomposition ability having disappeared.

EXAMPLE 10-9

(1) A 10 kg amount of synthetic mica obtained by substituting the OH group of muscovite with fluorine was charged into a 100 liter rotary double cone type reactor (made of stainless steel, equipped with a lagging jacket) and 10 kg of a silicone compound having the following structure:

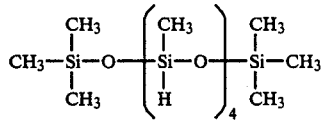

was charged into a stock liquor feeding tank (made of stainless steel, equipped with a lagging jacket) directly connected to the reactor by a stainless steel pipe. $N_2$ was charged through the feeding tank by bubbling $N_2$ into the tank. The temperature of the system was maintained at 70° C. by feeding a heating medium heated at 70° C. from the heating medium heating tank by a circulation pump to the lagging jackets of the reactor and the stock liquor feeding tank. The reactor was rotated three times after being allowed to stand for 10 minutes by means of a timer, which operation was repeated for 7 hours, and thereafter, the silicone compound was removed, N₂ was introduced into the reactor, and rotation was continued for 12 hours. Then, the temperature was returned to room temperature. Thus, 19.6 kg of the treated mica was obtained.

(2) Into a 1 l eggplant-shape flask, 100 g of the resultant synthetic mica was taken. Thereafter, 10 mg of chloroplatinic acid, 10 ml of 1-tetradecene and 500 ml of isopropanol were added thereto and the whole was heated under reflux in a water bath for 5 hours. Then, the filtration with a glass filter (G-4) and the washing with 600 ml of chloroform were carried out, and the powder was dried in a thermostatic chamber at 90° C. for 1 hour to yield the modified powder material. The resulting powder exhibited a remarkable hydrophobicity and the linalool decomposing ability disappeared. In the test of hydrogen generation, no hydrogen was detected.

EXAMPLE 10-10

A 1 g amount of muscovite having an average diameter of 2 μm and 9 g of a silicone compound having the following structure:

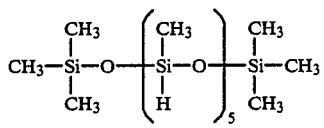

were charged into a sample tube, followed by allowing to stand at room temperature for 24 hours. The muscovite was expanded to a surface of the silicone compound liquid. The treated muscovite covered by the silicone polymer film obtained above was taken into a 100 ml Erlenmeyer flask, 1 ml of 1-pentene and 30 ml of isopropyl alcohol containing 10 mg of chloroplatinic acid as a catalyst were added thereto, and the whole was heated under reflux in a water bath for 2 hours. Thereafter, filtration by a glass filter and washing with 50 ml of isopropyl alcohol were carried out, and the powder was dried at 100° C. for 5 hours. The resulting modified muscovite exhibited a remarkable water repellency with the linalool decomposition ability having disappeared.

EXAMPLE 10-11

A 100 g amount of muscovite, 5 g of 2,2',4,4'-tetrahydroxybenzophenone and 300 ml of ethanol were mixed and dried at 80° C. The resultant powder and 20 g of tetrahydrogen tetramethyl cyclotetrasiloxane were placed in a desiccator at 80° C. and the vapor phase treatment was carried out for 16 hours to yield 112 g of the powder modified by the first stage treatment.

50 g of the resultant powder was dispersed in 300 ml of chloroform. Thereafter, 5 mg of tri-n-octylmethylammonium chloroplatinate and 5 g of 1-octadecene were added thereto and the whole was heated under reflux in a water bath for 5 hours. Then, the filtration with a glass filter (G-4) and the washing with 300 ml of chloroform were carried out, and the powder was dried in a thermostatic chamber at 60° C. for 5 hours to yield the modified powder material. The resulting powder exhibited a remarkable hydrophobicity. In the test of hydrogen generation, no hydrogen was detected.

EXAMPLE 10-12

The modified powder was obtained in the same manner as in Example 10-11, except that 5 g of methyl 2,5-diisopropyl cinnamate was used as a UV absorber in place of 5 g of 2,2',4,4'-tetrahydroxybenzophenone. The resulting powder exhibited a remarkable hydrophobicity. In the test of hydrogen generation, no hydrogen was detected.

Figure 6:
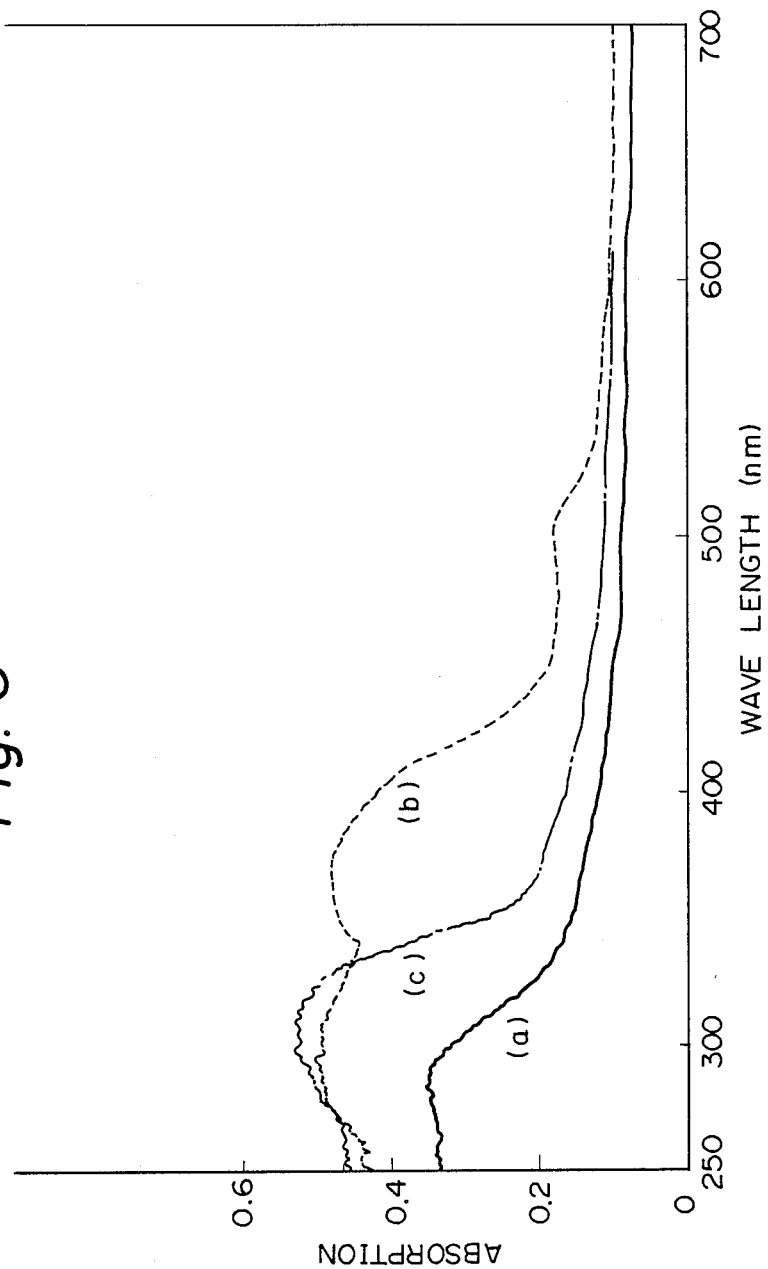
FIG. 6 shows the UV absorption spectrum of the muscovite powder samples of the untreated powder [i.e., chart (a)], Example 10-11 [i.e., chart (b)], and Example 10-12 [i.e., chart (c)].

A UV to visible spectrum of the modified powders of Examples 10-11 and 10-12, and the untreated powder was measured by means of a spectrophotometer UVI-DEC-610C (Jasco Co.). Referring to FIG. 6 showing the result, the UV absorbability was improved in the modified muscovite powders of Examples 10-11 and 10-12.

EXAMPLE 11-1

A 20 g amount of wool powder (average particle size of 10 μm) ground by a grinder and 5 g of tetrahydrogen tetramethyl cyclotetrasiloxane were separately charged into separate vessels, which were allowed to stand in a desiccator at 50° C. After 16 hours, the wool powder was taken out and dried at 60° C. for 2 hours to yield 20.6 g of the treated wool powder.

Into a 100 ml eggplant-shape flask, 10 g of the resultant wool powder was taken. Thereafter, 1 mg of chloroplatinic acid, 1 ml of 1-tetradecene and 30 ml of isopropanol were added thereto and the whole was stirred at room temperature for 16 hours. Then, the filtration with a glass filter (G-4) and the washing with 100 ml of chloroform were carried out, and the powder was dried at 80° C. for 1 hour. The resulting powder exhibited a remarkable hydrophobicity. In the test of hydrogen generation, no hydrogen was detected.

EXAMPLE 12-1

A mixture of 10 g of titanium dioxide, 10 g of muscovite, 35 g of sericite, 20 l g of talc, 3 g of iron oxide, and 10 g of tetrahydrogen tetramethyl cyclotetrasiloxane were separately charged into a separate vessels, which were placed in a desiccator. The system was allowed to stand at 80° C. for 10 hours. After 10 hours, 84 g of the mixture of the treated powders was allowed to stand at 80° C. for 4 hours in a dryer. Thus, 82.3 g of the mixture of treated powders was obtained. Then, 40 g of the resulting mixture was taken into a 100 ml eggplant-shape flask. 3 mg of tri-n-octylmethylammonium chloroplatinate as a catalyst and 200 ml of 1-octene were added thereto, and the whole was heated under reflux in a water bath for 5 hours. Then, filtration was carried out using a glass filter (G-4). Further, filtration and washing were performed with ethanol. Thereafter, the mixture was dried in a thermostatic chamber at 105° C. for 1 hour.

EXAMPLE 12-2

A mixture of 30 g of C.I. 15850:1, 30 g of boron nitride (hexagonal) and 10 g of titanium-mica pearling pigment, and 20 g of tetrahydrogen tetramethyl cyclotetrasiloxane were separately charged in separate vessels, which were placed in a desiccator and allowed to stand at 50° C. for 5 hours. After 5 hours, the powder was taken out and dried at 60° C. for 4 hours to obtain 74 g of the mixture of the treated powder materials.

The resultant mixture (35 g) was treated with 300 ml of isopropyl alcohol and 4 mg of chloroplatinic acid, and further, 7 ml of 1-octadecene, and the reaction was performed at room temperature for 16 hours. After filtration, washing with ethanol, and drying, the mixture of the modified powder materials was obtained.

EXAMPLE 12-3

(1) Into a vibration ball mill, 10 g of yellow iron oxide, 4.5 g of red iron oxide, 2 g of black iron oxide, 117 g of titanium dioxide, and 116.5 g of sericite were charged. The powder materials were mixed with alumina balls for 30 minutes. Then, 5 g of methyl hydrogen polysiloxane (M.W.=ca. 6,000) was added thereto and the mixing was carried out for further 30 minutes.

(2) Thereafter, 200 g of isopropanol containing 10 mg of chloroplatinic acid and then 10 g of 1-octadecene were added thereto, and mixed for 1 hour. Then, the filtration with a glass filter (G-4) and the washing with ethanol were carried out, and the product was dried to yield the modified composite powder material.

EXAMPLE 13-1

The following ingredients were throughly mixed in a ball mill in the following ratios. Thus, a coating composition was obtained.

| Ingredients | Parts |
| --- | --- |
| Powder material obtained in Example 3-1 | 100 |
| Vinyl chloride-vinyl acetate copolymer | 10 |
| Polyurethane resin | 20 |
| Toluene | 100 |
| Methyl ethyl ketone | 100 |

COMPARATIVE EXAMPLE 13-1

The coating composition was prepared in the same manner as in Example 13-1, except that the untreated powder material was used.

When the coating compositions obtained in Example 13-1 and Comparative Example 13-1 were coated on a polyester film in a conventional manner. When the coated films were visually evaluated, the coating composition of Example 13-1 exhibited a deep color and good gloss when compared to that of Comparative Example 13-1, due to the good dispersibility.

EXAMPLE 14-1

Preparation of Pressed Powder

The pressed powder having the following composition was prepared by using the modified powder materials according to the present invention.

| Ingredients | Parts |
| --- | --- |
| (1) Modified muscovite of Example 10-1(2) | 30 |
| (2) Modified talc of Example 7-2(2) | 65.8 |
| (3) Iron oxide pigment | 0.1 |
| (4) Squalane | 2.0 |
| (5) 2-Ethylhexyl palmitate | 2.0 |
| (6) Perfume | 0.1 |

The ingredients (1), (2), and (3) were mixed in a Henschel mixer, followed by spraying a heated mixture of the ingredients (4), (5), and (6), the mixture was then ground and molded in a container. Thus, the desired pressed powder was obtained.

COMPARATIVE EXAMPLE 14-1

The pressed powder was prepared in the same manner as in Example 14-1, except that the untreated muscovite and talc were used instead of the modified muscovite and talc.

The pressed powder compositions obtained in Example 14-1 and Comparative Example 14-1 were evaluated. The results are as follows:

| No. | Extendability | Cosmetic finish retainability | Water repellency | Odor stability |
| --- | --- | --- | --- | --- |
| Example 14-1 | | | | |
| Comparative Example 14-1 | Δ | Δ | xx | x |

O Excellent
⊙ Good
Δ Fair
x Poor
xx Bad

EXAMPLE 14-2

Preparation of Foundations

A foundation having the following composition was prepared.

| Ingredients | Parts |
| --- | --- |
| (1) Mixture of modified powder materials of Example 12-1 | 78 |
| (2) 2-Ethylhexyl palmitate | 5.5 |
| (3) Liquid paraffin | 5.0 |
| (4) Sorbitan sesquioleate | 1.0 |
| (5) Preservative | 0.3 |
| (6) Perfume | 0.2 |

A heated mixture of the ingredients (2), (3), (4), (5), and (6) was added to the ingredient (1), followed by mixing and grinding. The resultant composition was packed in a container. Thus, the desired foundation capable of being used either with or without water was obtained.

COMPARATIVE EXAMPLE 14-2

The foundation was prepared in the same manner as in Example 14-2, except that the modified powder was substituted with metallic soap.

The evaluation results are as follows:

| No. | Extendability | Cosmetic finish retainability | Water repellency |
| --- | --- | --- | --- |
| Example 14-2 | ⊚ | ⊚ | ⊚ |
| Comparative Example 14-2 | | | x |

⊚ ... Excellent
O ... Good
Δ ... Fair
x ... Poor

EXAMPLE 14-3

Preparation of Powder Eye Shadow

The eye shadow having the following composition was prepared.

| Ingredients | Parts |
| --- | --- |
| (1) Modified talc of Example 7-2(2) | 20 |
| (2) Modified pearling pigment of Example 6-2(2) | 18.5 |
| (3) Modified ultramarine blue of Example 3-1 | 50 |
| (4) Modified iron oxide of Example 4-1 | 4.0 |
| (5) Squalane | 4.0 |
| (6) Cetyl 2-ethyl hexanoate | 2.0 |
| (7) Sorbitan sesquioleate | 1.0 |

| Ingredients | Parts |
|---|---|
| (8) Preservative | 0.3 |
| (9) Perfume | 0.2 |

The ingredients (1) to (4) were mixed in a Henschel mixer and a heated mixture solution of the ingredients (5) to (9) was sprayed thereto. The resultant mixture was ground and then packed in a container. Thus, the desired eye shadow was obtained.

COMPARATIVE EXAMPLE 14-3

The eye shadow was prepared in the same manner as in Example 14-3, except that the modified talc, pearling pigment, and iron oxide were substituted with the unmodified powders, respectively.

COMPARATIVE EXAMPLE 14-4

The eye shadow was prepared in the same manner as in Example 14-3, except that all the modified powders of Example 14-3 were substituted with the unmodified powders.

The evaluation results are as follows.

| No. | Extendibility | Cosmetic finish retainability | Water repellency | Odor stability |
|---|---|---|---|---|
| Example 14-3 | ○ | ◎ | ◎ | ◎ |
| Comparative Example 14-3 | △ | x | x | ○ |
| Comparative Example 14-4 | △ | x | xx | x |

◉ ... Excellent
○ ... Good
△ ... Fair
x ... Poor
xx ... Bad

EXAMPLE 14-4

Preparation of Nail Enamel

The nail enamel having the following composition was prepared as follows:

| Ingredients | Parts |
|---|---|
| (1) Nitrocellulose | 12 |
| (2) Modified alkyd resin | 12 |
| (3) Acetyltributyl citrate | 5 |
| (4) Butyl acetate | 38.4 |
| (5) Ethyl acetate | 6 |
| (6) n-Butyl alcohol | 2 |
| (7) Toluene | 21 |
| (8) Modified red iron oxide of Example 4-3 | 0.5 |
| (9) Modified titanium dioxide of Example 4-2(3) | 0.1 |
| (10) Modified pearling pigment of Example 6-1(2) | 2 |
| (11) Organically modified Montmorillonite | 1 |

The ingredients (1) to (3) and (5) to (7) and a portion of the ingredient (4) were dissolved and a gelled mixture of the component (11) and the remainder of the component (4) was added, followed by adding the ingredients (8) to (10). The resultant mixture was packed in a container to obtain the desired mail enamel.

COMPARATIVE EXAMPLE 14-5

The nail enamel was prepared in the same manner as in Example 14-4, except that the modified powders of Example 14-4 were substituted with the untreated powders.

The nail enamel of Example 14-4 was superior to that of Comparative Example 14-5 in the dispersion stability of the pigments and a lower adherence of the content to the container.

EXAMPLE 14-5

UV Preventive Stick

The UV light preventive stick having the following composition was prepared as follows:

| Ingredients | Parts |
|---|---|
| (1) Modified titanium dioxide of Example 4-2(2) | 20 |
| (2) Modified talc of Example 7-2(2) | 10 |
| (3) Modified muscovite of Example 10-1(2) | 11 |
| (4) Iron oxide (red, yellow, black) | 0.5 |
| (5) Carnauba wax | 1 |
| (6) Solid paraffin | 3 |
| (7) Liquid paraffin | 45 |
| (8) Isopropyl myristate | 8 |
| (9) Sorbitan sesquioleate | 1.5 |
| (10) Perfume | q.s. |

The ingredients (7) and (8) were charged into a still and heated to 80° C. to 90° C. and the ingredients (5) and (6) were added thereto. Then, the ingredients (1) to (4) were added and uniformly dispersed. After degassing, the component (10) was added and the resultant mixture was gently stirred. The mixture having a temperature of 80° C. was cast into a container and cooled to room temperature. Thus, the desired UV preventive stick was obtained.

COMPARATIVE EXAMPLE 14-6

The UV preventive stick was prepared in the same manner as in Example 14-5, except that the modified titanium dioxide was substituted with the untreated titanium dioxide.

The stick obtained in Example 14-5 was superior to that of Comparative Example 14-6 in the dispersibility of the titanium dioxide, the cosmetic finish, and in the suntan preventive effect.

EXAMPLE 14-6

Preparation of Lipstick

The lipstick having the following composition was prepared:

| Ingredients | Parts |
|---|---|
| (1) Hydrocarbon wax | 3 |
| (2) Carnanba wax | 1 |
| (3) Glyceryl isostearate | 40 |
| (4) Liquid paraffin | 45.8 |
| (5) Modified titanium dioxide of Example 4-2(2) | 4 |
| (6) Modified powder mixture of Example 12-2 | 6 |
| (7) Perfume | 0.2 |

The ingredients (1) to (3) and (4) were dissolved at 85° C. and the ingredients (5) and (6) were added thereto, while stirring. Finally the ingredient (7) was mixed while stirring. The resultant mixture was packed into a container. Thus, the desired lipstick having excellent dispersibility was obtained.

EXAMPLE 14-7

Preparation of Emulsion Type Foundation

An emulsion type foundation was prepared from the following formulation.

| Ingredients | Parts |
| --- | --- |
| (A) Ion-exchanged water | 43.5 |
| Sodium chondroitin sulfate | 1 |
| Sodium lactate | 0.5 |
| 1,3-butylene glycol | 3 |
| Methylparaben | q.s, |
| (B) Dimethyl polysiloxane (20 cs) | 16 |
| Decamethyl cyclopentasiloxane | 5 |
| Silicone resin | 1 |
| Cetyl isooctanate | 1 |
| Organopolysiloxane modified with polyoxyalkylene (modification ratio: 20%) | 4 |
| Antioxidant | q.s, |
| Perfume | q.s, |
| (C) Mixture of modified powder of Example 12-3(2) | 25.0 |

After the composition (B) was melted by heating, the composition (C) was added and dispersed therein. The composition (A) previously melted was added thereto. The whole was emulsified and cooled to room temperature to prepare the emulsion type foundation.

COMPARATIVE EXAMPLE 14-7

The emulsion type foundation was prepared in the same manner as in Example 14-7, except that the mixture of modified powder of Example 12-3(1) was used as the component (C).

The evaluation results are shown in Table 14-1.

TABLE 14-1

| | Example 14-7 | Comparative Example 14-7 |
| --- | --- | --- |
| Appearance*[1] | good | good |
| Stability*[2] | good | cell generation |
| Hydrogen generation*[3] | not blackened | blackened |
| Contact angle*[4] | 92° | 70° |

*[1] Evaluated with the naked eye.
*[2] Evaluated with the naked eye after allowing to stand for a month at 0° C., 37° C., 50° C. and room temperature.
*[3] Evaluated the color change of the hydrogen detector tube (Gastec-Suiso 30: Kitazawa Sangyo k.k.), after charging 5 g of the sample into a 20 ml sample tube and allowing to stand for 15 hours.
*[4] Measured the contact angle after applying the sample on a glass plate by means of a 0.35 mm doctor blade, allowing to stand for 1 day, dropping 2 μl of water droplet thereon and allowing to stand for 30 seconds.

The foundation of Example 14-7 did not generate hydrogen, had a good water repellency (this is apparent from the high contact angle), and had an excellent stability and usability in comparison with that of Comparative Example 14-7.

EXAMPLE 14-8

Preparation of Emulsion Type Foundation

An emulsion type foundation was prepared from the following formulation.

| Ingredients | Parts |
| --- | --- |
| (A) Ion-exchanged water | 40.5 |
| Propylene glycol | 2 |
| 1,3-butylene glycol | 3 |
| Potassium hydroxide | 0.5 |
| (B) Liquid paraffin | 10 |
| Cetyl isooctanate | 10 |
| Veseline | 2 |
| Palmitic acid | 1 |
| Stearic acid | 2 |
| Polyoxyethylene (20 mol) Glyceryl monostearate | 2 |
| Diglyceryl isostearate | 2 |
| Preservative | q.s, |
| Perfume | q.s, |
| (C) Mixture of modified powder of Example 12-3(2) | 25.0 |

After the composition (B) was melted by heating, the composition (C) was added and dispersed therein. The composition (A) previously melted was added thereto. The whole was emulsified and cooled to room temperature to prepare the emulsion type foundation.

EXAMPLE 14-9

Preparation of Foundation (Powder/Oil Type)

A foundation (powder/oil type) was prepared from the following formulation.

| Ingredients | Parts |
| --- | --- |
| (A) Decamethyl cyclopentasiloxane | 48.5 |
| Ethyl alcohol | 10 |
| Dimethyl polysiloxane (20 cs) | 10 |
| Isooctyl p-aminobenzoate | 1 |
| Sorbitan isostearate | 0.5 |
| Perfume | q.s, |
| (B) Mixture of modified powder of Example 12-3(2) | 30.0 |

After the composition (A) was melted by heating, the composition (B) was added and dispersed therein to prepare the foundation (powder/oil type).

EXAMPLE 14-10

Preparation of Base Make-up Lotion

A base make-up lotion was prepared from the following formulation.

| Ingredients | Parts |
| --- | --- |
| (A) Ion-exchanged water | 81.15 |
| 1,3-butylene glycol | 5 |
| Propylene glycol | 5 |
| Carboxyvinyl polymer | 0.2 |
| (B) Jojoba oil | 3 |
| Squalane | 1 |
| Glyceryl trioctanate | 1 |
| Vaseline | 0.5 |
| Cetanol | 0.5 |
| Glyceryl monooleate | 0.5 |
| Polyoxyethylene-polyoxypropylene cetyl ether | 1.5 |
| Preservative | q.s, |
| Perfume | q.s, |
| (C) Modified iron oxide of Example 1-1 | 0.05 |
| Modified muscovite of Example 10-1(2) | 1.0 |
| (D) Potassium hydroxide | 0.1 |

After the composition (B) was melted by heating at 70° C., the composition (C) was added thereto. The composition (A) previously melted and then the composition (D) were added thereto. The whole was emulsified to prepare the base make-up lotion.

The cosmetic compositions obtained in Examples 14-7 to 14-10 had excellent stability and usability without any deterioration caused by powders.

We claim:
1. A modified powder coated on substantially the entire surface thereof with a film of a silicone polymer carrying a pendant group on one side thereof opposite the other side which is in contact with the surface of said powder, said powder being produced by a process comprising the steps of
   (a) coating the powder with a film of a silicone polymer having at least one Si—H moiety, and
   (b) carrying out an addition reaction of a compound capable of reacting with an Si—H moiety, to the Si—H moiety in the outer surface of the film of the silicone polymer of step (a), whereby the pendant group derived from said compound is bonded to the outer surface of the film of the silicone polymer.

2. A modified powder or particulate material as claimed in claim 1, wherein said film of said silicone polymer of step (a) is derived from a silicone compound having at least one Si—H moiety.

3. A modified powder as claimed in claim 2, wherein the silicone compound used in step (a) is a silicone compound having a general formula (I):

wherein $R^1$, $R^2$, and $R^3$ represent, independently, hydrogen or a hydrocarbon residue having 1 to 10 carbon atoms, which may be substituted with at least one halogen atom, provided that $R^1$, $R^2$, and $R^3$ are not hydrogen at the same time, $R^4$, $R^5$, and $R^6$ represent, independently, hydrogen or a hydrocarbon residue having 1 to 10 carbon atoms, which may be substituted with at least one halogen atom, a is zero or an integer of 1 or more, b is zero or an integer of 1 or more, and c is zero or 2, provided that a+b is an integer of 3 or more when c is zero, and the maximum value of a+b+c is 10,000.

4. A modified powder as claimed in claim 2, wherein the silicon compound is brought into contact with the powder having an active site on the surface thereof, said active site capable of catalytically polymerizing a silicon compound having a siloxane bond or a hydrosilyl moiety, whereby the silicone compound is polymerized on substantially the entire surface of the powder to form said film of silicone polymer.

5. A modified powder as claimed in claim 4, wherein the silicone compound in the form of a vapor is brought into contact with the powder or particulate material.

6. A modified powder as claimed in claim 4, wherein the silicone polymer formed in step (a) has a weight-average molecular weight of more than 200,000.

7. A modified powder as claimed in claim 5, wherein, in step (a), the silicone compound is brought into contact with the powder or particulate material at a temperature of 120° C. or less in a closed chamber in such a manner that the vaporized silicone compound is deposited under a molecular state on the surface of the powder.

8. A modified powder as claimed in claim 7, wherein the silicone compound is brought into contact with the powder under a pressure of 200 mmHg or less.

9. A modified powder as claimed in claim 5, wherein, in step (a), the silicone compound is brought into contact with the powder by feeding a gas mixture of the silicone compound and a carrier gas.

10. A modified powder as claimed in claim 9, wherein the silicone compound is brought into contact with the powder at a temperature of 120° C. or less.

11. A modified powder as claimed in claim 2, wherein, in step (a), the silicone compound is dissolved in a solvent and brought into contact with the powder.

12. A modified powder as claimed in claim 2, wherein, in step (a), the silicone compound in the form of a liquid is brought into contact with the powder or particulate material.

13. A modified powder as claimed in claim 12, wherein the contact is mechanochemically effected.

14. A modified powder as claimed in claim 1, wherein, in step (a), the powder or particulate material is coated with said film of silicone polymer having Si—H moieties in an amount of 1% or more of the total Si atoms contained in the silicone polymer.

15. A modified powder as claimed in claim 1, wherein said compound used in step (b) is an unsaturated hydrocarbon compound or a compound having an OH group or SH group.

16. A modified powder as claimed in claim 15, wherein the unsaturated hydrocarbon compound is a compound having the general formula (V):

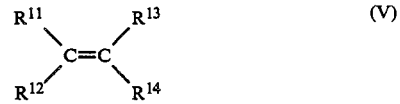

wherein $R^{11}$, $R^{12}$, $R^{13}$, and $R^{14}$ represent, independently, hydrogen, halogen, hydroxyl, mercapto, acyloxy, alkoxy, amino, nitro, carboxyl, sulfo, or an unsubstituted or substituted hydrocarbon residue having 1 to 30 carbon atoms, or $R^{11}$ and $R^{13}$ may represent a single bond to thereby from —C≡C—, or $R^{12}$ and $R^{14}$ may form, together with —C=C—, an alicyclic ring.

17. A modified powder as claimed in claim 1, wherein said material is an inorganic pigment.

18. A modified powder as claimed in claim 1, wherein said material is a metallic oxide or hyroxide.

19. A modified powder as claimed in claim 1, wherein said material is a mica.

20. A modified powder as claimed in claim 1, wherein said material is an organic pigment.

21. A modified powder as claimed in claim 1, wherein said material is a pearling pigment.

22. A modified powder as claimed in claim 1, wherein said material is a mineral silicate.

23. A modified powder as claimed in claim 1, wherein said material is a porous material.

24. A modified powder as claimed in claim 1, wherein said material is a carbon.

25. A modified powder as claimed in claim 1, wherein said material is a metal.

26. A modified powder as claimed in claim 1, wherein said material is a composite powder or particulate.

27. A modified powder as claimed in claim 1, wherein said powder is a biopolymer.

28. A cosmetic composition comprising a modified powder of claim 1.

29. A coating composition comprising a modified powder of claim 1.

30. A modified powder as claimed in claim 3, wherein the silicone compound is brought into contact with the powder having an active site on the surface thereof, said active site capable of catalytically polymerizing a silicone compound having a siloxane bond or a hydroxysilyl moiety, whereby the silicone compound is polymerized on substantially the entire surface of the powder to form said film of silicone polymer.

31. A modified powder as claimed in claim 30, wherein the silicone compound in the form of a vapor is brought into contact with the powder or particulate material.

32. A modified powder as claimed in claim 31, wherein the silicone compound used in step (a) is a cyclic silicone compound having the general formula (I) in which a+b is 3 to 7 and c is zero, provided that the compound has at least two Si—H moieties.

* * * * *

UNITED STATES PATENT AND TRADEMARK OFFICE
CERTIFICATE OF CORRECTION

PATENT NO. : 4,818,614
DATED : April 4, 1989
INVENTOR(S) : Hiroshi Fukui, et al

It is certified that error appears in the above-identified patent and that said Letters Patent is hereby corrected as shown below:

On the title page, under item [30]
"Foreign Priority Data"  After last entry insert
--June 13, 1986 [JP] Japan.... 61-137841--

Col. 2, line 54  Delete "alters color" and substitute --color alters--

Col. 13, line 38  Delete "mice" and substitute --mica--

Col. 15, line 45  Delete "witn" and substitute --with--

Col. 17, line 53  Delete "nacreaous" and substitute --nacreous--

Col. 19, line 67  Delete "inksm" and substitute --inks,--

Col. 22, line 19  Delete "liopophilicity" and substitute --lipophilicity--

Col. 22, line 56  Delete "dimehtyl" and substitute --dimethyl--

Col. 22, line 59  Delete "etyl" and substitute --ethyl--

Col. 22, line 63  Insert --agents.-- after "thickening"

Col. 24, line 59  Delete "pured" and substitute --poured--

Col. 25, line 47  Insert --ml-- after "100"

Col. 32, line 63  Delete "decosene" and substitute --docosene--

Col. 46, line 30  Delete "time" and substitute --times--

UNITED STATES PATENT AND TRADEMARK OFFICE
CERTIFICATE OF CORRECTION

PATENT NO. : 4,818,614

DATED : April 4, 1989

INVENTOR(S) : Hiroshi Fukui, et al.

It is certified that error appears in the above-identified patent and that said Letters Patent is hereby corrected as shown below:

| | |
|---|---|
| Col. 50, line 50 | Delete "the" after "To" and substitute --a-- |
| Col. 50, line 64 | Delete "allowed" and substitute --allowing-- |
| Col. 60, line 39 | Delete "l" before "g" |

Signed and Sealed this

Twentieth Day of March, 1990

*Attest:*

JEFFREY M. SAMUELS

*Attesting Officer*   *Acting Commissioner of Patents and Trademarks*

UNITED STATES PATENT AND TRADEMARK OFFICE
CERTIFICATE OF CORRECTION

PATENT NO. : 4,818,614

DATED : April 4, 1989

INVENTOR(S) : Hiroshi Fukui, et al

It is certified that error appears in the above-identified patent and that said Letters Patent is hereby corrected as shown below:

Col. 20, line 55      Delete "biopolyer" and substitute --biopolymer--

Signed and Sealed this

Eleventh Day of February, 1992

Attest:

HARRY F. MANBECK, JR.

*Attesting Officer*    *Commissioner of Patents and Trademarks*